US006803195B1

(12) United States Patent
Avivi et al.

(10) Patent No.: US 6,803,195 B1
(45) Date of Patent: Oct. 12, 2004

(54) FACILE DETECTION OF CANCER AND CANCER RISK BASED ON LEVEL OF COORDINATION BETWEEN ALLELES

(75) Inventors: Lydia Avivi, Carmey-Yoseph (IL); Aviva Dotan, Hasharon (IL); Yehoshua Ravia, Givatayim (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 673 days.

(21) Appl. No.: 09/660,328

(22) Filed: Sep. 12, 2000

Related U.S. Application Data

(63) Continuation-in-part of application No. 09/345,029, filed on Jul. 2, 1999, now abandoned.

(51) Int. Cl.[7] .................................................. C12Q 1/68

(52) U.S. Cl. ........................................................ 435/6

(58) Field of Search .............................................. 435/6

(56) References Cited

U.S. PATENT DOCUMENTS 6,235,474 B1 * 5/2001 Feinberg ........................ 435/6

OTHER PUBLICATIONS

Amiel A., Korenstein A., Gaber E., Avivi, L., "Asychronous replication of alleles in genomes carrying an extra autosome", European Journal of Human Genetics 7, 223–230 (1999).
Atkins, L., Taft P., Kalal K., "Asynchronous DNA synthesis of sex chromatin in human interphase nuclei", J Cell Biol, 15:390–393 (1962).
Avivi L., Dotan A., Ravia Y., Amiel A., Schacham h., Neumann Y. "Increased spindle resistance to antimicrotubule agents in cells prone to chromosomal nondisjuction", Human Genet, 83:165–170 (1989).
Boggs, B., Chinault A., "Analysis of the replication timing properties of human X-chromosomal loci by fluorescence in–situ hybridization", Proc. Natl. Acad. Sci. USA, 91:6083–6087 (1994).
Boggs. B., Chinault A., "Analysis of DNA replication by fluorescence in situ hybridization", METHODS, 13:259–270 (1997).
Chess A., "Expansion of the allelic exclusion principle?", SCIENCE 279:2067–2068 (1998).
Chess A., Simon I., Cedar H., Axel R., "Allelic inactivation regulates olfactory receptor gene expression", CELL 78:823–834 (1994).
Cul h., Horon I., Ohlsson R., Hamilton S., Feinberg A., "Loss of imprinting in normal tissue of colorectal cancer patients with microsatellite instability", NAT MED 4:1276–1280 (1998).

Dhar V., Magar D., Iqbal A., Schildraut C., "The coordinate replication of the human β–glogin gene domain reflects its transcriptional activity and nuclease hypersensitivity", Mol Cell Biol 8:4958–4965 (1988).
Dhar V., Skoultchi A., Schilddraut C., "Activation and repression of a β–golbin gene in cell hybrids is accompanied by a shift in its temporal replication", Mol Cel Biol 9:3524–3532 (1989).
Dotan Z., Dotan A., imanovitch T., Ravia Y., Oniashvili N., Leibovitch, I., Ramon J., Avini L., "Allele–specific mode of replication in pheriphera lymphocytes of rena cell carcinoma patients: A new aspect of genomic instability", Annual Meeting at the American Urological Association, May 1999, Dallas, Texas.
Dotan Z., Dotan A., imanovich T., Ravia Y., Oniashvili N., Leibovitch I., Ramon J., Avivi L., "Allele–specific mode of replication in periphera lymphocytes of rena cell carcinoma patients: A new aspect of genomic instability—a possible clinical use—part II", Annual Meeting at the American Urological Association, Eilat, Israel, Nov. 1998.
Epner E., Forrester W., Groudine M., "Asynchronous DNA replication within the human β–gobin gene", Proc Natl Acad Sci USA, 858081–8085 (1988).
Feinberg A., "Genomic imprinting and cancer", The Genetic Basis of Human Cancer, Vogelstein B., Kinzler L., eds., McGraw–hill, New York pp. 95–107 (1998).
Goldman, M., holmquist, G., Gray M., caston L., Nag A., "Replication timing of genes and middle repetitive sequences", SCIENCE 224:686–692 (1984).
Grumbach M., Morishima A., Taylor J., "Human sex chromosome abnormalities in relation to DNA replication and heterochromatinization." Roc Natl Acad Sci USA, 49:581–589 (1963).

(List continued on next page.)

Primary Examiner—Kenneth R. Horlick
(74) Attorney, Agent, or Firm—Browdy and Neimark, PLLC

(57) ABSTRACT

There is provided a method for the detection of cancer and cancer risk by analyzing the coordination between alleles within isolated cells whereby an alteration in an inherent pattern of coordination within isolated cells corresponds to cancer or cancer risk. Also provided is a method of determining the genotoxic effect of various environmental agents and drugs by assaying isolated cells to determine the coordination between alleles following in-vivo and/or in-vitro exposure to the various agents. Allelic coordination characters are selected from replication, conformation, methyalation and acetylation patterns. A diagnostic test for detecting cancer or the risk of cancer having an allelic replication viewing device for viewing the mode of allelic replication of a DNA entity, a standardized table of replication patterns and an analyzer to determine an altered pattern of replication, whereby such altered pattern is a cancer characteristic is also provided. There is also provided a method for differentiating between hematological and solid malignancies by following mono allelic expressede sequences and analyzing the replication status of the sequences to distinguish between hematological and solid malignancies.

45 Claims, 19 Drawing Sheets

OTHER PUBLICATIONS

Gunaratne, P., Nakao M., Ledbetter D., Sutcliffe J., Chinault A., "Tissue–specific and allele–specific replication timing control in the imprinted human Prader–Willi syndrome region", Genes & Dev 9:808–820 (1995).

Hatton K., Dhar V., Brown E., Iqbal M., Stuart S., Didamo V., Schidkraut C., "Replication program of active and inactive multigene families in mammalian cells", Mol. Cell Biol, 8:2149–2158 (1988).

Hollander G., Zuklys S., Morel C., Mizoguchi E., Mobisson K., Simpson S., Terhorst C., Wishart W., Golan D., Dhan A., burakoff S., "Monalelic expression of the interleukin–2 locu", SCIENCE 279:2118–2121 (1998).

Holmquist G., "Role of replication time in the control of tissue specific gene expression" Am J Hum Genet. 40:151–173 (1987).

Jackson A., Loeb L, "The mutation rate and cancer" GENETICS 148:1483–1490 (1998).

Kinzler K., Vogelstein B., Colorectal tumors: The Metabolic and Molecular Bases of at Inherited Disease, 7th ed. vol. 1, Scriver C., Beaudet A., Sly W., Valle D., eds., McGraw–Hill, New York, pp. 643–663 (1995).

Kitsberg D., Selig S., Brandeis M., Simon 1., Keshet I., Driscoll D., Nicholls R., Cedar H., "Allele–specific replication timing of imprinted gene regions," NATURE 364:459–463 (1993).

Knoll J., Cheng S., Lalande M., "Allele specificity of DNA replication timing in the Angelman/Prader–Willi syndrome impnuted chromosomal region," Nat Genet 6:41–46 (1994).

Knudson A., "Antioncogenes and human cancer," Proc Natl Acad Sci USA 90:10914–10921 (1993).

LaSalle J., Lalande M., "Domain organization of allele–specific replication within the GABRB3 gene cluster requires a biparental 15q1 1–13 contribution," Nat Genet 9:386–394 (1995).

Levanon D., Negreanu V., Bernstein Y., Bar–Am I., Avivi L., Groner Y., "AML1, AML2, and AML3, the human members of the runt domain gene–family: cDNA structure, expression and chromosomal localization," GENOMICS 23:425–432 (1994).

Latt et al., "Patterns of late replication in X chromosomes of human Lymphoid cells," Genet Cytogenet 3:171–181 (1981).

Levine, A., "p53, the cellular gatekeeper for growth and division," CELL 88:323–331 (1981).

Lima de Faria A., Jaworska H., "Late DNA synthesis in heterochromatin," NATURE 217:13 8–142 (1968).

Linehan W., Lerman M., Zbar B., "Identification of the VHL gene: its role in renal cancer," JAMA. vol. 273, No. 7, pp. 564–570 (1995).

Litmanovitch T., Altaras M., Dolan A., Avivi L., "Asynchronous replication of homologous α–satellite DNA loci in man is associated with non–disjunction," Cytogenet Cell Genet 81:26–35 (1998).

Loeb L., "Mutator phenotype may be required for multistage carcmogenesis," Cancer Res 51:3075–3079 (1991).

Look T., "Genes altered by chromosomal translocations in leukemia and lymphomas," The Genetic at Basis of Human Cancer, Vogelstein B., Kinder K., eds., McGraw–Hill, New York, pp. 109–141 (1998).

Miller O., Schnedl W., Allen J., Erlanger B., "5–Methylcytosine localized in mammalian constitutive heterochromatin," NATURE 251:636–637 (1974).

Miller O., "Is the centromeric hetrochromatin of Mus musculus late replicating?," CHROMOSOMA 55: 165–170 (1976).

Mukherjee A., Murty V., Chaganti R., "Detection of cell–cycle stage by fluorescence in situ hybridization: its application in human interphase cytogenetics," Cytogenet Cell Genet 61:91–94 (1992).

Ohlsson R., Tycko B., Sapienza C., "Monoalleic expression: there can only be one," TIG vol. 14, No. 11, pp. 435–438 (1967).

Priest J., Heady J,, Priest R., "Delayed onset of replication of human X chromosomes," J Cell Biol, 35:483–487 (1967).

Randhawa G., Cui H., Barletta J., Strichman–Almashanu L., Taipaz M., Kantaliian H., Deisseroth A., Champlin R., Feinberg A., "Loss of imprinting in disease progression in chronic myelogenous leukemia," BLOOD vol. 91, No. 9, pp. 3144–3147 (1998).

Selig S., Ariel M., Goitein R., Marcus M., Cedar H., "Regulation of mouse satellite DNA replication time," EMBO J vol. 7, No. 2, pp. 419–426 (1988).

Selig S., Okumura K., Ward D., Cedar H., "Delineation of DNA replication time zones by fluorescence in situ hybridization." EMBO J vol. 11. No. 3, pp. 1217–1225 (1992).

Smrzka O., Fae I., Stoger R., Kurzbauer R., Fischer G., Henn T., Weith A., Barlow D., "Conservation of maternal–specific methylation signal at the human IGF2R locus," Hum Mol Genet, vol. 4, No. 10, pp. 1945–1952 (1995).

Taylor J., "Asynchronous duplication of chromosomes in cultured cells of Chinese hamster," J Biophys Biochem Cytol, 7:455–464 (1960).

Ten Hagen K., Gilbert D., Willard H., Cohen S., "Replication timing of DNA sequences associated with human centromeres and telomeres," Mol Cell Biol 10:6348–6355 (1990).

Torchia B., Call L., Migeon B., "DNA replication analysis of FMRI, XIST, and factor 8C loci by FISH shows nontranscribed X–linked genes replicate late.," Am J Hum Genet 55:96–104 (1994).

White, L., Rogan P., Nicholls R., Wu B., Korf B., Knoll J., "Allele–specific replication of 15q1 1–q13 loci: a diagnostic test for detection of uniparental disomy," Am J Hum Genet 59:423–430 (1996).

Willard H., Lad S., "Analysis of deoxyribonucleic acid replication in human X chromosomes by fluorescence microscopy," Am J Hum Genet 28:213–227 (1976).

Yeshaya J., Shalgi R., Shohat M., Avivi L., "FISH–detected delay in replication timing of mutated FMRI AT alleles on both active and inactive X–chromosomes," Hum Genet (in press) (1999).

Dolan et al., "Numerical chromosome aberrations in nonmalignant cells derived from children suffering from different neoplasias," American Journal of Human Genetics, 49(4)1312 (1991).

Bar–am et al., "Numerical chromosome aberrations in nonmalignant lymphocytes derived from patients suffering from different types of neoplasia," Journal of Cancer Research and Clinical Oncology, 116(Suppl., Part I):S 1–772 (1990).

Bar–Am et al., "Increased level of aneuploidy in peripheral blood lymphocytes derived from patients with prostate cancer," Urological Research, 21(6)P61 (1993).

Mukamel et al., "The effect of bilateral orchiectomy on the behavior of PHA–stimulated lymphocytes in patients with prostatic cancer", The Journal of Urology, 516A (1989).

Amiel et al., "Asynchronous replication of p53 and 21q22 loci in chronic lymphocytic leukemia", *Hum Genet*, 101:219–222 (1997).

Amiel et al., "Replication pattern of the p53 and 21q22 loci in the premalignant and malignant stages of carcinoma of the cervix", American Cancer Society, 1965–1971 (1998).

Amiel et al., "Temporal differences in replication timing of homologous loci in malignant cells derived from CML and lymphoma patients", Genes, Chromosomes & Cancer 22:225–231 (1998).

Dotan et al., "Modification in the inherent mode of allelic replication in lymphocytes of patients suffering from renal cell carcinoma: A novel genetic alteration associated with malignancy", Genes, Chromosomes & Cancer, 27:270–277 (2000).

Amiel et al., "Replication status as a marker for predisposition for lymphoma in patients with chronic hepatitis C with and without cryoglubulinemia", Experimental Hematology, 1–5 (2000).

Tockman et al., "Considerations in bringing a cancer biomarker to clinical application", Cancer Research (Suppl.) 52:2711s–2718s (1992).

Amiel et al., "Asynchronous replication of allelic loci in Down Syndrome", European Journal of Human Genetics, 6:359–364 (1998).

* cited by examiner

Frequency of SD cells arranged in increasing order of the BRC (circles) and CON (triangles) samples. a. HER2, b. D17Z1 and c. average of both loci.

frequency of chromosome 17 losses and total aneuploidy for the same chromosome (losses+gains) in CON and BRC lymphocytes. N=sample size.

The weighted mean of SD values obtained for both HER2 and D17Z1 loci as a function of losses+gains of chromosome 17.

FACILE DETECTION OF CANCER AND CANCER RISK BASED ON LEVEL OF COORDINATION BETWEEN ALLELES

CROSS REFERENCE TO RELATED APPLICATIONS

This application is a continuation-in-part of U.S. patent application Ser. No. 09/345,029, filed Jul. 2, 1999, abandoned, which is incorporated herein by reference.

FIELD OF THE INVENTION

The invention relates to a method for early detection and diagnosis of cancer.

BACKGROUND OF THE INVENTION

It is, today, an accepted dogma that a developing neoplasm is the result of genomic instability expressed by a multitude of changes in the genetic material (Loeb and Christians, 1996, Jackson and Loeb, 1998). The number of events required to occur for this process to culminate in a neoplasm has been estimated to be far in excess of that which can be accounted for by the normal mutation rate. It has therefore been suggested that carcinogenesis can occur only if the cancer-predisposed genome acquires a "mutator" phenotype making it more mutable than its normal counterpart (Loeb 1991). Evidently, genomic instability depends on the fidelity of DNA replication, of DNA repair and of chromosome segregation. Indeed, consistent errors in DNA repair mechanisms resulting in multiple subtle changes at the nucleotide level were well documented in relation to oncogenesis. Similarly, a persistent damage in the segregating apparatus, causing DNA alterations at the chromosome level, expressed in an increased rate of losses and gains of whole chromosomes, was reported in connection with cancer (reviewed in Lengauer et al 1998a). Although, each of these errors enables the accumulation of multiple changes in the DNA compliment of an affected genome, these alterations are not too common. Changes at the nucleotide level appear only in a small portion of tumors, and the persistent damage caused to the segregating apparatus was, so far, observed in only few colon cancer cell lines (Lengauer et al 1998b).

An important aspect of DNA replication fidelity is the temporal control of the process. Accordingly, the specific time interval during DNA synthesis (S-phase of the cell cycle) at which a given DNA sequence is replicated appears to be a reliable indicator of transcriptional activity. However, it is not known yet whether the temporal order of replication is the cause or the effect of expression. Specifically, expressed DNA loci usually undergo early replication, while unexpressed ones tend to replicate late. This conclusion is based on several lines of evidence: (i) tissue-specific genes replicate early in cell types in which they are expressed and late in tissues in which they are silent (Selig et al. 1992, and reference therein); (ii) housekeeping genes, whose products are essential for cell maintenance, replicate early in most cells (Goldman et al. 1984; Holmquist 1987); (iii) DNA segments lacking transcriptional ability, such as satellite DNA, generally replicate late in S-phase (Selig et al. 1988; Ten Hagen et al. 1990, and references therein); (iv) the inactive X-chromosome in eutherian female cells is the last chromosome to replicate (Willard and Latt 1976, and references therein); and finally (v), most of the monoallelicaly expressed loci examined to date, manifest an allele-specific mode of replication, i.e., an early and a late replicating allele, in contrast to biallelically expressed loci which usually replicate highly synchronously (Ohlsson et al. 1998).

Most of the aforementioned cases were demonstrated by classical replication assays based on 5-bromodeoxyuridine (BrdU) incorporation, either in synchronized cells or in asynchronous cells fractionated by centrifugal elutriation, both followed by Southern blot hybridization of the newly synthesized BrdU-labeled DNA (reviewed in Boggs and Chinahult 1997). While it is possible to use these replication timing methods in the method of the invention, they are based on BrdU incorporation, and laborious, and require specific polymorphic markers or consistent differences in methylation levels for identification of individual alleles, which are not always available.

Using fluorescence in situ hybridization (FISH), it is possible to detect the presence of alleles and their replication status. A nonreplicated allele is detected as a single spot, whereas following replication, when the two chromatids are still located together, the allele is detected as a double spot. The presence of a single spot and a double spot in the same cell (hereinafter referred to as SD cell) therefore indicates that the two alleles are not replicating simultaneously (asynchronous replication; Selig et al. 1992; Boogs and Chinault, 1997).

Asynchrony of imprinted loci was clearly documented by FISH in the Prader-Willi syndrome locus; the paternal allele replicates earlier than the maternal allele which is usually silent (Kitzberg et al. 1993). On the other hand, FISH showed that in cells of individuals with uniparental disomy for the Prader-Willi syndrome locus the two alleles replicated highly synchronously, revealing loss of the asynchronous pattern of replication characterizing imprinted loci (Knoll et al. 1994; White et al. 1996).

Recently, the present inventors demonstrated by FISH that homologous regions at the TP53, CMYC, HER2, and D21S55 loci, each known to accommodate genes associated with various aspects of malignancy, replicate highly synchronously in different types of normal diploid cells, such as peripheral blood lymphocytes (Amiel et al. 1997, 1998a), bone-marrow cells (Amiel et al. 1998a), and amniotic fluid cells (Amiel et al.1998b, 1999a). On the other hand, these same loci, when present in lymphocytes and bone marrow cells of patients suffering from blood malignancies (CLL, CML and lymphoma), show loss of replication synchrony, (Amiel et al. 1997, 1998a). In light of the tight association between allele-specific replication and allele-specific expression it is reasonable to assume that all four aforementioned loci when present in lymphocytes and bone marrow cells of patients suffering from hematological cancers are subjected to some epigenetic mechanism leading to monoallelic expression. This assumption may be supported by the finding that changes in the mode of expression of an imprinted gene, a phenomenon often occurring in association with cancer and referred to as loss of imprinting (LOI), has been observed in lymphocytes and bone marrow cells of patients suffering from chronic myelogenous leukemia (Randhawa et al. 1998).

Moreover, the present inventors demonstrated by FISH that even the replication timing of homologous DNA counterparts lacking transcriptional ability is crucial for genomic stability. As, allelic conterparts of a-satellite DNA gaff (DNA associated with chromosomal segregation) replicate synchronously in cells showing an accurate segregation of chromosomes and asynchronously in cells displaying losses and gains of whole chromosomes (Litmanovich et al 1998).

It has now been surprisingly found that in peripheral blood lymphocytes of individuals stricken with solid tumors, genes and even non-coding DNA sequences changed the level of synchrony in replication timing of allelic counterparts. Allelic sequences replicating synchronously in cells of healthy subjects revealed a startling rise in asynchrony, while sequences replicating asynchronously in healthy subjects tended to replicate more synchronously in cells of cancer-stricken individuals. The change in timing of replication of non-coding loci was found to be associated with losses and gains of chromosomes (aneuploidy) a feature characteristic for cancer.

Furthermore, the exposure to various agents that interfere with gene expression and/or chromatin conformation further differentiate between lymphocytes of cancer patients and those obtained from non-cancerous subjects, as each usually alters the replication mode of only one type of cells, either cancerous or healthy, leaving the other un-touched.

It has been also demonstrated that synchrony in replication timing of allelic sequences may be used for the detection of causing genomic instability (genotoxicity) associated with cancer initiation, when applied in-vivo as well as in-vitro.

Thus, the phenomenon of modification in the inherent mode of allelic replication in the presence and in the absence of various DNA and chromatin modifiers may be useful in early diagnosis and detection of cancer.

Similarly, this phenomenon may be used for the detection of drugs and various environmental agents leading to genotoxicity.

In peripheral blood lymphocytes of individuals stricken with solid tumors, genes as well as noncoding DNA sequences changed the level of synchrony in replication timing of allelic counterparts. DNA sequences replicating synchronously in cells of healthy subjects revealed a startling rise in asynchrony, while sequences replicating asynchronously in healthy subjects tended to replicate more synchronously in cells of cancer-stricken individuals. It would therefore be useful to develop a method for using this phenomenon in early diagnosis and detection of cancer.

It would therefore also be useful to establish that loss of fidelity in the inherent temporal order of DNA replication provides a common source for generating numerous genetic events required for establishing a malignant phenotype.

SUMMARY OF THE INVENTION

The invention is directed at a method for the detection of cancer, appraising the prognosis thereof, and/or risk therefor comprising the steps of:

a) obtaining essentially non-malignant cells from an individual;

b) determining the coordination between allelic counterparts of one or more loci in said cells. The cells are preferably subjected to a growth stimulus before step (b). Preferably, the cells are also subjected to drugs associated with gene expression and/or chromatin conformation before step (b). Also preferably, the cells are derived from a body tissue or body fluid. The body tissue is preferably bone marrow. The body fluid is preferably selected from blood, amniotic fluid, urine, and saliva. Preferably, the blood is peripheral blood. The cells are preferably lymphocytes.

The same method can be used for examine whether a drug and/or an environmental factor posses a genotoxic effect either applied in-vivo before step (a) or in-vitro before step (b).

The locus or loci are preferably expressed biallelically. Further preferably, the locus or loci are selected from tumor-associated genes. The tumor-associated genes are preferably selected from oncogenes, tumor suppressor genes, and transcription factors involved in translocations associated with blood tumors.

In another embodiment, the invention comprises a method as defined above wherein the locus or loci are expressed monoallelically. The monoallelically expressed locus or loci are preferably selected from imprinted loci, loci where one allele has been silenced, and loci on the X-chromosome in female individuals. The imprinted locus is preferably the Prader-Willi locus.

In another embodiment, the invention comprises a method as defined wherein the locus or loci are non-coding loci lacking transcriptional capability. The non-coding locus or loci are preferably selected from DNA sequences associated with chromosome segregation. The DNA is preferably satellite DNA.

In a more preferred embodiment of the invention, the locus or loci are selected from among HER2, CMYC, TP53, RB1, 21q22, GABRB3, SNRPN, D15S10, D22S75, DSTS WI-941, alpha, II and III satellites for all chromosomes.

The synchrony is preferably determined by fluorescence in situ hybridization.

The method of the invention is preferably a method wherein a change in synchrony indicative of cancer, the prognosis of cancer, or the risk therefor, is detected. The change in synchrony is preferably between about 3% and about 55%.

In one embodiment of the method of the invention, the change in synchrony is an increase in asynchrony. The increase is preferably between about 25% and about 30%. More preferably, the number of SD cells as determined by fluorescence in situ hybridization is increased by about 25% to about 30%.

In a further embodiment of the method of the invention, the change in synchrony is a decrease in asynchrony. The decrease is preferably about 15%.

In another embodiment of the method of the invention, synchrony is measured by fluorescence in situ hybridization, using a probe targeted to a biallelically expressed gene, in cells derived from peripheral blood, and wherein an increase in asynchrony of about 15% to about 35% is indicative of cancer, the prognosis thereof, or risk therefor.

In another embodiment of the method of the invention, synchrony is measured by fluorescence in situ hybridization, using a probe targeted to a monoallelically expressed gene, in cells derived from peripheral blood, and wherein a decrease in asynchrony of about 15% to about 25% is indicative of cancer, the prognosis thereof, or risk therefor.

Further, according to the present invention, there is provided a method for the detection of cancer and cancer risk by analyzing the replication status of a locus or loci within isolated cells whereby an altered replication status corresponds to cancer or cancer risk. Also provided is a method of determining the replication status of various DNA sequences by assaying isolated cells following in-vivo or in-vitro exposure to various drugs or environmental agents to determine genotxicity if any of the applied agents. A diagnostic test for detecting cancer or the risk of cancer having an allelic replication viewing device for viewing the mode of allelic replication of a DNA entity, a standardized table of replication patterns and an analyzer to determine an altered pattern of replication, whereby such altered pattern is a cancer characteristic is also provided. There is also provided a method for differentiating between hematological and solid malignancies by analysing the replication status of mono allelic expressed genes and analyzing the replication status of the sequences to distinguish between hematological and solid malignancies.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
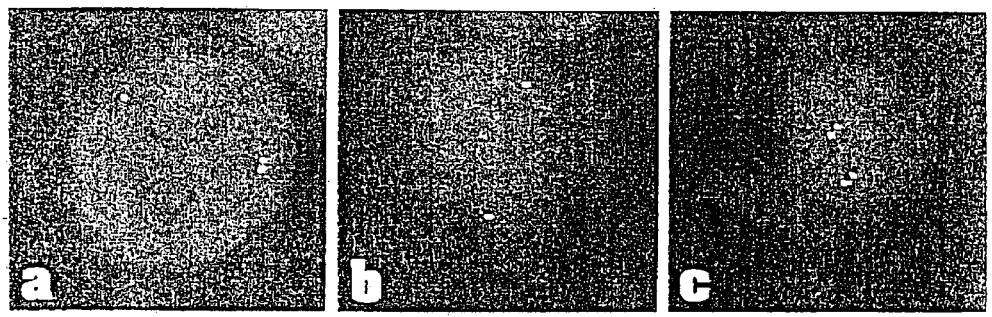
FIG. 1 shows (a) a cell with one "singlet" and one "doublet" hybridization signal (SD cell) representing S-phase cells where only one of the allelic sequences has replicated; (b) a cell with two "singlets" (SS cell) representing cells in which both sequences are unreplicated; and (c) a cell with two "doublets" (DD cell) representing cells in which both sequences have replicated.

This invention relates to methods for the detection of cancer risk and cancer. The methods require analysis of the coordination between allelic counterparts in various characters associated with gene expression and/or chromatin conformation preferably replication control within cells of an animal, including a human animal. The practice of the invention involves methods known in the art of molecular biology and cytogenetics.

A number of methods of the art of molecular biology are not detailed herein, as they are well known to the person of skill in the art. Such methods include PCR cloning, transformation of bacterial and yeast cells, transfection of mammalian cells, and the like. Textbooks describing such methods are e.g., Sanbrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, John Wiley & Sons, Inc. 1988, and Short Protocols in Molecular Biology, by F. M. Ausubel et al. (eds.) $3^{rd}$ ed. John Wiley & Sons; ISBN: 0471137812, 1995. These publications are incorporated herein in their entirety by reference. In particular, the obtention of cells from the body of an animal, and the analysis thereof by fluorescent in situ hybridization, has been described in many articles and textbooks, see e.g. the publication by the inventors Amiel et al., Genes, Chromosomes and Cancer 22, 225–231, 1998, Yeshaya et al. Hum. Genet.105,86–97, 1999 and references therein, included in their entirety by reference.

The association of asynchrony in certain cells of certain cancers has been disclosed by the present inventors, see Amiel et al., Genes, Chromosomes and Cancer 22, 225–231, 1998 and Litmanovich et al. Cytogenet. Cell Genet. 81,23–35, 1998 The teaching of said Amiel et al., regarding inter alia the said association of asynchrony with cancer, and the methods disclosed and suggested therein for the detection of changes in synchrony, are incorporated herein in their entirety by reference, The following terms are meant herein to be understood as defined below:

synchrony, the phenomenon where the two alleles of a gene are replicating synchronously;

asynchrony, the phenomenon where the two alleles of a gene are replicating asynchronously;

locus, a defined location on a chromosome;

gene, a defined locus on a chromosome comprising regulatory sequences which regulate expression or engage in the expression of expressed sequences;

non-coding DNA, a defined locus on a chromosome comprising sequences lacking transcriptional capability;

DD cell, a cell which when analyzed by the FISH technique displays two doublet spots of hybridization signal for a given locus, indicating that both alleles have replicated;

SD cell, a cell which when analyzed by the FISH technique displays one doublet and one singlet spot of hybridization signal for a given locus, indicating that one alleles has replicated, but the other has not. The appearance of SD cells is an indication for asynchrony;

SS cell, a cell which when analyzed by the FISH technique displays two singlet spots of hybridization signal for a given locus, indicating that none of the alleles has replicated;

biallelic expression, expression state of a gene wherein both alleles are expressed about equally;

monoallelic expression, expression state of a gene wherein one allele is expressed at a significantly lower level compared to the other, for instance, when the allele is silent;

non-malignant cell, a cell that is not a cancer cell. The cell is usually a healthy cell obtained from an organism which may or may not suffer from cancer. The cell may be not healthy in other respects, e.g., it can be a cell infected with an infectious agent. The above definition merely requires that the cell not be a cancer cell.

The invention is directed at a method for the prognosis and detection of cancer. The method comprises obtaining non-cancerous cells from an individual and determining the synchrony of replication of one or more loci in the cells, in the presence or the absence of various agents added for further differentiation between cancer and non-cancer subjects.

The preferred method of determining synchrony in the method of the invention is fluorescence in situ hybridization (FISH). The FISH replication assay is relatively simple and fast, and in contrast to the classical replication timing methods avoids the incorporaton of BrdU or other agents that can interfere with DNA replication; selects S-phase cells with no need for cell sorting or cell synchronization; and allows identification of individual alleles within a single cell with no need to rely on allelic polymorphism or methylation level differences between two allelic counterparts (Selig et al. 1992; Boggs and Chinault 1997).

The FISH assay relies on replication dependent chromatin conformation. Accordingly, the replication status of a locus is inferred from the shape of the hybridization signal obtained at interphase, following FISH with a locus-specific probe. Prior to replication, each identified DNA sequence shows a single dot like hybridization signal ("singlet"; S), while at the end of replication it assumes a doubled bipartite structure ("doublet"; D) (Selig et al. 1992; Mukherjee et al. 1992; Boggs and Chinault 1997). Cells with one "singlet" and one "doublet" represent S-phase cells (designated SD cells) in which only one of the allelic sequences has replicated. Cells with two "singlets" (SS cells) represent those in which both sequences are unreplicated, and cells with two "doublets" (DD cells) represent those in which both sequences have replicated, see e.g., FIG. 1 in Amiel et al., Gen. Chrom. Cancer 22, 225–31, 1998, incorporated herein entirely by reference. In an unsynchronized population of replicating cells the frequency of cells at a given stage expresses the relative duration of that stage. Hence, the frequency of SD cells, out of the total population of cells with two hybridization signals, correlates with the time interval (at S-phase) during which the two allelic counterparts differ in their replication status, i.e., there is an early (identified by a "doublet") and a late replicating allele (recognized by a "singlet"). Similarly, the frequency of DD cells reveals the relative time interval at interphase during which the two counterparts are replicated (part of S-phase, and the whole $G_2$ phase), while the frequency of SS cells correlates with the time interval during which the two counterparts are unreplicated ($G_0$, $G_1$ and part of S-phase). Thus, a high frequency of SD cells shows asynchrony in replication timing of the two allelic counterparts; high frequency of DD cells indicates early replication of the identified locus; and high frequency of SS cells points to late replication.

The invention also relates to a method wherein the cells are subjected to a growth stimulus before being assayed for said determination of synchrony. The invention also relates to a method wherin the cells are subjected to DNA and chromatin modifier components that differentiate further between cells derived from individuals suffering from cancer and non-cancerous ones.

The cells are preferably derived from blood, bone marrow, or amniotic fluid. More preferably, the cells are derived from blood. Also preferably, the cells are lymphocytes. More preferably, the cells are blood lymphocytes.

Any type of cancer can be detected using the method of the invention. Preferably, the cancer is a solid tumor. More preferably, the tumor is renal cell carcinoma, prostate carcinoma or breast cancer.

The loci are selected from synchronous and asynchronous loci. More preferably, the synchronous loci are selected from tumor-associated genes and non-coding loci associated with chromosomal segregation. The asynchronous loci are expressed non-concomitantly. More preferably, the asynchronous loci are selected from imprinted loci, and loci on the X-chromosome in female individuals. Preferably, the loci are selected from the group of tumor-associated genes, satellite DNA and imprinted loci. The tumor-associated genes are preferably selected from oncogenes, tumor suppressor genes, and transcription factors. The imprinted locus is preferably selected from the Prader-Willi syndrome locus. The non-coding loci are preferably selected from centromeric specific (satellited loci) Also preferably, the loci are selected from among HER2, CMYC, TP53, RB1, 21q22, GABRB3, SNRPN, D15S10, D22S75, and DSTS WI-941 and alpha, II and III satellites for all chromosomes.

The synchrony is preferably determined by fluorescence in situ hybridization.

The increase in asynchrony indicative of cancer or risk therefor is preferably an increase of between about 3% and about 55%, more preferably between about 25% and about 30%, in the number of SD cells when measure by fluorescence in situ hybridization.

The decrease in asynchrony indicative of cancer or risk therefore is preferably a decrease of between about 3% and about 50%, more preferably about 15%, in the number of SD cells when measure by fluorescence in situ hybridization.

FISH is utilized to study the replication pattern of three loci (TP53, D21S55 and GABRB3) in peripheral blood lymphocytes of ten unrelated cancer patients suffering from a solid tumor (nonfamilial renal cell carcinoma; Linehan et al. 1995), and in peripheral blood lymphocytes of ten healthy subjects. Of the three tested loci, TP53 is a tumor suppressor gene whose inactivation is associated with different types of malignant diseases (reviewed in Kinzler and Vogelstein 1995; Levine 1997). The D21S55 is located at the 21q22 chromosomal region, which carries a gene (AML1) encoding an essential transcription factor (Levanon et al. 1994). This region has been implicated (through several chromosomal translocations and deletions) in various blood tumors (Look 1998). GABRB3, which identifies the γ-aminobutyric acid receptor subunit β3 gene, is located within the Prader-Willi syndrome region (an extensively studied domain in man), and has been found to replicate early the paternal allele, leaving the maternal one to replicate late (Knoll et al. 1994; LaSalle and Lalande 1995).

Using the FISH replication assay it was demonstrated that in peripheral blood lymphocytes derived from normal subjects the imprinted GABRB3 locus exhibited an allele-specific replication timing, while TP53 and D21S55 manifested a high level of synchrony in allelic replication timing. Those results: (i) agree well with previous information achieved also by FISH for the GABRB3 locus and other adjacent sequences within the Prader-Willi syndrome imprinted region (Knoll et al. 1994; LaSalle and Lalande 1995; Gunaratne et al. 1995), and (ii) are expected for TP53 and D21S55 two loci expressed in the common biallelic mode (Kitzberg et al. 1993).

The level of variation in replication timing of a given locus within the group of normal samples is considerably low, indicating that the results are reproducible and the FISH replication assay, as applied, can be used as a reliable assay to study temporal order of DNA replication.

Thus, it is demonstrated that in normal lymphocytes the D21S55 locus, which encompasses the transcription factor AML1, replicates much earlier than the TP53 locus, and that the early replicating allele of the GABRB3 locus initiates replication even earlier than the D21S55 alleles. Hence, relying on the association between early replication and transcription ability as mentioned above, one may assume that in normal lymphocytes both D21S55 alleles similar to the early replicating allele from the GABRB3 locus are expressed, while the TP53 alleles are silent similarly to the late replicating allele of the imprinted locus. This is supported by various lines of evidence indicating that TP53 is usually moderately expressed in normal cells, and becomes active only under stressful situations as a protective measure (Kinzler and Vogelstein 1995; Levine 1997).

Yet, in peripheral blood lymphocytes of cancer patients the replication pattern of the imprinted GABRB3 locus was altered; a relaxation in the imprinted pattern of replication was observed, resulting from a delay in replication timing of the early replicating allele, i.e., the active alelle, which at this locus happens to be the paternal one (Knoll et al. 1994; LaSalle and Lalande 1995). This observation is expected if one assumes that the delayed replication of the early replicating allele at the imprinted locus reflects a reduction in its transcriptional activity, a process leading to loss of imprinting (LOI), an epigenetic modification, known to occur in malignant cells. LOI results either from silencing of the normally active allele, as it is the case here (inferred from the replication pattern) or alternatively, from activation of the normally silent allele (reviewed in Feinberg 1998). Recently, LOI was reported to appear also in lymphocytes of a subgroup of patients suffering from colorectal cancer (Cui et al. 1998).

Interestingly, in lymphocytes of the cancer patients the replication mode of the two independent non-imprinted loci, TP53 and D21S55, was altered too; both loci changed their normal synchronized pattern of allelic-replication and each gave rise to an early and a late replicating allele. The temporal difference between allelic counterparts of TP53 and D21S55 in lymphocytes of cancer patients was similar to that normally observed for two alleles of an imprinted locus. In patients' lymphocytes the asynchronous pattern of allelic replication of TP53 as well as of D21S55 was achieved as a result from an advanced replication of a single allele which replicated earlier than its normal scheduled timing. However, while the replication timing of the second allele of TP53 (the normally late replicating locus) was not affected by the malignancy, that of D21S55 (the normally early replicating locus) was postponed. Whether the choice of one allele of TP53 and D21S55 loci to undergo early replication in the cancer-induced process is a random event, a parent-of-origin-dependent process, or some other preferential mechanism is yet unknown; neither it is known whether such stimulation is reversible in the lineage of a cell.

Whatever the mechanism is, the shift in the mode of replication of the biallelically expressed loci, TP53 and D21S55, to a replication mode characterizing monoallelically expressed loci, reflects a locus non-specific, allele-specific epigenetic alteration leading to functional hemizygosity of several developmentally-essential genes within a single cell. An allele-specific inactivation/activation (i)

increases many-fold the probability of shutting off a wild type allele, leaving the diploid cell to the "mercy" of an allele, lacking transcriptional ability; (ii) changes the cell phenotype by inactivating a dominant allele and enabling the expression of its recessive counterpart; and finally (iii) this mechanism alters cell functions which depend on two intact copies of a gene. All of these consequences are presumed to occur concurrently for a large number of genes within a single cell. Evidently, such an assumed mechanism offers an avenue for the second-hit in the Knudson two-hit model for cancer development (Knudson 1993), by uncovering deleterious recessive alleles of tumor suppressor genes which are occasionally present in a genome (acquired either through the germ line or by somatic mutations). Alternatively, it activates a single allele from a normally silent oncogene.

Moreover, if allele-specific replication indeed reflects allele specific expression, assumed on the basis of the tight association between allelic asynchronous replication and allele-specific expression, then from a functional point of view allele-specific replication is equivalent to loss of heterozygosity (LOH), an event which results from the physical loss of a small DNA segment, mitotic recombination, or gene conversion, known to accompany the development and establishment of cancer (Knudson 1993). However, the assumed event of allele-specific expression which is not associated with a physical loss of an allele but with a loss of function, achieved by epigenetic means, in contrast to LOH, retains the ability, to be reversible and plays a pivotal role in cancer progression and regression.

Whatever the meaning of the locus non-specific modification in replication timing observed in peripheral blood lymphocytes of cancer patients, the allelic mode of replication offers a potential application for the detection of cancer using a most simple cytogenetic assay.

Moreover, functional hemizygosity of a large number of regulatory genes involved in cell proliferation and differentiation accompanied by relaxation in imprinting of developmental essential genes, all occurring in a single cell, offers a solution for an old puzzling question (Loeb 1991; Jackson and Loeb, 1998): how does a single cell, even one predisposed to cancer, acquire the large number of mutations needed for its transformation into a cancer cell.

The fact that changes in synchrony are present cells obtained from amniotic fluid of fetuses afflicted with autosomal trisomies (Example 3 above, see also Amiel et al., Eur. J. Hum. Genet. 7, 223–230, 1999, incorporated herein by reference), further points to the use of the technique of the invention in the determination of a risk for cancer.

Autosomal trisomies vary in their symptoms among individuals. However, a common feature is the association of such trisomies with an increased likelihood of cancer, in various organs. Example 3 shows that it is possible to use amniocytes for the determination of increased cancer risk. The samples were obtained from amniotic fluid, which comprises cells derived from skin tissue of the foetus. These skins cells are non-malignant. In some cases, individuals afflicted with trisomy develop cancer in the fetal stage. These cancers are found in various organs of the fetus, but usually are not skin cancer. The method of the invention is therefore capable to detect cancer and to determine an increased risk for cancer, by using non-malignant cells derived from skin tissue.

The relaxing of replication and expression control in individuals with trisomy predisposes them for LOI and for expression of recessive genes. These events are believed to be involved in the etiology of cancer. The present invention therefore relates to a method of determining the risk of cancer in an individual which has not yet developed cancer.

The association between cancer risk and changes in synchrony is further demonstrated in the data of Example 2 herein. Significantly elevated levels of asynchrony in the Her2-Neu gene were found in individuals exposed to radiation known to cause cancer. In addition, the data of Example 5 shows that growth factor treatment results in increased cancer risk. As association of growth factors and cancer is actually documented in the case of human growth hormone.

Thus, the present invention provides, by the measurement of asynchrony, a method of identifying the risk for cancer. It is believed that, as has been demonstrated herein for cancer-afflicted individuals, this association also applied to other genes, including those genes in which a decrease in asynchrony, rather than an increase, can be detected. In general, it is believed that the method of identifying a risk of cancer requires determining a change in synchrony, but is not restricted to an increase in asynchrony.

In general, it is believed that the change in synchrony, as detailed herein, is a characteristic of deregulation of cell growth. The present invention shows that this characteristic applies to all cells of a body afflicted with cancer, regardless of whether they are actually afflicted with cancer or not. The present invention further shows that the phenomenon applies to cells of a body that has not developed cancer, but is at risk of doing so.

It is believed that a change in synchrony is associated with a general relaxation of regulation of DNA replication and expression. Therefore, methods of determining regulation of DNA replication and expression are useful in the detection and prognosis of cancer.

In further experiments, probes recognizing the HER2 locus (18q11.2–q12, Vysis 32-190003), the 21q22 locus (Vysis 32-190002), the MYC locus (8q24, Vysis 32-190006), the RB1 locus (14q14, Vysis 32-190001) and alpha, II and III satellites for all chromosomes were used.

The above selection of probes targeted to various loci shows that the method of the invention is not restricted to the use of cancer-associated genes and loci as probes. The probes used herein targeted to the Prader-Willi locus (D15S10 and GABRB3), and the probes targeted to the DiGeorge locus, are not known to be associated with cancer. Nevertheless, Example 4 below clearly shows that changes in synchrony in these loci are associated with cancer. Therefore, the association of the change in synchrony with cancer, is believed to be a general phenomenon, which is independent of the loci examined here. It is believed that a wide variety of loci can be targeted in the method of the invention, with equally suitable results.

It is further believed that in general, imprinted loci that show asynchrony in cells derived from healthy individuals, present lower levels of asynchrony in individuals that are afflicted with cancer or at risk of developing cancer.

Moreover, it is believed that in general, loci that are expressed biallelically or associated with chromosome segregation and that show synchrony in cells derived from healthy individuals, present asynchrony in cells derived from individuals afflicted with cancer or at risk of developing cancer.

Therefore, the method of the invention is useful in the detection of cancer in a mammal. The method of the invention is also capable of identifying a risk for development of cancer. It is believed that the method of the invention is useful in appraisal of the prognosis of cancer (see example describing the work of Mashevich et al. 2000). Thus, the extent of change in synchrony is believed to be greatest when the prognosis is unfavorable. On the other hand, the extent of change in synchrony is believed to be lower in cases with favorable prognosis. Accordingly, the method of the invention can also be used to monitor treatment of cancer. Effective treatment reduces the change in synchrony, so that the synchrony levels approach that expected from a healthy individual. Conversely, greater changes in synchrony indicate that the treatment fails and the cancer can become more malignant.

The present invention further provides a method and test for detecting cancer and the risk of cancer in patients by analyzing the patterns of behavior of alleles within isolated cells, such that an alteration in the pattern of coordination between allelic counterparts indicates a risk of cancer or the presence of cancer.

By the term "cells" as used herein, it is meant any cells which are found in a subject. These cells can include, but are not limited to, cells isolated from bodily fluids and tissues. The bodily fluid can include urine and saliva, while the tissue can include tumorigenic tissue and tissue surrounding a tumor. In the preferred embodiment the cells used with the present invention are peripheral blood cells.

The term "pattern of behavior" means patterns of homologous genetic material which are compared based on one or several of various criteria by means known in the art for achieving other results. Examples of various criteria are replication, expression, levels of methylation of DNA, conforrnation, and acetylation of homologous DNA sequences. Means known in the art for obtaining such data on the character of the homologous DNA are FISH, and molecular biology techniques anabling to follow replication methylation acetylation and expression of homologous DNA sequences.

By way of background, the greatest impediment to cancer diagnosis lies in the need to access the tumor directly. Moreover, in most cases of patients with a solid tumor, detection of the tumor is only achieved following invasive procedures. However, efforts to identify abnormalities in unaffected easily attained tissues, such as peripheral blood, of patients with solid tumors have been disappointing so far. For example, even the level of PSA in blood, which is largely used for the detection of prostate cancer, one of the most frequent tumors in men, provides a positive predictive value in only about 20–30% of cases, as to most of the other cancer blood markers used to date. Even in hematological malignancies the recognized cytogenetic markers are not frequent enough to provide over than 20% of predictive value.

The present invention provides a diagnostic test based on small aliquots of peripheral blood that identifies patients with various types of solid tumors such as prostate cancer, breast cancer and renal cell carcinoma as well as hematological malignancies with a positive predicted value of about 80% or above. The test offers a decisive advantage for cancer detection. It not only prevents invasive procedures that are hazardous, painful and costly, but also enables earlier detection, which is crucial for effective treatment, and possible cure, of cancer. Moreover, it provides a reliable tool for the detection of a minimal residual malignant disease following completion of the therapy course. The test is based on the mode of allelic replication viewed by modem molecular cytogenetic means using fluorescence in-situ hybridization (FISH; Boggs and Chinault, 1977). Other tests as are known to those of skill in the art can also be used for viewing the allelic replication.

Allelic replication occurs either synchronously or asynchronously, depending on the mode of expression of a given locus. Accordingly, two allelic counterparts of a locus, which is expressed in the expected Mendelian mode (bi-allelic expression), replicate synchronously, whereas allelic counterparts of a locus subjected to mono-allelic expression replicate asynchronously. Normally, mono-allelic expression occurs in loci subjected to imprinting, X-chromosome-inactivation or allelic exclusion (reviewed in Yeashaya et al 1999).

Evidence accumulating lately shows that malignant cells and possibly even cells prone to cancer disclose fidelity-loss in replication timing of alleles (Amiel et al 1998a, 1998b, 1999a, 1999b, 2000). Alteration in the inherent mode of allelic replication is not limited to the malignant tissues but also characterizes peripheral blood cells of patients stricken with various solid tumors. Using the FISH replication assay it was demonstrated that allelic counterparts of cancer-inducing genes, when present in blood lymphocytes of patients suffering from renal cell carcinoma, prostate cancer and breast cancer, display typical changes in their replication mode. Similar alterations in the temporal order of replication were also observed in peripheral blood lymphocytes of patients suffering from blood malignancies such as various types of leukemia and lymphoma (Amiel et al 1998a). The cancer-induced change in the temporal order of replication was also expressed by non-coding loci. Peripheral blood lymphocytes of females suffering from hereditary ovarian cancer displayed gross modifications in the temporal order of replication of homologous counterparts of DNA loci associated with human centromeres (Litmanovitch et al 1998). The abnormal replication pattern of centromeric homologous arrays is associated with chromosome male-segregation leading to losses and gains of whole chromosomes (aneuploidy), an archetypal phenomenon accompanying oncogenesis (Litmanovitch et al 1998).

Moreover, the exposure to various agents which interfere with gene expression and/or chromatin conformation further differentiate between lymphocytes of cancer patients and those obtained from non-cancerous subjects, as each usually alters the replication mode of only one type of cells, either cancerous or healthy, leaving the other untouched.

Individuals recuperating from cancer, such as hematological patients following successful stem cell transplantation, display normal patterns of allelic replication in coding as well as in non-coding DNA sequences, that is, similar to those shown by non-cancerous subjects.

Using FISH it was demonstrated that allelic counterparts of bi-allelically expressed genes (TP53, RB1, HER2, CMYC and AML1) known to replicate highly synchronously in peripheral blood cells obtained from non-cancerous subjects, when present in blood lymphocytes of patients suffering from various types of solid tumors (prostate cancer, breast cancer and renal cell carcinoma) and hematological malignancies replicate highly asynchronously similarly to mono-allelically expressed genes.

The FISH replication assay relies on replication dependent chromatin conformation of the identified loci. Accordingly, "replication status" as used throughout the application is defined as follows: an unreplicated allele assumes a single dot-like (singlet; S) fluorescence signal. While, a replicated one gives rise to a signal composed of two closely associated dotes (doublet; D). Thus, a gene replicating mono-allelically, following FISH reveals a high frequency of cells with two alleles differing in their replication status, a replicated and an unreplicated allele (SD cells). In contrast, alleles replicating synchronously display very low frequency of SD cells. The frequency of SD in PHA-stimulated lymphocyte is the parameter used in the method to differentiate between a cancer patient and a control individual (for more details please see the attached manuscript of Dotan et al 2000).

Using the FISH replication assay applied to three cancer-inducing genes (TP53, RB1 and AML1) as well as to two non-coding, centromere-associated DNA sequences (satellited sequences specific for chromosomes 15 and 17), all lost their inherent bi-allelic mode of replication when present in blood cells of hematological patients. All five loci tested when present in the. cancerous genome displayed the archetypal allele-specific mode of replication coupled with an increased level of chromosome losses and gains for all tested chromosomes (chromosome 13, 15, 17 and 21).

The mechanism underlying the cancer-induced allele-specific replication is associated with hypermethylationan epigenetic modification contributing to the inactivation of tumor suppressor genes during cancer progression (Baylin and Herman, 2000), as it was reversed to the normal, in all five loci tested, when a typical demethylating agent (5-azacytidine; Haaf, 1995) was applied. There are also evidence that the mechanism relies on acetylation and deacetylation cycles.

Moreover, these altered pattern of replication characteristic of blood cells of cancer patients is not limited to expressed genes, as it is also characteristic of unexpressed DNA entities responsible for the segregation of genetic material. These abnormal replication patterns are linked with losses and gains of whole chromosomes (aneuploidy), a cancer characteristic phenomenon that is easily detected using our assay.

In the laboratory the FISH based replication essay was refined to include the number of signals per cell (indicative of aneuploidy level), shape and conformation of the signals (both two and three dimensional) for the replication status determination.

In addition, as the test relies on changes in three dimensional DNA conformation, it was demonstrated that chemicals which are chromatin modifiers (s.a. 5-azacytidine, Trichostatin A; Sodium Butirate) attenuate the replication pattern presented in cells derived from cancer patients towards the normal, while not affecting the pattern observed in normal genomes. The difference in the effect of the chemical modifiers on the cultured cells can be used to differentiate between normal and cancerous individuals.

The method of the present application can also be used for the detection of agents causing genomic destabilization associated with losses and gains of chromosomes.

The above discussion provides a factual basis for the use of method so and test for detecting cancer and cancer risk. The methods used with and the utility of the present invention can be shown by the following non-limiting examples and accompanying figures.

Materials and Methods

Sample description. For Example 1, samples of peripheral blood derived from ten normal males with no history of familial cancer (samples 1–10) and from ten male patients suffering from nonhereditary renal cell carcinoma (samples 11–20) were analyzed. The age of the normal donors ranged between 47–87 years and that of cancer patients between 47–79 years, with mean and standard errors values of 67.5±4.5 and 62.4±3.5 years, respectively. Patient's samples were obtained at first diagnosis, prior to any clinical (physical or chemical) treatment, and cytogenetically analyzed after verification of the diagnosis by tissue assessment. For the other examples, subjects were selected and data analyzed similarly, unless specifically stated.

PHA-stimulated lymphocytes (unsynchronized population of replicating cells). Aliquots from each blood sample were incubated for short term culture and prepared as described previously (Litmanovitch et al.1998).

Bone Marrow Samples

Bone marrow was obtained and cultured as described (Amiel et al., Genes Chrom. Cancer 22, 225–231, 1998). Briefly, Aspirates from bone marrow cells were obtained and cultured at about $2 \times 10^6$ cells/ml for 24 or 48 hours in RPMI 1604, 20% FCS, at 37° C. in 5% $CO_2$. Colcemid was then added to 0.05 $\mu$g/ml final concentration. After twelve minutes, cells were treated with 0.075M KCI at 37° C. for twenty minutes, washed five times with a fresh cold 3:1 methanol:acetic acid solution. Cell suspensions were stored at 4° C. until used.

Probes. Commercial DNA probes (Oncor or Vysis), each highly specific for a different chromosome region, were used: (i) TP53 probe (biotin labeled) mapped to 17p13.1; (ii) chromosome 21-specific DNA probe (digoxigenin labeled), recognizing the 21q22 (D21S55, Vysis Inc. Downers Grove, Ill., USA, Cat. No. 32-190002) region; and (iii) the Prader-Willi/Angelman syndrome probe (digoxigenin labeled), recognizing the imprinted GABRB3 locus, mapped to 15q11–q13. Another probe targeted to the Prader-Willi locus was D15S10. In further experiments, probes recognizing the HER2 locus (17q11.2–12, Vysis 32-190003), the chromosome 21-specific probe recognizing the 21q22 locus (Vysis 32-190002), the MYC locus (8q24, Vysis 32-190006), the RB1 locus (13q14, Vysis 32-190001), the 22q11.2 locus (D22 S75, DiGeorge, Vysis 32-191028), the 22q13 locus (STS WI-94, near DiGeorge) were used, as well as alpha, II and III satellites for all chromosomes.

In-situ hybriidization and signal detection. FISH was carried out according to the protocols recommended by the manuacturer (Oncor). Slides were stored at −20° C. until analyzed on an Olympus BH2 fluorescent microscope fitted with appropriate filter combinations.

Signal scoring. One hundred interphase cells with two hybridization signals are usually examined from each sample for each locus under completely blinded conditions by one or more individuals. The difference between values of the same case obtained by two different persons is usually similar to that obtained by the same person for two different samples of a given group analyzed by a given probe.

EXAMPLE 1

Levels of Synchrony in Replication Timing of Allelic Counterparts—Expressed by the Frequency of SD. Cells As detailed hereinabove, the FISH assay relies on replication-dependent chromatin confornation. Accordingly, the replication status of a locus is inferred from the shape of the hybridization signal obtained at interphase, following FISH with a locus-specific probe. Prior to replication, each identified DNA sequence shows a single dot like hybridization signal ("singlet"; S), while at the end of replication it assumes a doubled bipartite structure ("doublet"; D) (Selig et al. 1992; Mukherjee et al. 1992; Boggs and Chinault 1997). Cells with one "singlet" and one "doublet" represent S-phase cells (designated SD cells) in which only one of the allelic sequences has replicated. Cells with two "singlets" (SS cells) represent those in which both sequences are unreplicated, and cells with two "doublets" (DD cells) represent those in which both sequences have replicated (FIG. 1). In an unsynchronized population of replicating cells the frequency of cells at a given stage expresses the relative duration of that stage. Hence, the frequency of SD cells, out of the total population of cells with two hybridization signals, correlates with the time interval (at S-phase) during which the two allelic counterparts differ in their replication status, i.e., there is an early (identified by a "doublet") and a late replicating allele (recognized by a "singlet"). Similarly, the frequency of DD cells reveals the relative time interval at interphase during which the two counterparts are replicated (part of S-phase, and the whole $G_2$ phase), while the frequency of SS cells correlates with the time interval during which the two counterparts are unreplicated ($G_0$, $G_1$ and part of S-phase). Thus, a high frequency of SD cells shows asynchrony in replication timing of the two allelic counterparts; high frequency of DD cells indicates early replication of the identified locus; and high frequency of SS cells points to late replication.

Figure 2:
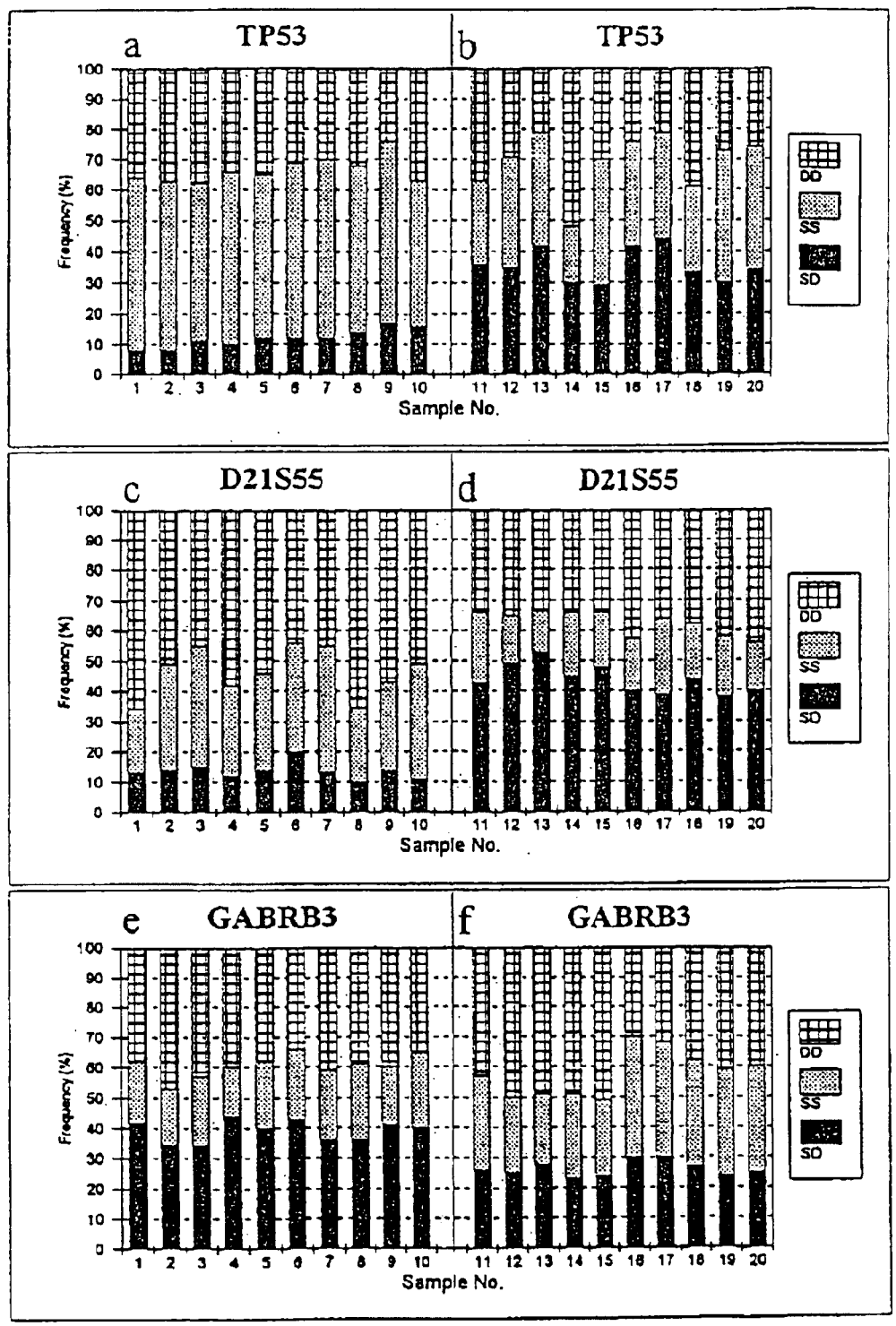
FIG. 2 shows the frequency (%) of SD, DD and SS cells of two biallelically expressed loci (TP53 and D21S55) and a momoallelically expressed locus (GABRB3) at interphase of PHA-stimulated lymphocytes from ten normal subjects (samples 1–10; frames a, c and e) and ten patients suffering from renal cell carcinoma (samples 11–20; frames b, d and f.

FIG. 2 shows the frequency (%) of SD, DD and SS cells at interphase of PHA-stimulated lymphocytes from ten normal subjects (samples 1–10; frames a, c and e) and ten patients suffering from renal cell carcinoma (samples 11–20; frames b, d and f), following FISH with a locus-specific probe identifying the indicated locus. One hundred cells with two hybridization signals were examined from each sample for each locus; the mean frequency values for each sample for each locus are presented in Table 1. The table shows the significance of the differences between the various loci in the frequency of cells with two allelic sequences: (i) differing in their replication status (SD cells); (ii) at the same status, both prior to replication (SS cells); and (iii) at the same status, both post replication (DD cells). Table 1a shows results from samples of normal subjects (samples 1–10) and Table 1b shows results samples of cancer patients (samples 11–20). The mean (M) and the standard error (SE) frequency (%) value of each locus for each group of samples are also give; two tailed student's t-test was used for the various comparison and P values of 1% or less were considered statistically significant.

frequency values of 35.5±1.7% for TP53 and 43.9±1.6% for D21S55 (FIGS. 2b and 2d); these values differed significantly (P<0.001) from the corresponding values obtained in samples of normal individuals (Table 2a). (II) In contrast to TP53 and D21S55, the GABRB3 locus in patients' samples showed a significant (P<0.001) decrease in the level of asynchrony compared to normal samples (mean frequency value of SD cells 26.2±0.8% vs. 39.6±1.2%, respectively; FIGS. 2e and 2f; Table 2a), indicating a significant relaxation in the imprinted pattern of GABRB3 replication. In fact, comparing the three loci in the same cell samples of cancer patients (FIGS. 2b, 2d and 2f, the level of asynchrony in replication timing of the GABRB3 alleles was even lower (P<0.001) than the levels exhibited by TP53 and D21S55 alleles (Table 1b).

Table 2 shows the significance of the differences of the designated loci between samples of normal subjects (samples 1–10) and cancer patients (samples 11–20) in the frequency of cells with two allelic sequences of a given replication status. Table 2A shows these differences in cells SD cells, Table 2B shows these differences in SS cells, and Table 2C shows these differences in DD cells. The mean (M) and the standard error (SE) frequency (%) value of each locus for each group of samples are also given. Two tailed student'st-test was used to compare between the normal and the patients' samples and P values of 1% or less were considered statistically significant.

TABLE 1

|  | SD | | | SS | | | DD | |
|---|---|---|---|---|---|---|---|---|
| a. Normal subjects (samples 1–10) | | | | | | | | |
|  | D21S55<br>M = 13.6<br>SE =± 0.9 | GABRB3<br>M = 39.0<br>SE =± 1.2 |  | D21S55<br>M = 32.7<br>SE =± 2.2 | GABRB3<br>M = 21.5<br>SE =± 0.9 |  | D21S55<br>M = 53.7<br>SE =± 2.6 | GABRB3<br>M = 39.5<br>SE =± 1.2 |
| TP53<br>M = 12.0<br>SE =± 1.0 | $t_{18}$ = 1.182<br>P > 0.10 | $t_{18}$ = 16.960<br>P < 0.001 | TP53<br>M = 54.7<br>SE =± 1.2 | $t_{18}$ = 8.503<br>P < 0.001 | $t_{18}$ = 10.481<br>P < 0.001 | TP53<br>M = 33.4<br>SE =± 1.4 | $t_{18}$ = 6.642<br>P < 0.001 | $t_{18}$ = 3.218<br>P < 0.01 |
| D21S55<br>M = 13.6<br>SE =± 0.9 | — | $t_{18}$ = 16.597<br>P < 0.001 | D21S55<br>M = 32.7<br>SE =± 2.2 | — | $t_{18}$ = 4.532<br>P < 0.001 | D21S55<br>M = 53.7<br>SE =± 2.6 | — | $t_{18}$ = 4.767<br>P < 0.001 |
| b. Cancer patients (samples 11–20) | | | | | | | | |
|  | D21S55<br>M = 43.9<br>SE =± 1.6 | GABRB3<br>M = 26.2<br>SE =± 0.8 |  | D21S55<br>M = 18.8<br>SE =± 1.1 | GABRB3<br>M = 31.5<br>SE =± 1.9 |  | D21S55<br>M = 37.3<br>SE =± 1.3 | GABRB3<br>M = 42.3<br>SE =± 2.4 |
| TP53<br>M = 35.5<br>SE =± 1.7 | $t_{18}$ = 3.431<br>P < 0.01 | $t_{18}$ = 4.649<br>P < 0.001 | TP53<br>M = 33.9<br>SE =± 2.4 | $t_{18}$ = 5.429<br>P < 0.001 | $t_{18}$ = 0.744<br>P > 0.20 | TP53<br>M = 30.6<br>SE =± 3.0 | $t_{18}$ = 1.914<br>P > 0.05 | $t_{18}$ = 2.874<br>P > 0.01 |
| D21S55<br>M = 43.9<br>SE =± 1.6 | — | $t_{18}$ = 10.776<br>P < 0.001 | D21S55<br>M = 18.8<br>SE =± 1.1 | — | $t_{18}$ = 5.537<br>P < 0.001 | D21S55<br>M = 37.3<br>SE =± 1.3 | — | $t_{18}$ = 1.744<br>P > 0.10 |

Following FISH with the probe identifying the TP53 locus, the frequency of SD cells in samples of normal individuals (samples 1–10) was low (mean of 12.0±1.0%). A similar (P>0.10) value for the frequency of SD cells was obtained with the probe for the D21S55 region (mean of 13.6±0.9%; FIGS. 2a and 2c; Table 1a). In contrast, following hybridization with a probe identifying an imprinted region, the GABRB3 probe, the same samples showed a significantly higher (P<0.001) frequency of SD cells (means of 39.0±1.2%; FIG. 2e; Table 1a). Evidently, in normal samples allelic counterparts of TP53 and D21S55 loci replicate highly synchronously, whereas GABRB3 alleles replicate asynchronously.

In samples derived from cancer patients (samples 11–20), however, the three loci showed an entirely different pattern of replication: (I) TP53 and D21S55 loci replicated highly asynchronously, showing high levels of SD cells with mean

TABLE 2

| A. SD | | | |
|---|---|---|---|
|  | Normal<br>TP53 | Normal<br>D21S55 | Normal<br>GABRB3 |
|  | M = 12.0<br>SE = ±1.0 | M = 13.6<br>SE = ±0.9 | M = 39.0<br>SE = ±1.2 |
| Patients | | | |
| TP53<br>M = 35.5<br>SE = ±1.7 | $t_{18}$ =<br>11.298<br>P < 0.001 | $t_{18}$ =<br>10.770<br>P < 0.001 | $t_{18}$ =<br>1.590<br>P > 0.10 |
| D21S55 | $t_{18}$ = | $t_{18}$ = | $t_{18}$ = |

TABLE 2-continued

| | | | |
|---|---|---|---|
| M = 43.9 | 16.606 | 16.201 | 2.388 |
| SE = ±1.6 | P < 0.001 | P < 0.001 | P > 0.02 |
| GABRB3 | $t_{18}$ = | $t_{18}$ = | $t_{18}$ = |
| M = 26.2 | 10.894 | 10.265 | 8.595 |
| SE = ±0.8 | P < 0.001 | P < 0.001 | P < 0.001 |

B. SS

| | Normal TP53 | Normal D21S55 | Normal GABRB3 |
|---|---|---|---|
| | M = 54.7 | M = 32.7 | M = 21.5 |
| | SE = ±1.2 | SE = ±2.2 | SE = ±1.2 |
| Patients | | | |
| TP53 | $t_{18}$ = | $t_{18}$ = | $t_{18}$ = |
| M = 33.9 | 7.371 | 0.352 | 4.566 |
| SE = ±2.4 | P < 0.001 | P > 0.50 | P < 0.001 |
| D21S55 | $t_{18}$ = | $t_{18}$ = | $t_{18}$ = |
| M = 18.8 | 21.318 | 5.466 | 1.801 |
| SE = ±1.1 | P < 0.001 | P < 0.001 | P > 0.05 |
| GABRB3 | $t_{18}$ = | $t_{18}$ = | $t_{18}$ = |
| M = 31.5 | 9.902 | 0.397 | 4.517 |
| SE = ±1.9 | P < 0.001 | P > 0.50 | P < 0.001 |

C. DD

| | Normal TP53 | Normal D21S55 | Normal GABRB3 |
|---|---|---|---|
| | M = 33.4 | M = 53.7 | M = 39.5 |
| | SE = ±1.4 | SE = ±2.6 | SE = ±1.2 |
| Patients | | | |
| TP53 | $t_{18}$ = | $t_{18}$ = | $t_{18}$ = |
| M = 30.6 | 0.797 | 5.504 | 2.584 |
| SE = ±3.0 | P > 0.20 | P < 0.001 | P > 0.01 |
| D21S55 | $t_{18}$ = | $t_{18}$ = | $t_{18}$ = |
| M = 37.3 | 1.954 | 5.389 | 1.174 |
| SE = ±1.3 | P > 0.05 | P < 0.001 | P > 0.10 |
| GABRB3 | $t_{18}$ = | $t_{18}$ = | $t_{18}$ = |
| M = 42.3 | 3.089 | 3.093 | 1.000 |
| SE = ±2.4 | P < 0.01 | P < 0.01 | P > 0.10 |

In addition, in samples of cancer patients the TP53 and D21S55 loci revealed similar (P>0.10 and P>0.02, respectively) frequencies of SD cells to that shown by the imprinted locus in the normal samples (FIGS. 2b, 2d and 2e; Table 2a). Yet, the GABRB3 locus, though exhibiting a significant decrease in the SD frequency in the patient samples compared to the normal ones, the SD frequency in patient samples was still significantly higher (P<0.001) than that observed for TP53 and D21S55 in normal samples (FIGS. 2a, 2c and 2f; Table 2a).

The decrease in the frequency of SD cells of GABRB3 in the patients sample did not result from a decrease in the number of S-phase cells in those samples. This is mostly evident from the large frequency of SD cells obtained with TP53 and D21S55 in the very same samples. Similarly, the increase of SD cells of TP53 and D21S55 loci in the cancer samples did not emerge from an increase in S-phase cells in these samples, since the same frequency of SD cells were present in normal samples for the imprinted GABRB3 locus.

Initiation and Termination Timing of Allelic Replication—Expressed by the Frequency of SS and DD Cells, Respectively In cells of normal individuals, both alleles of D21S55 initiate and complete their replication much earlier than do the TP53 partners. The earlier replication of the D21S55 alleles compared to TP53 alleles is evident from the significantly (P<0.001) lower frequency of SS cells and the significantly (P<0.001) higher frequency of DD cells following FISH with the D21S55 probe, compared to the corresponding values obtained following hybridization with the TP53 probe in the same cells (FIGS. 2a and 2c; Table 1a).

In contrast to normal cells, those derived from cancer patients showed no significant (P>0.05) temporal differences between D21S55 and TP53 loci in completion of allelic replication, expressed in the similar frequency of DD cells (FIGS. 2b and 2d; Table 1b), indicating that the late replicating allele of both loci replicated at the same time. On the other hand, in cells derived from the cancer patients the early replicating D21S55 allele replicated prior to the early replicating allele of the TP53 locus, inferred from the lower frequency of SS cells following replication with D21S55 compared to that obtained with TP53 (FIGS. 2b and 2d; Table 1b).

Regarding the GABRB3 region in normal cells, it appears from the frequency of DD cells that the late replicating allele at this locus completes replication after the D21S55 alleles and somewhat prior to the TP53 ones (FIGS. 2a, 2c and 2e; Table 1a). However, based on the frequency of SS cells, the early replicating allele of the GABRB3 locus in normal cells initiates its replication very early; earlier than do the TP53 alleles even earlier than the D21S55 pair (FIGS. 2a, 2c and 2e; Table 1a).

As inferred from the similar frequency of DD cells in normal subjects is and in cancer patients, almost no changes (P>0.10) occurred in the termination time of replication in the late replicating GABRB3 allele (FIGS. 2e and 2f; Table 2c). However, the higher frequency of SS cells in patients+ samples compared to normal ones (P<0.001) indicates that the early replicating GABRB3 allele in the patients' cells delays its replication timing compared to the early GABRB3 allele in normal cells (FIGS. 2e and 2f; Table 2b). Thus, the cancer status affects the early replicating GABRB3 allele but not the late one.

In a similar manner as detailed above, prostate cancer was detected using the method of the invention. A significant increase in asynchrony was detected in peripheral blood cells in individuals with prostate cancer. In contrast, individuals having enlarged prostate, but not suffering from cancer, did not show increased asynchrony levels.

These data suggest that the method of the invention is suitable for detection of a variety of cancers, independent of the type of cancer detected.

EXAMPLE 2

Peripheral blood cells were obtained from ten individuals exposed to various levels of radiation known to increase the risk for cancer. As a control, peripheral blood cells were obtained from ten individuals at the same workplace, but having not been exposed to the radiation.

The obtention of cells and the determination of synchrony by FISH was carried out as described above in Example 1.

Figure 3:
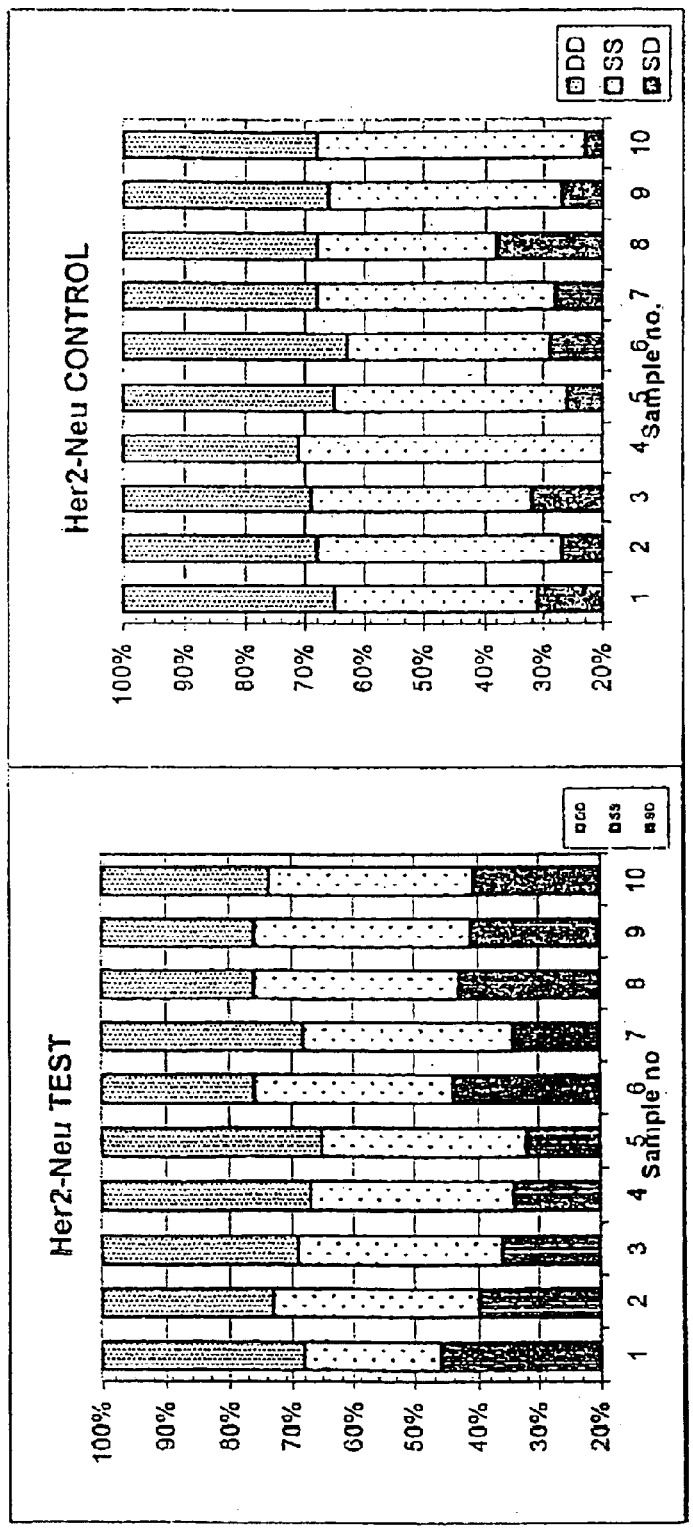
FIG. 3 shows percentage of SD cells in lyphocyte samples of individuals occupationally exposed to irradiation increasing risk for cancer (FIG. 3a), as compared to samples of control individuals working in the same place but not exposed to the irradiation (FIG. 3b). The probe used was HER2.

FIG. 3, left side, shows that the mean frequency of SD cells in samples derived from blood of individuals exposed to cancer-causing radiation is about 40%. In contrast, when samples are taken from individuals in the same workplace, but known not to have been exposed to irradiation, the frequency of SD cells is significantly lower (about 25%, FIG. 3, right side). These data show that exposure to irradiation, which is known to raise the likelihood of developing cancer in the exposed individual, results in elevated levels of asynchrony in the HER2 gene. It is believed that the elevated level of asynchrony is not restricted to the Her2 gene, but applies to other genes as well, preferably concomitantly expressed genes, more preferably cancer-associated genes, most preferably, oncogenes and tumor suppressor genes.

In a similar, manner as detailed above the TP53 locus was examined using the same groups of occupationally exposed workers and non-exposed individuals. The results obtained with the TP53 gene were similar to those achieved with the HER2 gene.

It is further believed that in individuals exposed to irradiation, a change in the synchrony of non-coding loci can be detected. Such loci corresponding thereto comprise satellite DNA, Associated with chromosome segregation (please see example 8)

EXAMPLE 3

Example 3 shows that changes in synchrony can be detected in amniocytes of foetuses with high risk of cancer.

General methods in this example were carried out as described above; in some instances, methods were carried out differently, or are not detailed above. In these instances, the methods used in this example are as described below.

Cell Cultures

Following amniocentesis diagnoses, 35 human amniotic-fluid cell cultures were established (see Table 3): 11 with normal karyotype (Normal; samples N1–N11); 7 with trisomy 21 (Down syndrome; samples D1–D7); 7 with trisomy 18 (Edwards syndrome; samples E1–E7); 4 with trisomy 13 (Patau syndrome; samples P1–P4); 4 with 47,XXX karyotype (Triple X; samples T1–T4); and 2 with 47,XXY karyotype (Klinefelter syndrome; samples K1 and K2).

Amniotic fluid cultures were grown, harvested, stored and mounted on slides as described above and in a previous publication of the inventors (Amiel et al., Eur. J. Hum. Genet. 6, 359–364, 1998). All cell samples were taken from primary cultures without any passage.

In-situ Hybridization and Cytogenetic Evaluation

One-color FISH was carried out as described above according to the protocol described by the above Amiel et al. 1998. Following hybridization with a given probe, interphase cells which showed two hybridization signals were analyzed (53–190 cells in the various samples; Table 3). Cells were classified into SS cells, SD cells, and DD cells as described in Example 1. The samples were coded before analysis and the frequency of cells in each category was recorded. The level of synchrony in replication timing of any two alleles was derived from the frequency of SD cells.

Statistical Analyses

The differences between the various frequencies were tested both by the student's t-test and the Mann-Whitney U test. The applied tests were two tailed; P values of 1% or less were considered statistically significant.

Figure 4:
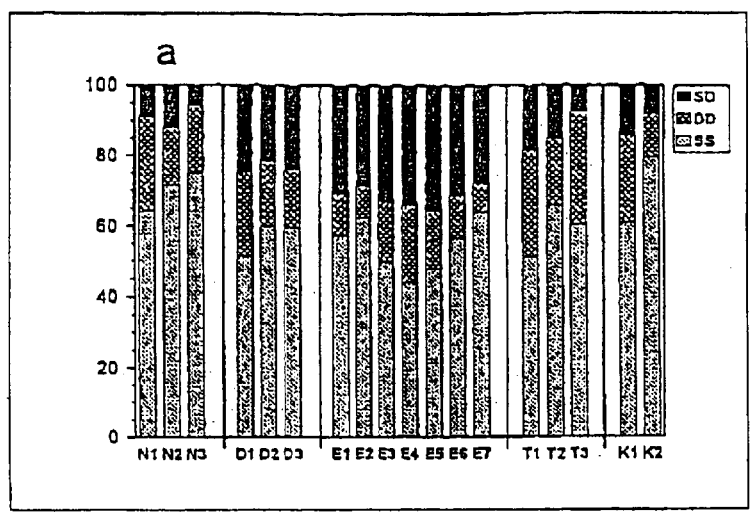
FIG. 4 shows the frequency (%) of SS, DD and SD cells following FISH with probes identifying the RB1 alleles (frame a), HER2 alleles (frame b) and 21q22 alleles (frame c). N1–N11, normal foetues, D1–D7, trisomy 21, E1–E7, trisomy 18, P1–P4, trisomy 13, T1–T4, triple X, K1–K2, 47, XXY; the trisomy 21, 18 and 13 foetuses are at high risk to develop cancer.
Figure 4:
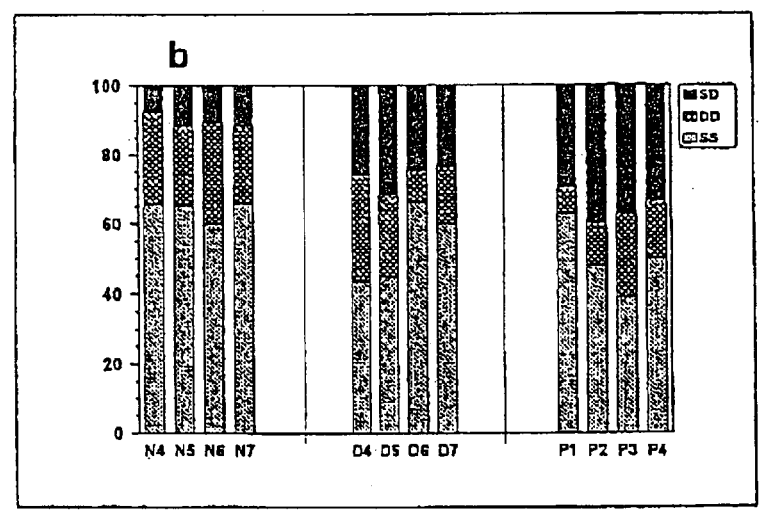
Figure 4:
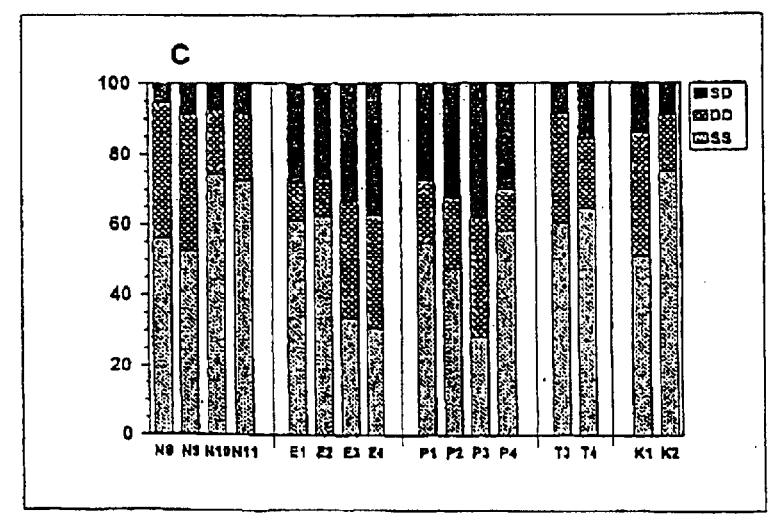

FIG. 4 shows the frequency (%) of SS, DD and SD cells following FISH with probes identifying the RB1 alleles (frame a), HER2 alleles (frame b) and 21q22 alleles (frame c) in cell samples of normal fetuses (Normal; samples N1–N11) and of those with trisomy 21 (Down syndrome; samples D1–D7), trisomy 18 (Edwards syndrome; samples E1–E7), trisomy 13 (Patau syndrome; samples P1–P4), 47,XXX (Triple X; samples T1–T4), and 47,XXY (Klinefelter syndrome; samples K1–K2). The frequency of each group of cells was calculated from the total population of cells revealing two hybridization signals following one-color FISH. The total number of cells examined from each sample for a given probe is listed in Table 3.

Following hybridization with the probe identifying the RB1 locus, the mean frequency of SD cells in samples of normal subjects (samples N1–N3) was 8.9±1.8%. This value was similar (P>0.01) to the corresponding values in samples obtained from foetuses carrying sex chromosome trisomies, triple X and Klinefelter syndrome (samples T1–T3 and K1–K2; means of 13.6±3.3% and 11.2±3.0%, respectively). One should consider, however, that around 10% of SD cells do not stem from asynchronous replication of alleles, but rather from suboptimal hybridization conditions in which one allele fails to reveal the doubled hybridization signal and exhibits a singlet (see Selig et al., EMBO J. 11, 1217–1225, 1992, Lichter et al., Science 247, 64–69, 1994). In contrast, samples derived from fetuses with trisomy 18 or 21 (samples E1–E7 or D1–D3, respectively) showed with the same probe a significantly (P<0.002) higher frequency of SD cells, with mean values of 31.8±1.1% and 23.3±0.9%, respectively (FIG. 4a and Table 4, first row). Comparing samples from the two autosomal trisomies, the RHB1 locus revealed a significantly (P<0.01) higher frequency of SD cells in samples carrying trisomy 18, a condition with severe phenotypic manifestations, compared to samples carrying trisomy 21, which is accompanied by milder phenotypic disturbances (FIG. 4a and Table 4, first row).

Following FISH with the probe for the HER2 locus, the frequency of SD cells was higher in samples carrying trisomy 13 (samples P1–P4) than in samples carrying trisomy 21 (samples D4–D7), with mean percentage of 35.1±9.2 vs. 26.3±1.7, respectively. Evidently, the HER2 locus, similar to the RB1, showed higher frequency of SD cells in samples of trisomy 13, which is associated with more severe phenotypic consequences. However, for both trisomies these values were significantly higher (P=0.01) than the corresponding value obtained in samples of normal subjects (samples N4–N7; FIG. 4b and Table 4, second row).

Samples carrying trisomy 13 (samples P1–P4) or 18 (samples E1–E4) showed a high frequency of SD cells following hybridization with the 21q22 probe too (mean values of 32.2±2.3% and 31.3±2.6%, respectively). These values were much higher than the corresponding values found in samples with sex chromosome trisomies (samples T3, T4, K1 and K2) and in samples of normal subjects (samples N8–N11; FIG. 4c and Table 4, third row). In fact, the replication behavior of the 21q22 locus in cell samples from the various genotypes studied was similar to that revealed by the RB1 and the HER2 loci (FIG. 4 and Table 4).

Thus, the two loci studied in each trisomic genotype showed similar levels of synchrony in replication timing of alleles. Likewise, the three loci studied in the normal genome also showed similar levels of synchrony (FIG. 4 and Table 4).

Considering the combined data of the two loci studied in each trisomic genotype and the three loci in the normal genotype, highly significant differences in the frequency of SD cells were demonstrated between samples of any autosomal trisomy and those of normal subjects (Table 5). Similarly, each genotype with an autosomal trisomy deviated from each genotype with a sex chromosome trisomy, with samples of both sex chromosomes trisomies showing low frequency of SD cells, similar to those observed in samples of normal subjects (Table 5).

Among the autosomal trisomies, two frequency levels of SD cells were observed: a very high level shown by trisomy 13 and 18 —two genotypes with drastic phenotypic consequences (mean frequency values of 33.6±1.6% and 31.6±1.1%, respectively), and a somewhat lower level revealed by the Down syndrome genotype (mean value of 25.0±1.1%), characterized by milder phenotypic disturbances (Tables 4 and 5; FIG. 4).

The frequencies of SS and DD cells showed a large intra-genotypic variation (FIG. 4). However, considering the frequency of SS cells, there appeared a difference (P<0.01) between the pooled data of samples of foetuses with autosomal trisomy (mean of 51.4±2.1%) and the corresponding data of either normal subjects (mean of 65.5±2.2%) or those with sex chromosome trisomies (mean of 62.9±3.2%; Table 6). No significant differences (P>0.01) between the pooled data estimates of the three groups were found in the frequency of DD cells (Table 6). This data indicates that the increased frequency of SD cells in samples of fetuses with autosomal trisomy resulted from an early replication rather than from late replication of a single allele from each pair.

TABLE 3

| | Sample Designation | 13q14 (RB1) | 17q11.2-q12 (HER2) | 21q22 |
|---|---|---|---|---|
| Normal | N1 | 78 | — | — |
| | N2 | 84 | — | — |
| | N3 | 140 | — | — |
| | N4 | — | 81 | — |
| | N5 | — | 69 | — |
| | N6 | — | 95 | — |
| | N7 | — | 79 | — |
| | N8 | — | — | 143 |
| | N9 | — | — | 172 |
| | N10 | — | — | 108 |
| | N11 | — | — | 131 |
| Trisomy 21 (Down's syndrome) | D1 | 78 | — | — |
| | D2 | 102 | — | — |
| | D3 | 101 | — | — |
| | D4 | — | 97 | — |
| | D5 | — | 96 | — |
| | D6 | — | 53 | — |
| | D7 | — | 55— | — |
| Trisomy 18 (Edwards' syndrome) | E1 | 74 | — | 115 |
| | E2 | 66 | — | 87 |
| | E3 | 142 | — | 180 |
| | E4 | 119 | — | 190 |
| | E5 | 78 | — | — |
| | E6 | 89 | — | — |
| | E7 | 93 | — | — |
| Trisomy 13 (Patau's syndrone) | P1 | — | 67 | 76 |
| | P2 | — | 88 | 83 |
| | P3 | — | 113 | 133 |
| | P4 | — | 95 | 99 |
| 47, XXX (Triple X) | T1 | 71 | — | — |
| | T2 | 73 | — | — |
| | T3 | 123 | — | 125 |
| | T4 | — | — | 100 |
| 47, XXY (Klinefelter's syndrome) | K1 | 56 | — | 91 |
| | K2 | 97 | — | 76 |

Number of cells examined in each sample following FISH for loci: 13q14 (RB1), 17q11.2-q12 (HER2) and 21q22

TABLE 5

| | 47, XXY (n = 4) | 47, XXX (n = 5) | Trisomy 13 (n = 8) | Trisomy 18 (n = 11) | Trisomy 21 (n = 7) |
|---|---|---|---|---|---|
| Normal (n = 11) | $t_{13}$ = 1.618 | $t_{14}$ = 2.231 | $t_{17}$ = 15.078 | $t_{20}$ = 16.689 | $t_{16}$ = 12.169 |
| | $P > 0.01$ | $P > 0.01$ | $P < 0.001$ | $P < 0.001$ | $P < 0.001$ |
| | — | — | — | — | — |
| | U = 33.0 | U = 40.0 | U = 0.0 | U = 0.0 | U = 0.0 |
| | $P > 0.01$ | $P > 0.01$ | $P < 0.002$ | $P < 0.002$ | $P < 0.002$ |
| Trisomy 21 (n = 7) | $T_9$ = 6.273 | $t_{10}$ = 4.814 | $t_{13}$ = 4.049 | $t_{16}$ = 3.758 | — |
| | $P < 0.001$ | $P < 0.001$ | $P < 0.01$ | $P < 0.01$ | |
| | — | — | — | — | |
| | U = 0.0 | U = 0.0 | U = 3.0 | U = 5.0 | |
| | $P = 0.003$ | $P = 0.001$ | $P = 0.001$ | $P < 0.002$ | |
| Trisomy 18 (n = 11) | $t_{13}$ = 9.009 | $t_{14}$ = 7.930 | $t_{17}$ = 1.020 | — | — |
| | $P < 0.001$ | $P < 0.001$ | $P > 0.01$ | | |
| | — | — | — | | |
| | U = 0.0 | U = 0.0 | U = 55.0 | | |
| | $P < 0.002$ | $P < 0.002$ | $P > 0.01$ | | |
| Trisomy 13 (n = 8) | $t_{10}$ = 8.119 | $t_{11}$ = 7.262 | — | — | — |
| | $P < 0.001$ | $P < 0.001$ | | | |
| | — | — | | | |
| | U = 0.0 | U = 0.0 | | | |
| | $P = 0.002$ | $P = 0.001$ | | | |
| 47, XXX (n = 5) | $t_7$ = 0.504 | — | — | — | — |
| | $P > 0.01$ | | | | |
| | — | | | | |
| | U = 17.0 | | | | |
| | $P > 0.01$ | | | | |

Significance of the differences between any two genotypes in the frequency of cells showing one singlet and one doublet (SD cells; n = total number of samples studied for each genotype); both the t-test and the Mann-Whitney U-test were used for the evaluation. Please refer to Example 1 and to the Cytogenetic Evaluation in the Methods section above for more details.

TABLE 4

| Locus | Parameter | Normal | Trisomy 18 | Trisomy 18 | Trisomy 13 | 47,XXX | 47,XXX |
|---|---|---|---|---|---|---|---|
| 13q14 (RB1) | N | 3 | 3 | 7 | — | 3 | 2 |
| | Mean ± SE | 8.9 ± 1.8 | 23.3 ± 0.9 | 31.8 ± 1.1 | | 13.6 ± 3.3 | 11.2 ± 3.0 |
| | Median | 9.0 | 23.8 | 31.5 | | 15.1 | 11.2 |
| | Range | 5.7–11.9 | 21.6–24.4 | 28.0–35.9 | | 7.3–18.3 | 8.2–14.3 |
| 17q11.2-q12 (HER2) | N | 4 | 4 | — | 4 | — | — |
| | Mean ± SE | 10.2 ± 1.0 | 26.3 ± 1.7 | | 35.1 ± 2.2 | | |
| | Median | 10.9 | 25.2 | | 35.4 | | |
| | Range | 7.4–11.6 | 23.6–31.2 | | 29.8–39.8 | | |
| 21q22 | N | 4 | — | 4 | 4 | 2 | 2 |
| | Mean ± SE | 7.3 ± 0.7 | | 31.3 ± 2.6 | 32.2 ± 2.3 | 12.4 ± 3.6 | 11.7 ± 2.5 |
| | Median | 7.9 | | 29.9 | 31.4 | 12.4 | 11.7 |
| | Range | 5.6–8.7 | | 26.4–37.9 | 27.6–38.3 | 8.8–16.0 | 9.2–14.3 |
| All estimates | N | 11 | 7 | 11 | 8 | 5 | 4 |
| | Mean ± SE | 8.9 ± 0.7 | 25.0 ± 1.1 | 31.6 ± 1.1 | 33.6 ± 1.6 | 13.1 ± 2.1 | 11.5 ± 1.6 |
| | Median | 8.7 | 24.4 | 31.5 | 33.0 | 15.1 | 11.7 |
| | Range | 5.6–11.9 | 21.6–31.2 | 26.4–37.9 | 27.6–39.8 | 7.3–18.3 | 8.2–14.3 |

Frequency values (%) of cells showing one singlet and one doublet (SD Cells) in cell populations of the various genotypes following FISH with probes identifying the RB1, HER2, and 21q22 loci (n = number of samples studied for each genotype). Please refer to Example 1 and to the Cytogenetic Evaluation in the Methods section above for more details.

TABLE 6

|  | Sex chromosome trisomies (n = 9) | Autosomal trisomies (n = 26) |
|---|---|---|
| SS cells | | |
| Normal (n = 11) | $T_{18}$ = 0.645<br>P > 0.01 | $t_{35}$ = 3.907<br>P < 0.001 |
| Autosomal trisomies (n = 26) | $T_{33}$ = 2.784<br>P < 0.01 | — |
| DD cells | | |
| Normal (n = 11) | $T_{18}$ = 0.214<br>P > 0.01 | $t_{35}$ = 2.530<br>P > 0.01 |
| Autosomal trisomies (n = 26) | $T_{33}$ = 2.055<br>P > 3.01 | — |

Significance of the differences between the indicated genotypes in the frequency of cells showing two singlets (SS cells) and two doublets (DD cells; n = total number of samples studied for a given group of genotypes). Please refer to Example 1 and to the Cytogenetic Evaluation in the Methods section above for more details.

EXAMPLE 4

Blood samples were collected as described above in Example 1. Bone marrow samples were collected as described in Amiel et al., Gene Chrom. Cancer 22, 225–231, 1998.

Blood samples were pretreated by PHA as described in Example 1.

Samples were analyzed by FISH as described above in Example 1 and in the above Amiel et al., Gene Chrom. Cancer, 1998.

The probes used are DiGeorge, hybridizing to a site at 22.q11.2 within the DiGeorge locus. Further, probe STS WI-941 was used, which targets a site at 22q11.2 near the DiGeorge locus. This probe corresponds to sequence tag STS WI-941. Further, two probes for the Prader-Willi licus were used, D15S10 and a probe hybridizing to GABRB3.

Figure 5:
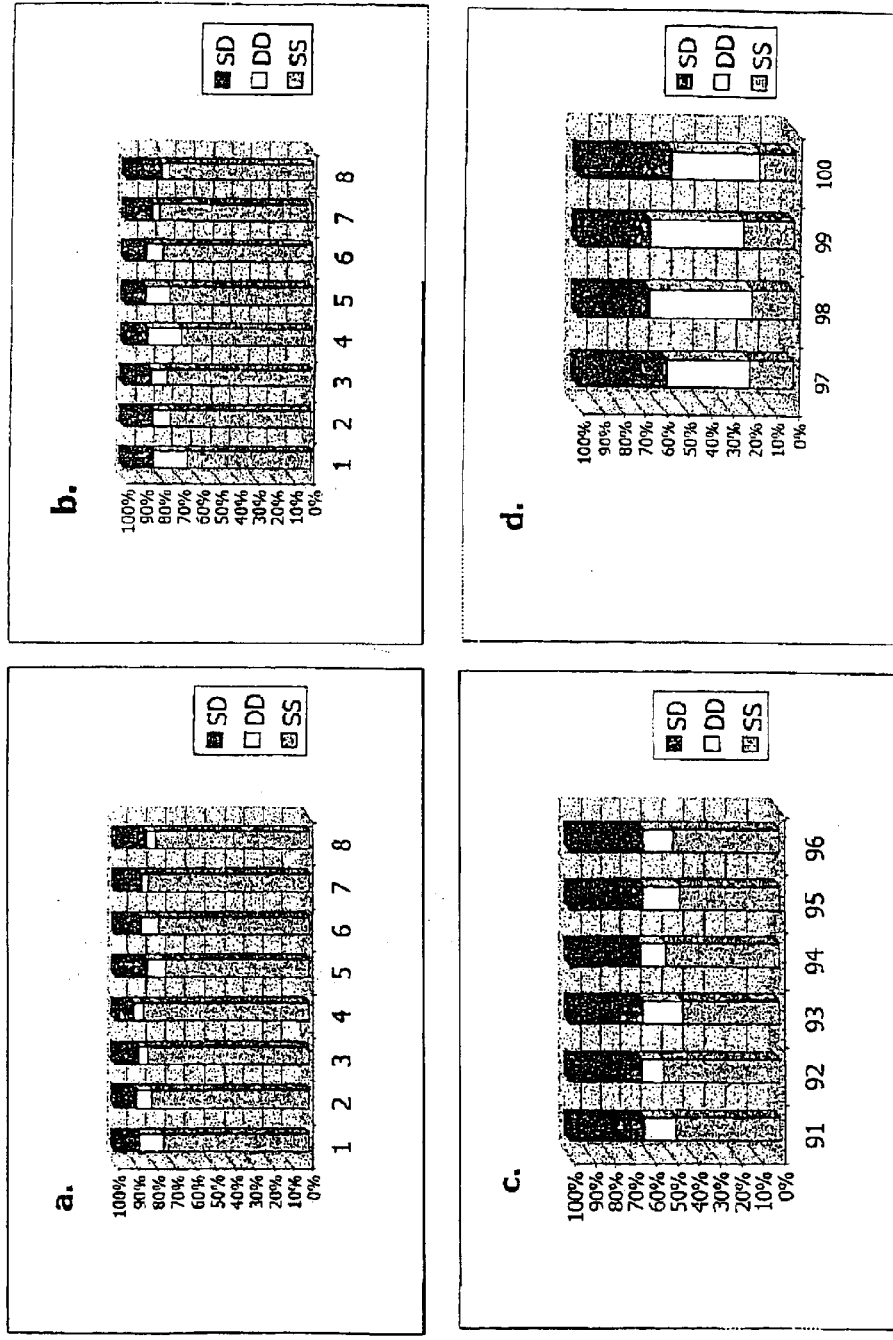
FIG. 5 shows the percentage of SD cells in bone marrow cells (first two samples) and in blood cells (the other samples) from healthy controls, analyzed with different probes (FIG. 5a, DiGeorge (D22S75), FIG. 5b, STS WI-941, FIG. 5c, D15S10, FIG. 5d, GABRB3)

FIG. 5 shows the frequency of SD cells in blood and bone marrow derived samples from healthy subjects. In FIGS. 5a and 5b, results are derived from analysis using probes for biallelic loci, DiGeorge and STS WI-941. In FIGS. 5c and 5d, results shown are derived using probes for monoallelic, imprinted genes located in the Prader-Willi locus.

FIG. 5a shows that the frequency of SD cells in healthy subjects, when using probe DiGeorgve, is between about 12% and about 20%. There appears to be no difference between samples obtained from bone marrow (3–8) and from blood (1–2). FIG. 5b shows results of analysis of the same samples using the STS WI-941 probe. The frequency of SD cells ranges from about 14% to about 22%. Again, there appears to be no difference between blood and bone marrow-derived samples.

FIGS. 5c and 5d show frequencies of SD cells in blood derived samples (91–100). FIG. 5c shows that the frequency of SD cells when using the D15S10 probe, is about 40%, with very little variance. FIG. 5d shows that the frequency of SD cells when using the GABRB3 probe, is even higher, between about 40% and about 50%.

The data in FIG. 5 suggest that there is little difference synchrony values between bone marrow and blood samples. The difference in the values between FIGS. 5c and 5d is believed to be due to the difference in the probe used. Thus, different regions within the Prader-Willi locus replicate differently, although with little difference in synchrony values.

Figure 6:
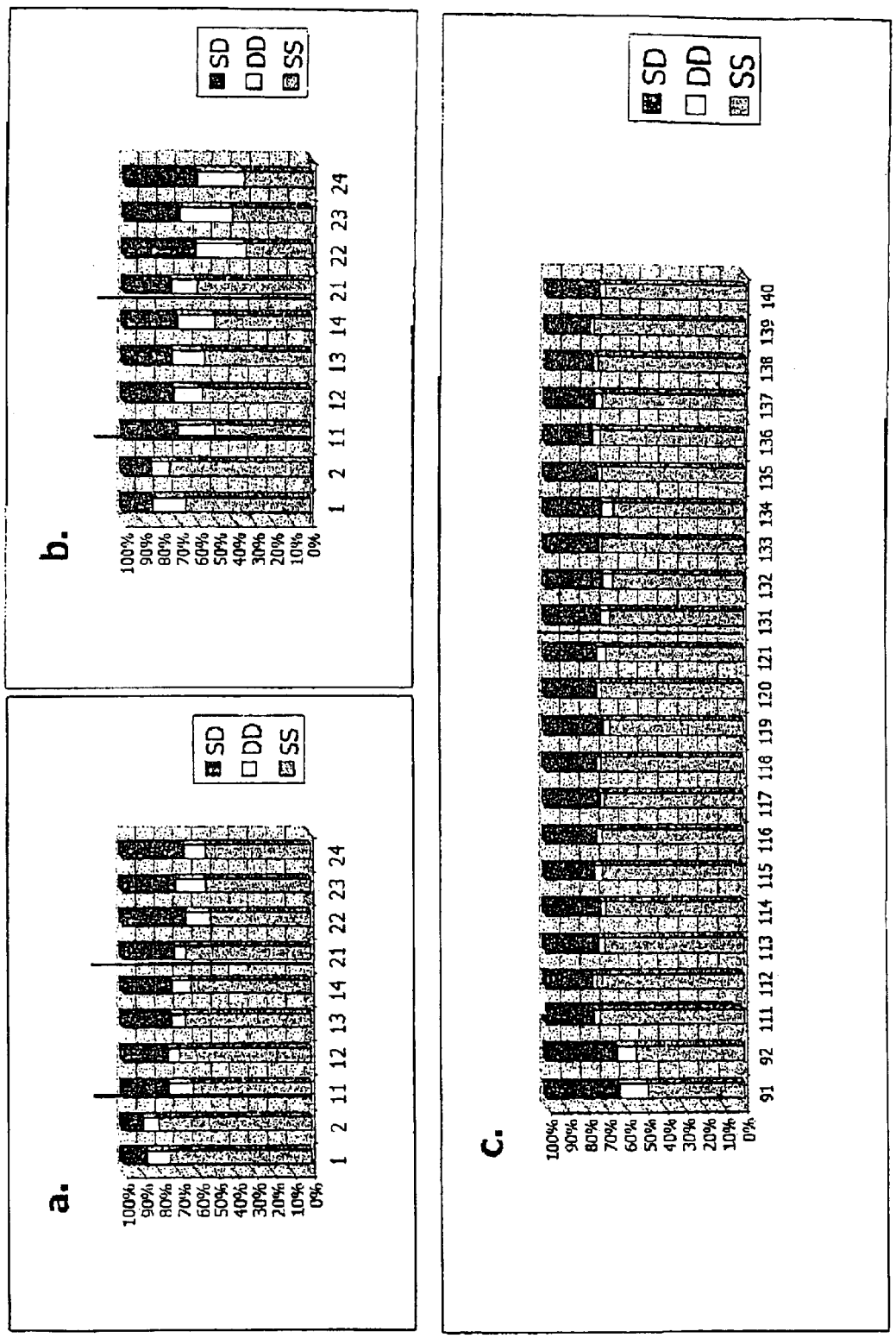
FIG. 6 shows the percentage of SD cells in bone marrow samples of cancer-afflicted individuals, as analyzed with various probes (FIG. 6a, DiGeorge, FIG. 6b, STS WI-941, FIG. 6c, D15S10). The first two samples are normal samples whereas the others are samples derived from cancerous individuals.

FIG. 6 shows results obtained from bone-marrow derived samples. When comparing the above described frequency of SD cells in healthy subjects with those of cancer-afflicted individuals, significant differences are observed. FIG. 6 shows that in contrast to samples from healthy subjects (1–2, 91–92), the samples from lymphoma (11–14, 111–121) and chronic myelocytic leukemia (CML, 21–14, 131–140) patients show elevated frequencies of SD cells.

When using the DiGeorgve probe, SD cell frequency in lymphoma pagtients ranged from about 26% to about 30%. The frequency of SD in samples of CML patients was even more elevated, ranging from between about 33% to about 38% . This contrasts with the low frequency of SD cells in healthy subjects, which is below 20% (see FIG. 6a and description hereinabove).

Similar data were obtained when using the WI-924 probe. SD cell frequency ranged from about 30% to about 33% in lymphoma patients and from about 30% to about 42% in CML patients (FIG. 6b). This contrasts with about 20% or less in healthy subjects (FIGS. 6b, 5b).

The above probes correspond to loci that are expressed biallelically, i.e., where both alleles are expressed. In such loci, it is expected that replication for both alleles is essentially simultaneous, i.e. synchronous.

The data presented in FIG. 6c show results obtained using probes for the Prader-Willi locus. This locus is imprinted and expressed monoallelically. Thus, it is expected that it replicates asynchronously. The data detailed above, from healthy subjects, show indeed high frequencies of SD cells (FIGS. 5c and 5d, samples 91–100, and FIG. 6c, samples 91–92).

Data obtained from individuals afflicted with lymphoma (samples 111–121) or CML (samples 131–1140), on the other hand, showed significantly lower frequencies of SD cells in bone marrow samples, ranging between 25% and 32% (FIG. 6c). There appeared to be no difference between lymphoma and CML patients (FIG. 6c, compare samples 111–121 to samples 131–140, respectively).

These data show that as expected, biallelically expressed genes exhibit low levels of asynchrony as measured in blood and bone marrow cells (FIGS. 5a and 5b, 10–20%). In bone marrow samples of individuals afflicted with cancer, on the other hand, the asynchrony level is highly elevated (FIGS. 5a and 5b, 30–40%).

An opposite effect is observed in genes that are expressed monoallelically. The Prader-Willi locus is known to be imprinted, with the result that one of its alleles is silent, while the other is normally expressed. As expected, the Prader-Willi locus replicates asynchronously, as shown in FIGS. 5c and 5d for the D15S10 and the GABRB3 probes (40 and 40 to 45%, respectively).

In patents, the asynchrony level at the Prader-Willi locus is significantly reduced (FIG. 5c, D15S10 probe, about 30% average).

Thus, the above data show a relaxation of replication control in cells of individuals suffering from cancer. Genes that replicate synchronously, appear to lose tight control of their replication time, and are replicated asynchronously. On the other hand, genes that in healthy subjects, are replicated highly asynchronously, in cancer-afflicted individuals also appear to lose the tight control necessary to replicate these genes at far distant time points in the S-phase. In consequence, these genes replicate synchronously.

However, a gene which replicates normally asynchronously, does not change its replication control to the point of synchronous replication in cancer-afflicted individuals: rather, the replication timing appears to assume a middle position between asynchronous and synchronous (FIG. 5c, ~30%). On the other hand, genes normally replicating synchronously acquire about the same level (~30%) of synchrony in cells of cancer-afflicted individuals.

Therefore, without wishing to be bound by theory, it is believed that the phenomenon of changing replication pattern is due to a general relaxation of replication control, not to a specific enhancement of synchrony in monoallelically expressed genes on the one hand, and a specific decrease in synchrony in biallelically expressed genes.

EXAMPLE 5

In this example, synchrony was examined in peripheral blood lymphocytes (PBL) of healthy individuals and individuals suffering from cancer. In addition, in the effect of treatment of healthy individuals with GCSF on the synchrony of their PBL was investigated.

Sample Description

Normal controls versus cancer patients—A total of seventy-one subjects were tested. Fifty-two subjects were normal, healthy controls (samples 1–52). Nineteen subjects were patients suffering from various hematological malignancies (samples 61–80). Samples of patients were obtained upon diagnosis, before commencement of any treatment. Peripheral blood (PBL) samples were obtained from 40 healthy subjects, as control, and from 19 leukemic patients (PBL samples marked with "L" in the sample number).

Bone marrow derived cells were tested from 16 patients and 12 healthy donors (marked with "B" in the sample number). Sample numbers for none marrow and PBL samples are identical when samples were obtained from the same patient. Table 6 lists the distribution of gender and age among the different groups tested, and the sample designations.

the 21q22 probe (D21S55, Vysis 32-190002). Table 7b lists results of PBL cells hybridized with the TP53 probe mapped to 17p13.1.

With both probes, the average percentage of SD cells in donors is about 20% SD cells (21q22 probe, Table 7a, 18.57%, TP53 probe, Table 7b, 20.8%). There is no significant difference in this value between donors (n=6) and a larger group of healthy subjects (n=40, Table 7a, 18.7%, Table 7b, 18.7%).

In contrast, patients with hematological malignancies show significantly enhanced percentages of SD cells (21q22 probe, 38%, TP53 probe, 36.9%, n=19).

Treatment of healthy donors with GCSF resulted in significantly enhanced values of SD cell percentrage (21q22 probe, 35.42%, TP53 probe, 36.57%, n=6). It is believed that the SD cell percentage values are enhanced for a limited time and return to normal after cessation of GCSF treatment. The samples tested here were obtained five days after GCSF treatment. This period is usually chosen for obtaining cells for transplantation, because at the effect of GCSF is maximal five days after administration.

GCSF is a hematopoietic growth factor. It is given to donors of bone marrow cells in order to enhance the number of stem cells in the bone marrow sample which is then used for transplantation.

It is believed that enhanced numbers of SD cells is also observed when cells are treated with other growth factors. However, not any growth stimulus will result in enhanced SD cell percentage, or more generally, in a change of synchrony. This is demonstrated by earlier examples herein wherein PBL cells are stimulated with PHA. These cells present low (10 to 20%) values of synchrony in biallelically expressed genes. This value is expected for biallelically expressed genes, and therefore it is assumed that PHA treatment of PBL cells does not change synchrony levels.

TABLE 7

| | Controls | | | | Patients | | | |
|---|---|---|---|---|---|---|---|---|
| | Tissue | | | | | | | |
| | PBL | | Bone marrow | | PBL | | Bone marrow | |
| | Gender | | | | | | | |
| | Male | Female | Male | Female | Male | Female | Male | Female |
| N | 24 | 16 | 10 | 0 | 11 | 8 | 12 | 4 |
| Age | 16–54 | 23–65 | 11–54 | — | 12–55 | 20–57 | 12–55 | 20–57 |
| Sample number | 1L–24L | 25L–40L | 41B–52B | — | 61L–73L | 74L–81L | 61B–73B | 74B–77B |

Healthy subjects treated with GCSF. Seven first degree relatives (sibling or parent) of patients suffering from hematological malignancies who were candidates for donating peripheral blood stem cells agreed to participate in the study. PBL were collected before treatment with GCSF and five days after treatment, on the day of collecting cells for transplantation. Six donors were male, one female.

Comparison of synchrony in healthy subjects, cancer patients and GCSF-treated healthy donors. Bone marrow and PBL samples were obtained with informed consent from healthy control subjects and patients as detailed hereinabove. Samples were analyzed by FISH as described hereinabove. Table 7a lists results of PBL cells hybridized with

TABLE 8

| Sample | % SD before treatment | % SD after GCSF treatment |
|---|---|---|
| A. | | |
| 20 | 17 | 31 |
| 21 | 24 | 29 |
| 22 | 15 | 35 |
| 23 | 20 | 39 |
| 24 | 20 | 32 |
| 25 | 18 | 43 |
| 41 | 16 | 39 |

TABLE 8-continued

| Sample | % SD before treatment | % SD after GCSF treatment |
|---|---|---|
| Average n = 6 | 18.57 | 35.42 |
| Standard error | 1.15 | 1.93 |
| Average normal controls N = 40 | 18.7 | — |
| Standard error | 0.53 | |
| Average cancer patients N = 19 | 38 | — |
| Standard error | 1.74 | |
| B. | | |
| 20 | 22 | 34 |
| 21 | 18 | 41 |
| 22 | 23 | 38 |
| 23 | 19 | 34 |
| 24 | 20 | 36 |
| 25 | 22.6 | 36 |
| 41 | 21 | 37 |
| Average n = 6 | 20.8 | 36.57 |
| Standard error | 0.71 | 0.92 |
| Average normal controls N = 40 | 18.7 | — |
| Standard error | 0.50 | |
| Average cancer patients N = 19 | 36.9 | — |
| Standard error | 1.17 | |

EXAMPLE 6

Subjects

Fifty-six individuals of which 15 (samples 1–15) were patients suffering from a hematological cancer and 41 (samples 16–56) were healthy non-cancerous individuals. The patients, eight males and seven females (aging between 3 and 80 years) were examined prior to any clinical treatment. Specifically, nine of them were diagnosed with AML (acute myeloid leukemia), three with CLL (chronic lymphocytic leukemia), one with ALL (acute lymphoblastic leukemia), one with CML (chronic myeloid leukemia) and one with Multiple Myeloma. The non-cancerous subjects, of which 24 were males (samples 16–23 and 38–53) and 17 females (samples 24–37 and 54–56), aged between 11 and 71 years.

Cell cultures

Each subject donated five ml of peripheral blood. Cell cultures of PHA-stimulated lymphocytes were set up according to standard protocol (Rooney and Czepulkowsli, 1992). Briefly, 0.5 ml of peripheral blood was introduced into a 15 ml test tube containing 5ml F-10 medium supplemented with 20% fetal calf serum, 0.2% heparin, 1% penicillin/streptomycin antibiotic solution (Biological industries, Israel) and 3% phytohemagglutinin (PHA). In addition, all the 15 samples derived from the hematological patients (samples 1–15) and 15 of the 41 samples derived from non-cancerous subjects (samples 16–30) were also grown in the presence of $10^{-7}M$ 5-azacytidine (AZA; Sigman, USA) added to the other ingredients described above.

After 72 hours at 37° C., colchicine (Sigma, USA) was added to each sample (final concentration of $5 \times 10^{-7}M$ for one hour) followed by hypotonic treatment (0.075 M KCl at 37° C. for 15 minutes) and four washes, each with a fresh cold (–20° C.) 3:1 solution of methanol: acetic acid. The cell suspensions were stored at –20° C. until used for FISH.

Slide Preparation

The stored cell suspensions prepared for FISH were washed twice in a 3:1, methanol: acetic acid solution, diluted until the suspension became slightly cloudy. Approximately seven μl of the suspension were dropped onto the marked circles of two-well slide glasses. The two-well slides were obtained from Ingen Laboratories (USA, currently Insitus Biotechnologies) and used without any pretreatment.

Probes

Six diverse loci were tested using directly labeled commercial probes obtained from Vysis: (i) the SNRPN probe (32-190004); (ii) the TP53 probe (32-190006); (iii) the AML1 probe (LSI 21; 32-190002); (iv) the RB1 probe (LSI 13; 32-190001); (v) the α-satellite probe specific for centromere 17 (32-130017, hereafter marked as CEN17); and (vi) the satellite III probe specific for centromere 15 (32-1300015, hereafter marked as CEN15). The SNRPN probe identifies the Prader-Willi/Angelman syndrome region on 15q11–13 and is the most well characterized imprinted region in man (Ozoelik et al 1992). The TP53 probe identifies the p53 gene mapped to 17q13.1 and is a tumor suppressor gene whose deletion and/or inactivation is implicated in over 50% of all human tumors (Prokocimer et al 1998). The AML1 probe recognizes a gene mapped to chromosome 21q22, which is one of the most frequently translocated genes in human blood malignancy (Look 1997). The RB1 probe identifies the archetypal tumor suppressor gene, the first gene demonstrated to show a loss of function in a human tumor (Friend et al 1986). It is located on chromosome 13q14, and encodes the retinoblastoma protein. Both centromere specific probes (CEN17 and CEN15) identify non-coding loci implicated with chromosomal segregation and stability and are usually used for the enumeration of chromosome 17 and 15, respectively. Also the AML1 and RB1 probes, although not identifying centromeric regions, were both approved by the FDA to replace centromere specific probes for the enumeration of chromosomes 21 and 13, respectively.

In-situ Hybridization

A standard protocol was followed, as recommended by Ingen Laboratories (currently Insitus Biotechnologies), with few minor changes. Probes were diluted in Ingen's DenHyb solutions D001 to 400 folds (CEN17 and CEN15) and in D003 to 100 fold (AML1; RB1) or 50 fold (TP53; SNRPN) instead of the hybridization solution supplied with the probe. Five μl of the probe solution was placed on the targeted area of the sample slides and covered with a 12 mm round silanized coverslip (Ingen laboratories, USA) at 76° C. and denatured for six minutes at that temperature. The slide-filled aluminum slide tray was then transferred into an HybBox (Ingen Laboratories, USA), covered and allowed to hybridize overnight in the box.

Detection

Post hybridization wash for probe TP53 was carried out by immersing the slides in 4×SSC (1×SSc=150 mM NaCl, 15 mM sodium citrate) for five minutes at room temperature. Post hybridization washes for probe AML1 and RB1 consisted of immersing the slides for 20 seconds in a solution of 0.4×SSC pH 7.0 with 0.3% NP40, followed by 20 seconds in 2×SSC with 0.1% NP40 at 60° C. in a shaking water bath. The post washing of the centromer specific probes was carried out in the same solutions as the AML1 and RB1 probes except that the temperature was set to 75° C. and lasted for two minutes in the first solution and one minute in the second. After draining off excess liquid and brief drying, the slides were treated with 15 μl/test of a solution of antifade containing 4,6-diamidino-2-phenylindole (DAPI) as counterstain at 3 μg/ml (Vectashield, Vector Labs, USA). Slides were covered with glass-coverslips (22×60 mm) and stored at –20° C. until analyzed (between one hour and two days).

Sample Size

All samples obtained from the cancerous patients (samples 1–15) were analyzed with each of the six probes used, each in the absence as well as in the presence of AZA. Out of the non-cancerous samples grown without AZA 41 (samples 16–56) were analyzed with the AML1 and TP53 probes, 30 (samples 16–45) with the CEN17 probe and 15 (samples 16–30) with each of the other three probes (SNRPN, RB1 and CEN15).

Each of the 15 samples derived from the noncancerous subjects (samples 16–30) grown in the presence of AZA was also analyzed with each of the six probes used.

Cytogenetic Evaluation

Slides were analyzed blindly on an Olympus BH2 fluorescent microscope, using a triple band-pass filter (Chroma technology). For the replication assay (Boogs and Chinault, 1997) at least 100 cells, containing two well-defined hybridization signals were scored from each sample, for each probe and for each treatment, following one-color FISH. The structure of each signal, either singlet (S), representing a non-replicated sequence, or doublet (D), disclosing a replicated sequence, was noted FIG. 1. The criteria for defining a doublet and distinguishing it from a singlet, were that the two spots forming the doublet structure were of comparable size and brightness, and were not separated from each other by a distance longer than twice their diameter size. Accordingly, cells were divided into three categories: (i) cells containing two non-similar signals, a non-repticated and a replicated one (SD cells; FIG. 1$a$), (ii) cells carrying two similar signals, both non-replicated (SS cells; FIG. 1$b$) and (iii) cells carrying two similar signals, both replicated (DD cells; FIG. 1$c$). SD cells disclose allelic sequences differing in their replication status, whereas, SS and DD cells represent allelic sequences at the same replication status. The frequency of SD cells, out of the total population of cells containing two well defined hybridization signals, was used to evaluate the level of asynchrony in the replication timing of the various allelic sequences in the samples studied.

For the analyses of chromosome losses and gains, at least 200 cells following one-color FISH with each of the chromosome enumerating probes (AML1, RB1, CEN17 and CEN15) were scored for each tested sample, employing the same preparation used for evaluating allelic replication timing. The frequency of cells containing a single signal was used to evaluate the extent of chromosome losses and the frequency of cells with three or more signals were used to assess the level of chromosome gains.

Statistical Analysis

The statistical significance of the difference between two tested groups of samples was carried out using two-tailed Student's t-test (Microsoft Office 97, Excel), after ascertaining the normal distribution of the data in each group. P values of 1% or less were considered to be statistically significant.

Results

The frequency of SD cells were examined following one-color FISH with each of six different probes (SNRPN, TP53, AML1, RB1, CEN17 and CEN15) in PHA-simulated lymphocytes derived from two groups of subjects: (i) patients suffering from a hematological malignancy (samples 1–15) and (ii) non-cancerous individuals (samples 16–56). The two groups of samples exhibited both a high and a similar ($P>0.70$) frequency of SD cells for the SNRPN locus, with mean and standard deviation value of 38.1±5.0% for the patients and 37.3±7.9% for the non-cancerous individuals (first frame in FIG. 7$a$). These values are expected for an imprinted locus, and were used hereafter as markers for loci displaying allele specific replication.

However, in contrast to the similarity shown between the two groups of samples in the SD frequency for the SNRPN locus there were highly significant differences ($P<10^{-12}$) in the SD values between samples derived from patents and those from non-cancerous subjects for the other five (non-imprinted) loci (Table 8). While in samples of non-cancerous subjects the TP53, AML1, RB2, CEN17 and CEN15 loci all exhibited a relatively low frequency of SD cells, these very same loci when present in the cancerous samples each showed a high SD value characteristic for loci displaying an allele specific mode of replication. Specifically, the mean SD values in the non-cancerous samples for TP53, AML1, RB1, CEN17 and CEN15 were much lower than the values observed for the SNRPN ($P<10^{-10}$, 18.5±3.4%, 20.±5.32%, 19.5±4.1%, and 18.1±2.9%, respectively). Whereas, the mean percentage of SD cells obtained for a given locus in the patients' samples was twice as high as that found in the non-cancerous samples. The corresponding values were 40.2±4.6% for TP53, 41.2±3.5% for AML1, 39.4±4.3 FOR RB1 and 37.5±4.5% for CEN17 similar to that observed for the imprinted SNRPN locus, and 44.6±3.2% for CEN15, even higher than the frequency obtained for the imprinted locus (Table 8 and FIG. 7$a$).

Figure 7:
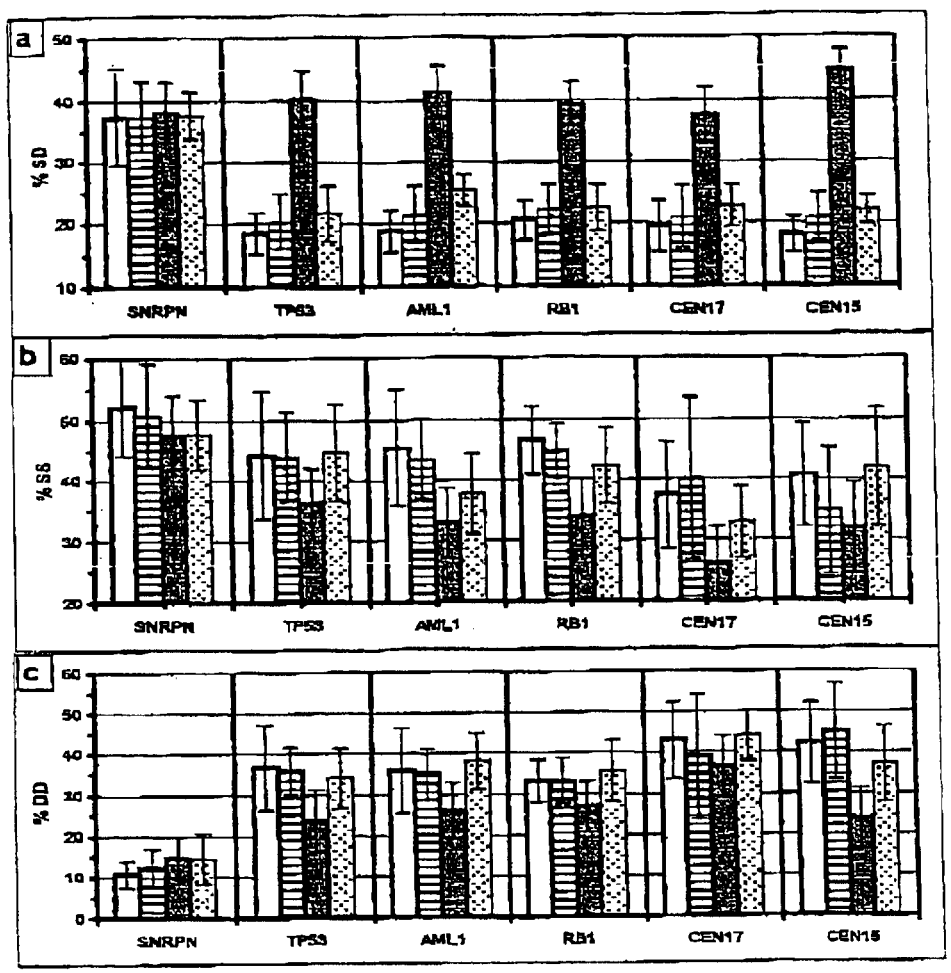
FIGS. 7A–C are graphs showing the mean and standard deviation of the frequency (%) of cells exhibiting the SD (frame a), SS (frame b) and DD (frame c) of the designated coding loci and the designated non-coding centromeric loci in cells of normal and cancerous individuals in the presence and absence of a agent associated with gene expression and chromatin conformation (AZA). empty bars and striped bars represent non-cancerous samples grown in the absence and presence of a demethylating agent, respectively; solid bars and dotted bars represent cancerous samples grown in the absence and presence of a demethylating agent, respectively.

Evidently, the SD cell frequency of three independent loci, possessing transcriptional capability (TP53, AML1 and RB1) as well as of two transcriptionally inert loci (CEN17 and CEN15), increased dramatically in the samples of the patients, each enabling a clear cut differentiation between cancer affected individuals and non-cancerous subjects (FIG. 7$a$). This clear-cut differentiation is well manifested when each sample is presented by the mean SD value of all five loci (TP53, AML1, RB1, CEN17 and CEN15).

The combined SD value of the malignant samples (samples 1–15) ranged between 37.4–42.0%, while that of the non-cancerous samples (samples 16–30) ranged from 16.6–21.7%.

The increase in the frequency of SD cell population observed in the patients' samples for TP53, AML1, RB1 and CEN15 arises from a decrease in both the frequency of the SS and DD cell populations. Thus indicating that the malignant status leads to early replication as well as to late replication of a single allele from each locus (FIGS. 7$b$ and $c$; Table 9, row 1 and 2). The CEN17 locus behaves somewhat differently and appears to be affected by the malignant status mostly due to a decrease in its SS cell population rather than in the DD population (frame 5 in FIGS. 7$b$ and $c$; Table 9, row 1 and 2).

The Abnormal Allele Specific Replication Mode Caused by the Malignant Status is Reversed to the Normal One in the Presence of 5-azacytidine Thirty samples (samples 1–30) were grown in duplicates, without and in the presence of 5-azacytidine (AZA). The presence of the drug did not change the SD cell frequency for the SNRPN locus in any of the samples, either of the patients (samples 1–15) or of the non-cancerous subjects (samples 16–30) (first frame in FIG. 7$a$). However, the frequency of SD cells for TP53, AML1, RB1, CEN17 and CEN15 in the patients' samples decreased dramatically following exposure to the demethylating agent, while the non-cancerous samples were not affected by the presence of the drug (FIG. 2$a$). Specifically, in the patients' samples the percentage of SD cells following exposure to AZA ranged between 15–28%, with a mean value of 21.7±4.4% for TP53, 25.3±3.7% for AML1, 22.4±2.5% for RB1, 22.7±3.4% for CEN17 and 21.9±2.3% for CEN15. The corresponding mean values in the AZA-exposed non-cancerous samples were 20.4±4.4% for TP53, 21.5±4.5% for AML1, 22.3±3.9% for RB1, 20.9±5.0% for CEN17 and 20.9±3.8% for CEN15 (ranging 12–29%).

Evidently in the presence of the drug the two groups of samples, patents and non-cancerous subjects, displayed similar frequencies of SD cells (P>0.40 for TP53, P>0.01 for AML1, P>0.20 for CEN17 and P>0.30 for CEN15). Moreover, the patients' samples in the presence of AZA displayed values similar to those of the AZA unexposed group of non-cancerous samples and highly differing from values obtained in the unexposed patients' group ($P<10^{-11}$ for TP53, RB1; $P<10^{-9}$ and $P<10^{-17}$ for CEN17 and CEN15, respectively) (FIG. 7a).

The difference in the response to AZA between non-cancerous samples and samples derived from patients is clearly elucidated when each sample is expressed by the combined data of all five loci (mean SD frequency value of TP53, AML1, RB1, CEN17 and CEN15). Accordingly, the frequency of SD cells in the group of patients' samples exposed to AZA (ranging 19.8–26.2%) almost matches the corresponding range in the group of AZA unexposed non-cancerous samples (ranging 14.5–23%), and is much lower from that obtained in the AZA unexposed group of patients' samples (ranging 37.4–44.2%). In contrast, the non-cancerous samples exposed to AZA displayed combined frequencies of SD cells (ranging 16.7–24.6%) similar to that of the AZA unexposed non-cancerous samples.

Figure 8:
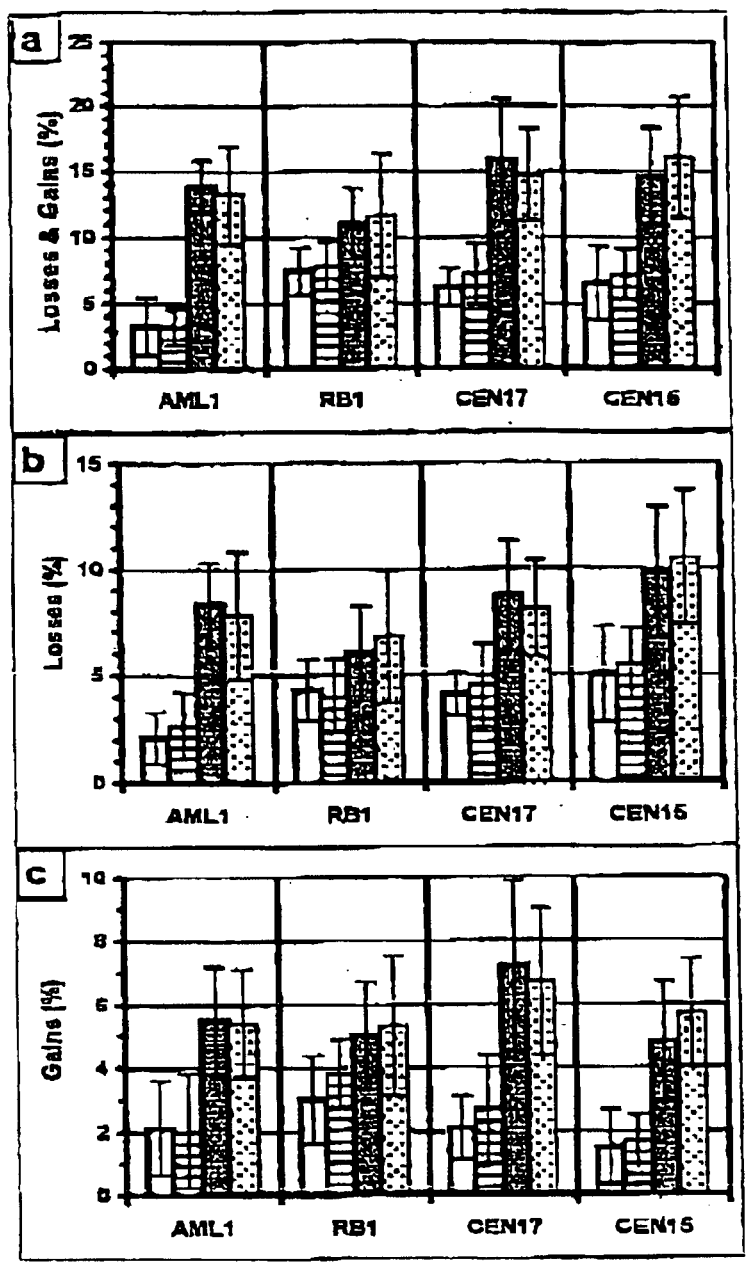
FIGS. 8A–C are graphs showing the mean and standard deviation of the frequency (%) of cells exhibiting losses and gains for chromosome 21, chromosome 13, chromosome 17 and chromosome 15 in cancerous and non-cancerous samples in the presence and absence of a demethylating agent AZA; For details please see the legend of FIG. 8.

Hematological Cancer is Associated with Genetic Instability Manifested by an Increased Frequency of Chromosome Losses and Gains Using AML1, RB1, CEN17 and CEN15 there was determined, in the cancerous and the non-cancerous samples the frequency of cells disclosing losses and gains of chromosome 21, 13, 17 and 15, respectively (FIG. 8). In the malignant group of samples the mean frequency value of cells with one, three or more signals for a given locus ranged between 11.0±2.7% (for RB1) and 15.8±4.7% (for CEN17). These values appeared to be significantly higher than those observed in the non-cancerous group of samples, which ranged between 3.2±0.2% (for AMLL) and 7.4±1.8% (for RB1) (FIG. 8a and Table third row). The combined data of losses and gains (mean value of AML1, RB1, CEN17 and CEN15) for each sample in the hematological malignancy group, except one, ranged from 11.4–18.4%, a range notably higher than that found in the group of the non-cancerous samples (ranging 4.2–8.4%). The single sample in the malignant group that displayed a low value displayed a value of 8.9%, still higher than the values obtained in the non-cancerous samples.

The increased tendency in the malignant samples for chromosome instability was manifested in both, the levels of cells disclosing losses of one copy of AML1, CEN17 and CEN15 as well as in the levels of cells displaying three or more copies of each of the tested loci (AML1, RB1, CEN17 and CEN15) (FIGS. 8b and c and Table 9, row 4 and 5).

Figure 9:
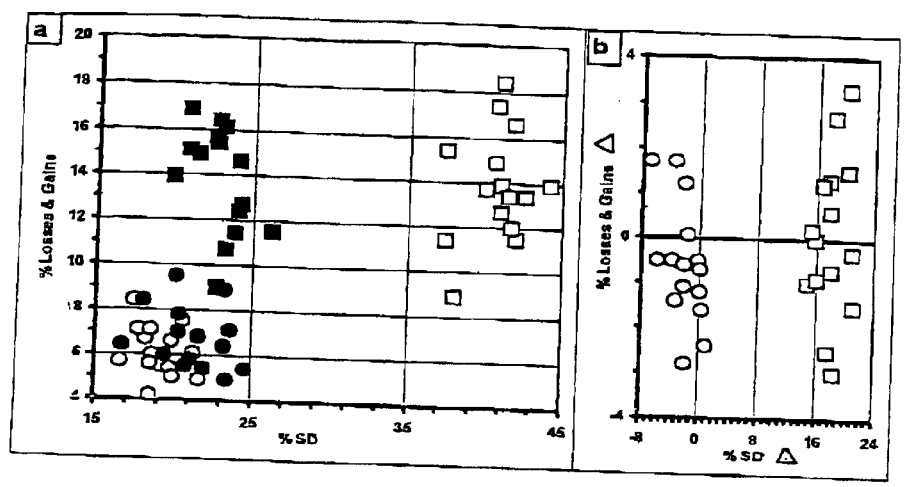
FIGS. 9A and B are graphs showing the correlation between levels of a synchrony in replication timing of allelic sequences and frequency of cells with chromosome losses and gains in cancerous and noncancerous samples.

Chromosome losses and gains, in contrast to allele specific replication, manifest a permanent and non-reversible damage that cannot be adjusted in the presence of the demethylating agent (FIGS. 8 and 9).

More specifically, FIG. 1 shows PHA-stimulated lymphocytes following one-color hybridization with a locus specific probe. In FIG. 1A there is shown a cell with one singlet and one doublet (SD cell) representing S-phase cells where only one of the allelic sequences has replicated. FIG. 1B shows a cell with two singlets (SS cell) representing cells in which both allelic sequences are not yet replicated. A cell with two doublets (DD cell) representing cells in which both allelic sequences have replicated is shown in FIG. 1C.

FIG. 8 shows the mean and standard deviation of the frequency (%) of cells exhibiting the SD (FIG. 7a), SS (FIG. 7b) and DD (FIG. 7c) pattern of replication of the designated loci. Empty bars represent non-cancerous samples grown in the absence of 5-azacytidine (AZA). Striped bars represent non-cancerous samples grown in the presence of AZA. Solid bars represent cancerous samples grown in the absence of AZA. Dotted bars represent cancerous samples grown in the presence of AZA. For information about statistical significance please refer to Table 8 and the first and second row in Table 9.

In FIG. 8 there is shown the mean and standard deviation of the frequency (%) of cells exhibiting losses and gains for chromosome 21 chromosome 13, chromosome 17 and chromosome 15, identified by AML1, RB1, CEN17, and CEN15, respectively. Empty bars represent non-cancerous samples grown in the absence of 5-azacytidine (AZA). Striped bars represent non-cancerous samples grown in the presence of AZA. Solid bars represent cancerous samples grown in the absence of AZA. Dotted bars represent cancerous samples grown in the presence of AZA. For information about statistical significance please refer to rows 3–5 in Table 9.

FIG. 9 shows the correlation between levels of asynchrony in replication timing of allelic sequences (SD cell frequency) and frequency of cells with chromosome losses and gains in 15 cancerous samples (samples 1–15 presented by squares) and in 15 non-cancerous samples (samples 16–30 presented by circles). The mean SD value of five loci (TP53, AML1, RB1, CEN17 and CEN15) and the mean losses and gains value of four loci (AML1, RB1, CEN17 and CEN15) represent each sample. In frame (FIG. 9a) each sample is presented twice by its value in the absence (empty figures) and in the presence (solid figures) of 5-azacytidine (AZA). In frame (FIG. 9b) each sample is presented only once by the subtraction (Δ) of its value obtained in the presence of AZA from the corresponding one achieved in the absence of AZA. While the presence of AZA did not affect the non-cancerous samples it affected the cancerous samples, leading to decrease in the SD values toward the normal ones leaving losses and gains values unchanged.

EXAMPLE 7

Samples

Peripheral blood samples obtained from 30 patients diagnosed with prostate cancer (CAP), and from 27 subjects who suffered from benign prostate hyperplasia (BPH) were used. All samples were obtained at presentation prior to any medical treatment, and the diagnosis was later established and verified by tissue assessment.

The age of the CAP patients ranged between 52–88 years and that of the PBH subjects between 53–86 years, with mean and standard deviation values of 70.8±8.0 and 69.6±9.6 years, respectively.

Cultures

Each sample was set up for short-term culturing in F10 medium supplemented with 20% fetal calf serum (FCS), 3% phytohemagglutinin (PHA), 0.2% heparin, and 1% antibiotics (a standard solution of penicillin and streptomycin). Cultures were incubated at 37° C. for 72 hours and then colchicine (final concentration 0.1 μg/ml) was added to the culture for one hour, followed by hypotonic treatment (0.075 M KCl at 37° C. for 15 minutes) and four washes each with a fresh cold 3:1 methanol: acetic acid solution. The cell suspensions were stored at −20° C. until used for fluorescence in situ hybridization (FISH). Six samples out of the 30 samples derived from the CAP patients and six out of the 27 samples of the BPH subjects (randomly selected), in addition to being grown in the medium described above, were exposed to $10^{-7}$M 5-azacytidine (AZA; Sigma, USA) added as a supplement to the other ingredients of the medium.

Probes

Six directly labeled commercial probes obtained from Vysis (USA) were used, these probes are as follows: AML1 (32-190002), TP53 (32-190008), CMYC (32-190006), RB81 (32-190001) D15Z1 (32-1300015) and SNRPN (32-190004). The AML1 probe identifies the 21q22 region of the transcription factor AML1/1CBFA2, involved in various malignancies. The TP53 probe identifies the p53 gene which is a tumor suppressor gene mapped to 17q13.1. The CMYC probe recognizes a well investigated oncogene mapped to 8q24. The RB1 recognizes the most common tumor suppressor gene mapped to 13q14, whose loss gave rise to the Knudson's two-hit theory about cancer development. The D15Z1 identifies the satellite region of chromosome 15, a sequence lacking transcriptional capability, associated with chromosomal stability and as such used for enumeration of chromosome 15; the SNRPN probe identifies a locus located within the most investigated imprinted region in man (15q11–13).

Of the 30 samples obtained from the CAP patients, 26 were hybridized with the AML1 probe and 24 with the TP53 and of the 27 samples of the BPH subjects 24 were hybridized with AML1 and 20 with TP53. In addition, 12 samples (six out of the 27 PBH samples and six out of the 30 CAP samples) which were grown in the presence, as well as in the absence of AZA were also hybridized with the RB1, D15Z1 and SNRPN probes.

Fluorescence in situ Hybridization (FISH)

Slide preparation, in situ hybridization, post washing and detection were performed in accordance with the protocol of Insitus Biotechnologies (previously Ingen Biotechnologies, USA), with slight modifications. Accordingly, probes were diluted 1:100 (AML1, RB1), 1:50 (TP53, CMYC and SNRPN) in D003 or 1:400 (D15Z1) in D001 Ingen's Den-Hyb hybridization solutions (instead of the hybridization solution supplied with the probe). Five $\mu$l of the probe solution are placed on the targeted area of the sample slides and covered with a 12 mm round silanized coverslip (Ingen Laboratories, USA, and currently Insitus Biotechnologies) and then sealed with rubber cement. The slides were placed into a microheating system (True Temp; Robbins Scientific, USA) at 76° C. and denatured for six minutes at that temperature. Then the True Temp was turned off, and the slides were allowed to hybridize overnight in the instrument.

Cytogenetic Evaluation

Slides were analyzed blindly on an Olympus BH2 fluorescent microscope, using a triple band-pass filter (Chroma technology). For replication analyses, at least 100 cells (in most cases 200 cells) exhibiting two distinct well defined fluorescence signals were scored from each sample for each treatment and for each tested probe. Signals were divided into two categories: a single dot (singlet; S) representing an unreplicated sequence and a doubled dot (doublet; D) indicating that the sequence has already replicated. Thus, cells appeared to carry either two synchronous signals (SS and DD) or two asynchronous signals (SD; FIG. 1). For each sample and for each treatment the frequency of SD, SS and DD cells out of the total population of cells containing two fluorescent signals was recorded (for details please see Dotan et al, Genes, Chromosomes & Cancer 27:270–277, 2000). For the determination of allelic losses at least 200 cells from the same preparation used for replication studied were analyzed for each tested sample.

Statistical Analysis

The statistical significance of the differences between two populations tested was carried out using the two-tailed Student's t-test (Microsoft Excel).

Results

Allelic Replication Mode in Blood Cells Differentiates Between CAP Patients and BPH Subjects The frequencies of SD cells for AML1 and TP53 loci in samples derived from patients diagnosed with CAP were significantly higher than the corresponding values obtained in samples of BPH subjects ($P<10^{-13}$ for TP53, respectively). Specifically, in the patient samples (CAP samples) the SD cell frequency values ranged from 23–43% for AML1, and from 18–42% for TP53 with mean and standard deviation values of 31.3±4.8% and 32.0±6.5%, respectively. Whereas, the SD values in the samples obtained from BPH subjects (BPH samples) ranged from 6–20% for AML1, and from 8–221% for TP53, with mean and standard deviation values of 13.4±3.2% and 13.1±3.6%, respectively (FIGS. 6a and b).

Evidently, in each group of samples the SD frequencies displayed by AML1 and TP53 were similar (P>0.60 for CAP samples and P>0.70 for BPH samples; compare FIGS. 10a and b). However, the two loci differ highly in the frequency of the corresponding values of SS cells ($P<10^{-14}$ for BPH samples and $P<10^{-8}$ for CAP samples) and of DD cells ($P<10^{-13}$ and $P<10^{-6}$, respectively). In each group of samples the SS cell frequency for the AML1 was smaller than that of TP53 (FIGS. 6c and d) while the corresponding DD value was larger (FIGS. 10e and f). Thus, indicating that in PBH samples, as well as in CAP samples, the AML1 locus initiates and terminates its replication prior to the TP53 locus.

It is worthwhile mentioning that the increased SD cell frequency obtained for the AML1 locus in the CAP samples, compared to that observed for the same locus in the BPH samples, arises from a decrease in the DD cell frequency (FIG. 10e) and not in the SS frequency (FIG. 10c). The increased SD cell frequency for the TP53 shown in the CAP samples mostly originated from a decrease in the SS frequency (FIG. 10d) and not in the DD (FIG. 10f). Thus, pointing to a cancer-dependent phenomenon leading to a delay in replication timing of a single allele of the early replicating locus (AML1), and to an advanced replication timing of a single allele of the late replicating locus (TP53).

In order to investigate further the locus specificity of the cancer induced allele-specific replication timing, four additional loci, CMYC, RB1, D15Z1 and SNRPN, were analyzed using six samples randomly selected from the 27 BPH samples (PBH samples 1–6) and six from the 30 CAP samples (CAP samples 1–6). As judged from the frequency of SS and DD cells in BPH samples, CMYC replicates late (similar to TP53), RB1 replicates early (similar to AML1), D15Z1 replicates later than D21S55 and earlier than TP53, and the SNRPN starts to replicate early with AMLA1 and terminates late with TP53 (FIG. 1a). Thus, the added loci, when present in cells not associated with malignancy, exemplify loci occupying different replication domains of the S-phase. However, all four added loci similar to AML1 and TP53, when present in the cells of the CAP patients changed their mode of replication (FIGS. 11a–b and solid bars in FIG. 12).

Specifically, CMYC, RB1 and D15Z1 all displayed high frequencies of SD cells in the CAP samples (ranging between 24–42% for CMYC, 27–38% for RB1 and 30–39% for D15Z1) and significantly lower ($P<10^{-3}$ for CMYC and $P<10^{-5}$ for RB1 and D15Z1) values in BPH samples (ranging from 7–20% for CMYC, from 8–16% for RB1 and from 10–22% for D15Z1). The corresponding means were 20.3±6.7% vs. 12.2±5.0% for CMYC, 32.0±4.2% vs. 10.8±3.0% for RB1 and 34.7±3.8% vs. 14.2±4.6% for D15Z1 (FIGS. 1a–b and solid bars in FIGS. 7a–j). Evidently, the CMYC, RB1 and D15Z1 SD values in blood cells, similarly to the corresponding values of TP53 and AML1, highly differentiate between CAP patients and BPH subjects (please follow the solid bars in FIGS. 12a–j).

Moreover, the SNRPN imprinted locus, which in BPH samples displayed a high frequency of SD cells (ranging from 32–42% with a mean of 39.2±3.9%), when present in cells of CAP patients drastically changed its replication mode (FIGS. 11a–b). The imprinted locus in the CAP samples revealed a significantly ($P<10^{-5}$) lower frequency of SD cells (ranging from 22–26% with a mean of 23.5±1.8%) compared to the level observed for this locus in the BPH samples (please follow the solid bars in FIGS. 12k–l). However, this reduced value of SD observed in CAP samples is still significantly higher ($P<10^{-3}$ for AML1, TP53, CMYC, and D15Z1, and $P<10^{-5}$ for RB1) compared to the SD values observed in BPH samples for the non-imprinted loci (FIGS. 11a–b, and solid bars in FIG. 12).

Figure 11:
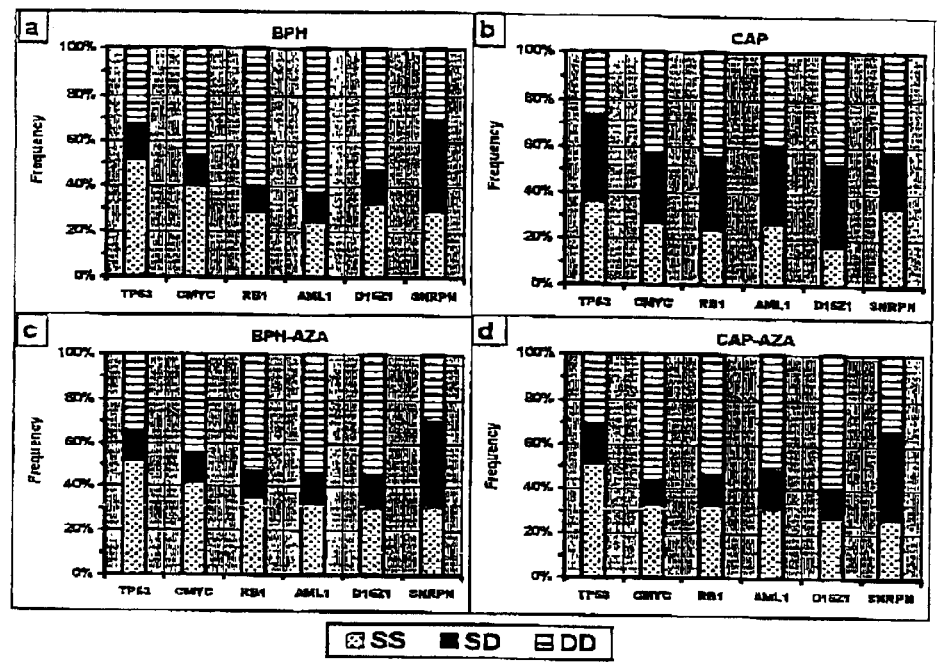
FIGS. 11A–D are graphs showing the mean frequency of the designated loci of SS cells, SD cells and DD cells in lymphocytes of prostate cancer patients (CAP) and control subjects (BPH) in the presence and absence of an agent associated with gene expression (AZA)
Figure 12:
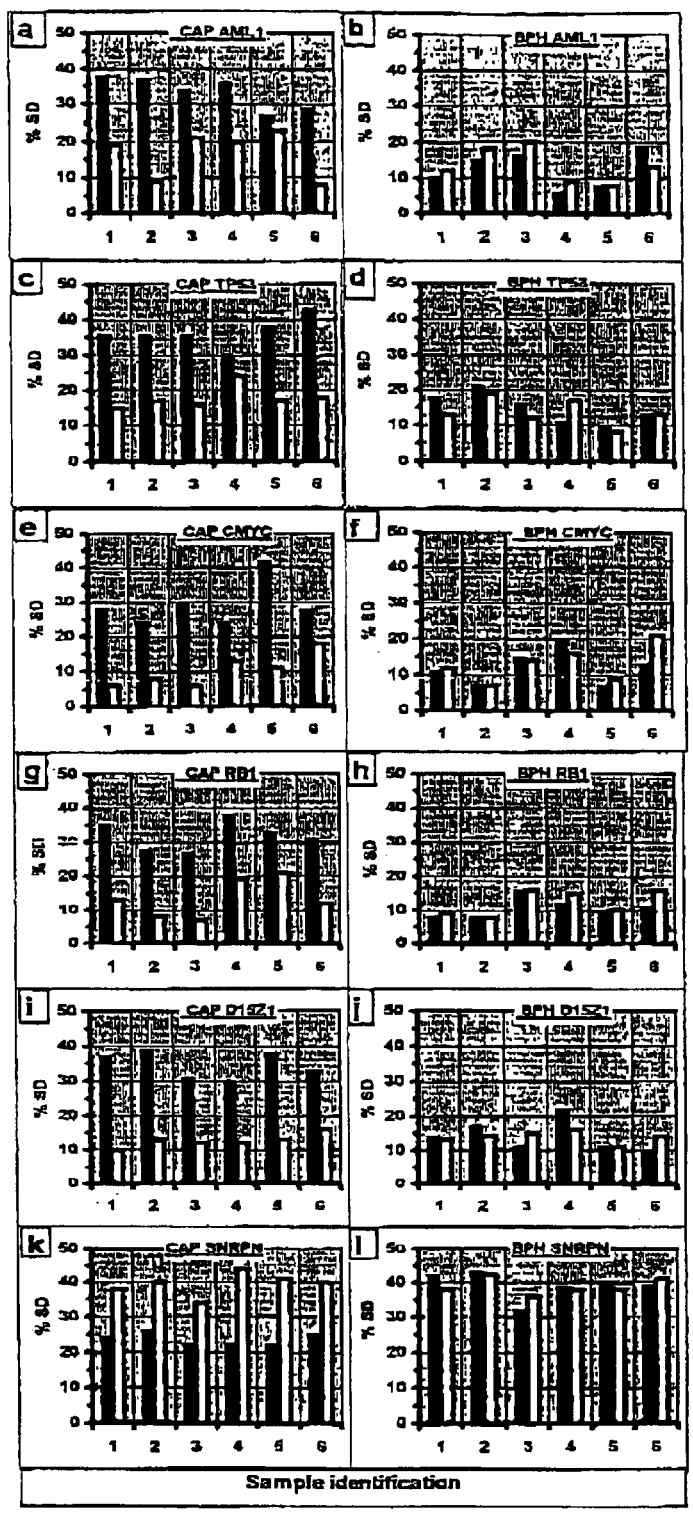
FIGS. 12A–L are graphs showing the frequency (%) of SD cells for: four biallelicaly expressed loci (AML1, TP53, CMYC and RB1), anon-coding satellited locus (D15Z) and a monoallelicaly expressed locus (SNRPN), in the presence (solid bars) and in the absence (empty bars) of a demthylating agent (AZA) in lymphocytes of prostate cancer patients (CAP) and control subjects (BPH).

It is worthwhile mentioning that the high SD values observed in the CAP samples for AML1, TP53, CMYC, RB1 and D15Z1 almost similar ($P>0.01$ for all five loci) to the values characterizing the SNRPN imprinted locus in BPH samples (FIGS. 11a–b, and solid bars in FIG. 12).

Loss of an Allele Characterizes Blood Cells of CAP Patients

The frequencies of cells displaying loss of one copy of an identified locus, loss of an allele, in the CAP samples was significantly higher ($P<10^{-10}$ for AML1 and $P<10^{-12}$ for TP53) than the corresponding values shown in the PBH samples. In the CAP samples the frequency of cells displaying loss of one copy of AML1 ranged between 4.5–14.0% and of TP53 between 2.0–15.5% with means and standard deviation values of 8.0±2.6% and 10.9±3.3%, respectively. While in the BPH samples the frequencies of cells with loss of one copy of a locus ranged between 1.5–6% for AML1 and 0–5% for TP53, with mean values of 3.0±1.2% and 2.7±1.3%, respectively (FIGS. 10g and h).

An increased frequency of cells displaying loss of one copy of CMYC (ranging between 6.0–9.0% with a mean of 7.2±1.3%, RB1 (ranging between 3.5–11.0% with a mean of 7.8±2.6%) and D15Z1 (ranging between 8.5–12.0% with a mean of 10.4±1.2%) was observed in the six CAP samples hybridized with CMYC, RB1 and D15Z1 probes. The corresponding values in the six BPH samples were significantly lower ($P<10^{-5}$ for CMYC, $P<10^{-3}$ for RB1 and P<10-6 for D15Z1 (ranging 2.0–3.0% for CMYC, 1.5–4.0% for RB1 and 3.0–3.5% for D15Z1 with mean values of 2.3±0.4%, 2.8±0.9% and 3.3%, respectively) (please follow the solid bars in FIG. 13).

Allelic Loci in Cells of CAP Patients Grown in the Presence of 5-azacytidine (AZA) Replicate in a Pattern Similar to that of BPH Subjects The cancer-dependent phenomenon leading to a drastic modification in the SD cell frequency observed for all the six tested loci, AML1, TP53, CMYC, RB1, D15Z1 and SNRPN is reversible as it could be erased in the presence of a demethylating agent, 5-azacytidine (AZA) (FIGS. 11 and 12). When the cell samples of the CAP patients were cultured in the presence of AZA, they displayed SD cell frequencies for all tested loci (AML1, TP53, CMYC, RB1, D15Z1 as well as for SNRPN) similar to those obtained in BPH samples (FIGS. 8 and 9). Thus, SD values in the patient samples following AZA treatment became significantly lower for AML1, TP53, CMYC, RB1 and D15Z1 ($P<10^{-3}$, $P<10^{-5}$, $P<10^{-4}$ and $P<10^{-5}$, respectively), as compared to the values obtained in the very same samples grown in the absence of AZA. However, the corresponding SD values for SNRPN in the CAP samples increased significantly ($P<10^{-5}$), following the AZA treatment.

The presence of AZA had no significant effect on the SD values obtained in the BPH samples (FIGS. 11 and 12).

However, in contrast to the SD frequency which appears to be a reversible trait as it regains normal levels in the CAP sample following AZA, the accompanying phenomenon of allelic loss is permanent and independent of the presence of the demethylating agent (FIG. 12).

More specifically, FIG. 1 shows lymphocytes following FISH with the AML1 probe. A cell with one singlet and one doublet (SD) representing S-phase cells where only one of the allelic sequences has replicated is shown in FIG. 1. A cell with two singlets (SS) representing cells in which both alleles have not yet replicated is shown in FIG. 5B. FIG. 5C shows a cell with two doublets (DD) representing cells in which both alleles have replicated.

Figure 10:
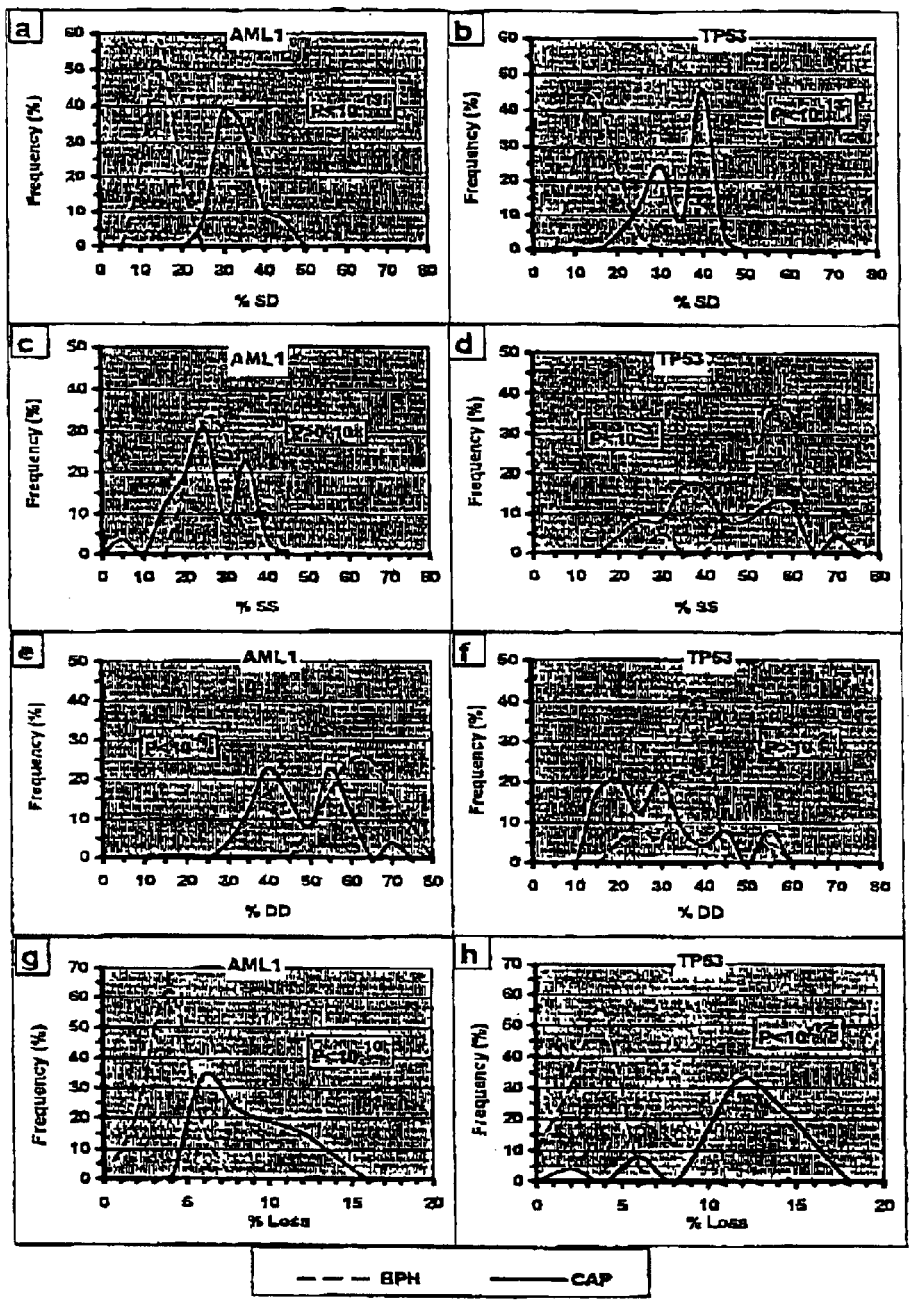
FIGS. 10A–H are graphs showing the frequency distribution of cells exhibiting various pattern of replications and losses for the AML1 and TP53 loci in cells of individuals suffering from prostate cancer (solid lines) and in cells of control individual (doted lines)

FIG. 10 shows the frequency distribution of cells exhibiting various pattern of replications for the AML1 and TP53 loci in samples derived from prostate cancer patients (CAP) and subjects suffering from benign prostate hyperplasia BPH). The SD pattern is presented in FIG. 12a and FIG. 10b. The SS in FIG. 10c and FIG. 10d and the DD in FIG. 10e and FIG. 10f. The frequency of cells displaying a loss of one copy of the AML1 and of the TP53 locus are presented in FIG. 10g and FIG. 10h, respectively.

FIG. 11 shows the mean frequency of six subjects suffering from benign prostate hyperplasia (BPH samples 1–6) and six prostate cancer patients (CAP samples 1–6) for the designated loci of SS cells (dotted bars), SD cells (solid bars) and DD cells striped bars). The values presented in FIGS. 1a and b were obtained in the absence of a demethylating agent (5-azacytidine; AZA), while FIGS. 11c and d present values obtained in the presence of AZA.

FIG. 12 shows the frequency (%) of SD cells for AML1, TP53, CMYC, RB1, D15Z1 and SNRPN in samples of prostate cancer patients (CAP samples 1–6) and in samples of subjects suffering from benign prostate hyperplasia (BPH samples 1–6). The solid bars represent values obtained in the absence of a methylating agent (5-azacytidine; AZA), while empty bars represent values obtained in the absence of a methylating agent (5-azacytidine; AZA), while empty bars represent values obtained in the presence of AZA. There is a reversible change caused by AZA to the CAP samples, while leaving the BPH samples unchanged.

Figure 13:
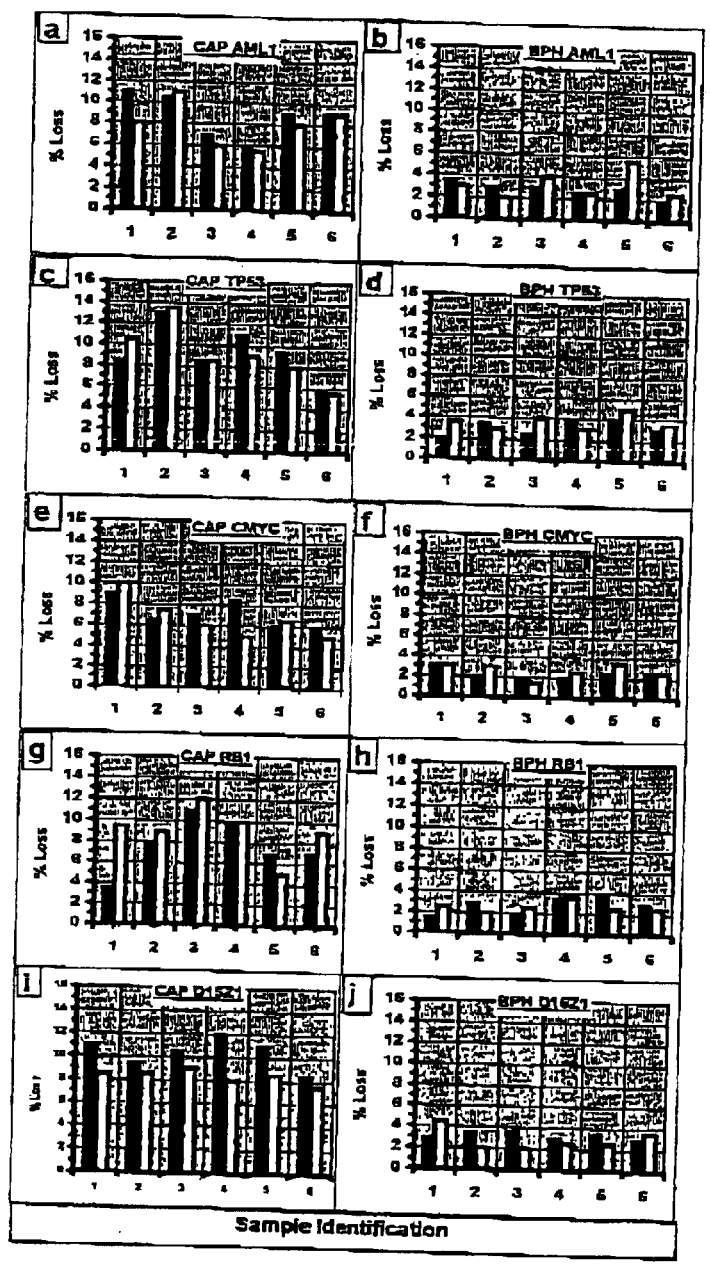
FIGS. 13A–L are graphs showing the frequency (%) of cells showing a loss of one copy of AML1, TP53, CMYC, RB1, D15Z1 and SNRPN in the presence (solid bars) and absence (empty bars) of a demethylating agent (AZA) in lymphocytes of prostate cancer patients (CAP) and control subjects (BPH)

FIG. 13 shows the frequency (%) of cells showing a loss of one copy of AML1, TP53, CMYC, RB1, D15Z1 and SNRPN in samples of prostate cancer patients (CAP samples 1–6) and in samples of subjects suffering from benign prostate hyperplasia (BPH samples 1–6). The solid bars present values obtained in the absence of a methylating agent (5-azacytidine; AZA), while empty bars present values obtained in the presence of AZA. Neither the CAP samples nor the BPH samples were affected by AZA.

EXAMPLE 8

Whether exposure to weak, extremely low frequency electromagnetic fields (EMFs) produced by power lines and industrial appliances is a factor associated with an increased risk for cancer is still under intensive debate (1,2). Some epidemiological studies have described a weak correlation between EMFs and increased risk for cancer, particularly blood malignancies and various brain tumors (3–5). Recently it became evident that increased risk for cancer is associated with two distinct types of genetic instability, one originating from modification at the nucleotide level and the other from alteration at the chromosomal level (shown by abnormal chromosome number; aneuploidy). The former is only observed in a small portion of malignancies, whereas chromosomal instability (CIN) underlies the majority of cancers (6,7). Evidently, CIN is a consequence of a defect in one of the components responsible for normal chromosome segregation (8). Here, there is demonstrated an increased level of aneuploidy, accompanied by an alteration in the behavior of the centromere, a chromosome built-in movercomponent (9), in peripheral blood lymphocytes (PBLs) of individuals occupationally exposed to EMFs as well as in PBLs exposed to EMFs in-vitro. An increased level of aneuploidy coupled with the same alteration in the apparatus in PBLs of patients suffering from various blood malignancies has also been observed.

CIN leads to loss of one allele in many genetic loci, a phenomenon widely known to accompany cancer initiation and referred to as loss of heterozygosity (10). Concomitantly, it increases gene dosage, another phenomenon often observed in cancer (11). Thus, CIN does not merely describe the status of aneuploidy acquired by a single sporadic event, but appears to be an alternative mechanism, to the ineffective mismatch repair mechanism, for driving tumor initiation and progression (6,8). CIN being a process generating losses and gains of whole chromosomes is necessarily coupled with some defect in the chromosome segregation apparatus. Indeed, in cells of children suffering from various types of malignancies (12) and in some colon cancer cell lines, increased levels of aneuploidy were coupled with an abnormality of the mitotic apparatus expressed through decreased sensitivity to antimitotic drugs (13–15). Similarly, in cells of females suffering from familial ovarian cancer increased levels of aneuploidy were associated with asynchrony in replication timing of homologous α-satellite DNA arrays (16), which in men constitute the main DNA of the centromeres (9).

Here, an approach was applied in which the consequences of being exposed in vivo, as well as in vitro, to EMFs are monitored by analyzing both the frequency of losses and gains of two chromosomes and the level of asynchrony in replication timing of homologous a-satellite arrays of the very same chromosomes. Human phytohemagglutinin (PHA) stimulated PBLs were used in the experiment, which most closely represent the normal counterparts of blood malignant cells and provide a highly sensitive system for detecting visible chromosome alterations induced by exposure to environmental genotoxic insults (17–19). The EMFs exposed PBLs were compared to PBLs obtained from both unexposed healthy subjects and patients suffering from blood malignancies. The chromosomes chosen were chromosomes 10 and 17, each accommodating a well-known tumor suppressor gene (PTEN and TP53, respectively). The loss of one copy of the PTEN gene is implicated in brain cancer (20) while deletion of one TP53 allele coupled with mutation of the other is found in 50% of all human cancers, including blood malignancies (21).

Losses and gains of chromosomes 10 and 17 were investigated using a powerful molecular cytogenetic technique, based on fluorescence in situ hybridization (FISH). This method enables the detection of the copy number of a given chromosome in interphase cells and thus facilitates the screening of a large cell population from a single preparation (22, 23). Accordingly, a given chromosome is identified by its chromosome-specific α-satellite DNA probe (9, 16, 24). Furthermore, this assay enables the detection of the level of asynchrony in replication timing of homologous α-satellite DNA in the same cell preparations used for the detection of chromosome losses and gains (16).

Materials and Methods

Samples

Peripheral blood samples of 21 occupationally exposed (OE) male workers and 31 age matched males comprising two groups of subjects: 21 control individuals, not occupationally exposed to EMFs (CO) and 10 individuals suffering from various types of hematological malignancies, examined at diagnosis prior to any clinical treatment (HM), were used. All the OE samples and the CO samples were grown in duplicates in the common employed medium used for karyotype analysis, one of each was exposed in vitro to EMFs for 10 hours (designated "OE⁺" and "CO⁺", respectively), while the other was grown with no interruption (designated CO, and OE, respectively).

Culture Preparation

Each culture was set up using 0.3 ml of blood added to a 75-ml flask (Corning) containing 5 ml of a medium described previously (16). The in vitro unexposed samples were grown, uninterrupted, in a 37±0.1° C. incubator for a time duration of 69–72 hours as described previously (16). The in vitro exposed samples were placed in an experimental set up (please see the next paragraph). The system was turned on 6–7 hours after culture set up for ten hours and then the cultures remained uninterrupted for 52–55 hours at 37.0±0.10° C. until harvesting.

The harvesting and FISH procedures (slide preparation, hybridization, post washing and detection) for all cultures were performed as previously described (16).

In Vitro Exposure to Electromagnetic Fields

The in vitro exposure to EMFs was performed using a two Helmholtz coil exposure system (25). Accordingly, the flasks containing the cultures were positioned between two Helmholtz coils with their large area parallel to the plane of the coil. Each of the coils possessed 150 windings, 176 mm in diameter, distanced at 105 mm from each other with a total inductivity of 11.5 mH. The coils were placed in an incubator and connected directly to a high power pulse generator (Velonex 360F, Santa Clara, Calif.) with 200 Ohm output impedance. Application of a train of square unipolar pulses of 30 $\mu$s duration at a frequency of 50 Hz to the coils resulted in an almost linear rise of the current from 0 to 2.4 A during each pulse, as monitored continuously by a current probe. The calculated magnetic field induced between the coils in the vertical direction yields a peak value of 2.8 mT, which does not differ much from the value of 2.6 mT measured by an exploring coil (5 windings, 1.7 cm$^2$ section square; 26). This exposure level is equivalent to 32 $\mu$T in terms of root mean square (rms) which is much lower than the limit of 500 $\mu$T set for occupational exposure (27). The non-homogeneity of the peak field amplitude in the area where the samples were placed, surveyed by the exploring coil, was ±4% in vertial direction and ±15% in the horizontal plane. Since a minute warming ($\leq$0.3° C.) of the samples had been detected after ten hours of exposure, the temperature in the incuabor had been lowered to 36.7±0.1° C. to compensate for this small temperature rise. In a previous study, duplicate samples were placed in the same incubator at distance of 0.7 m from the coils as well as in a different incubator set at 37.0±0.1° C. There were no significant differences found between these samples. The electrical parameters and duration of exposure were chosen so as to mimic the chromosomal instability obtained under occupational exposure.

Probes

Two digoxigenin labeled commercial probes for the α-satellite centromeric DNA of chromosomes 10 (D10Z1) and 17 (D17Z1) were obtained from Oncor Inc., USA (P5020 and P5040, respectively).

Cytogenetic Evaluation

Slides were blindly scored as described previously (16). For the analysis of aneuploidy 200 cells were scored from each sample for each given chromosome. In each scored cell the copy number (number of FISH signals) of the identified chromosome was determined. Frequencies of chromosomal losses (monosomy levelZ) were determined by the frequency (%) of cells containing only a single hybridization signal of the tested chromosome. Similarly, frequencies of chromosomal gains (multisomy level) were obtained from the frequency (%) of cells with three or more signals. The freuqencies of losses and gains (aneuploidy level) were expressed by the combined frequency of monosomy and multisomy in a given sample. For the analysis of replication timing 100 cells, each containing two hybridization signals, were scored from each sample for each chromosome. Accordingly, an α-satellite array in the course of replication changes its conformation and displays differently shaped configurations, depending on its replication status (16). Thus, in a population of replicating cells, the frequency (%) of cells containing two dissimilar (unsynchronized) signals, following hybridization with an α-satellite probe, out of the total population of cells with two hybridization signals, represents the level of asynchrony in the replication of homologous α-satellite arrays.

Statistical Analysis

Statistical significance between two tested groups of samples was carried out using two-tailed Student's t-test (Microsoft Office 97, Excel).

Results and Discussion

Figure 14:
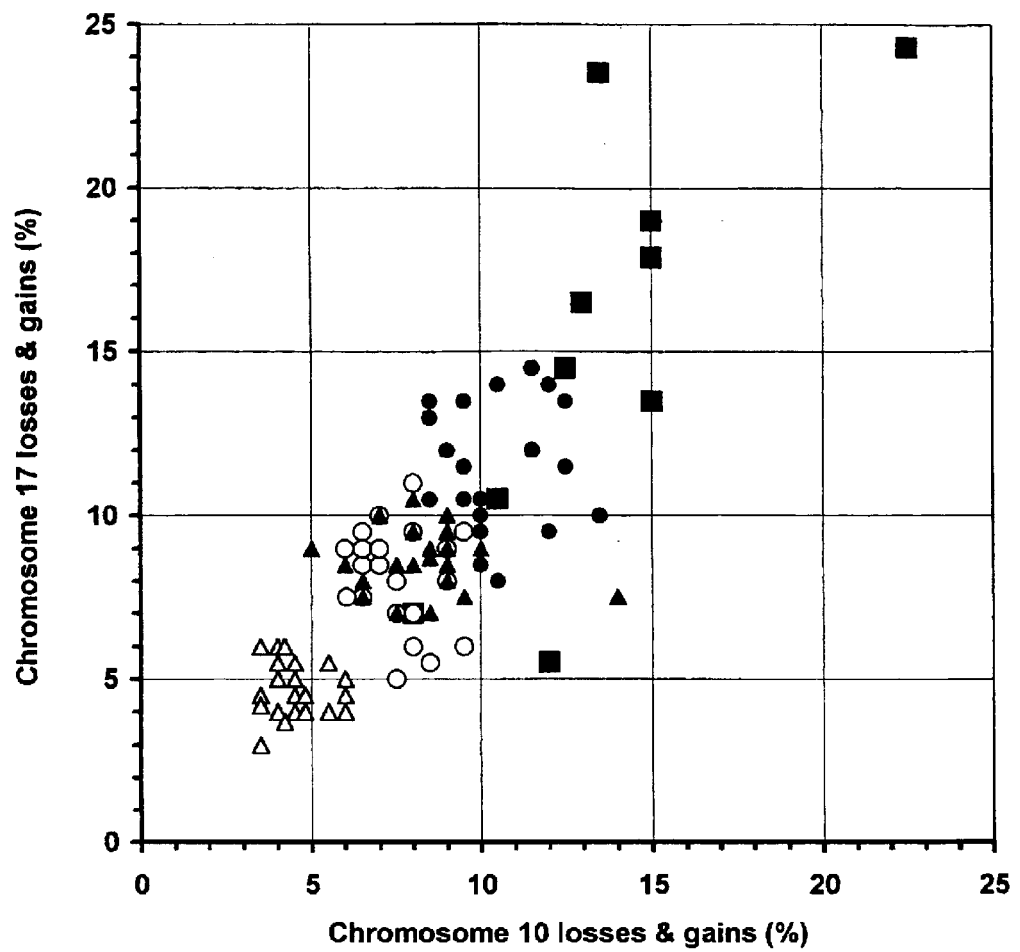
FIG. 14 is the frequency (%) of aneuploid cells of chromosomes 10 and 17 (total of cells with losses and gains for each chromosome) in each of the 94 PBL samples studied. Samples of individuals occupationally unexposed to EMFs (control samples) are designated -CO (empty triangles); samples of individuals occupationally exposed to EMFs are designated -OE (empty circles); samples of patients suffering from hematological malignancies are designated -HM (solid squares); samples of control individuals and occupational exposed individuals following in-vitro exposure are designated -CO$^+$ (solid triangles) and -OE$^+$ (solid circles), respectively.

The status of aneuploidy for chromosomes 10 and 17 in each of the 94 samples studied expressed in the total frequency (%) of losses and gains for each chromosome is presented in FIG. 14. In spite of the large variation revealed in aneuploidy levels in the various samples studied, a strong linear correlation (K=0.804) was observed between the aneuploidy status of chromosome 10 and 17 in the 94 samples studied. Thus suggesting that, whatever the mechanism leading to aneuploidy in those samples, it is not chromosome-specific and most probably affects other chromosomes from the human complement, as well.

Figure 15:
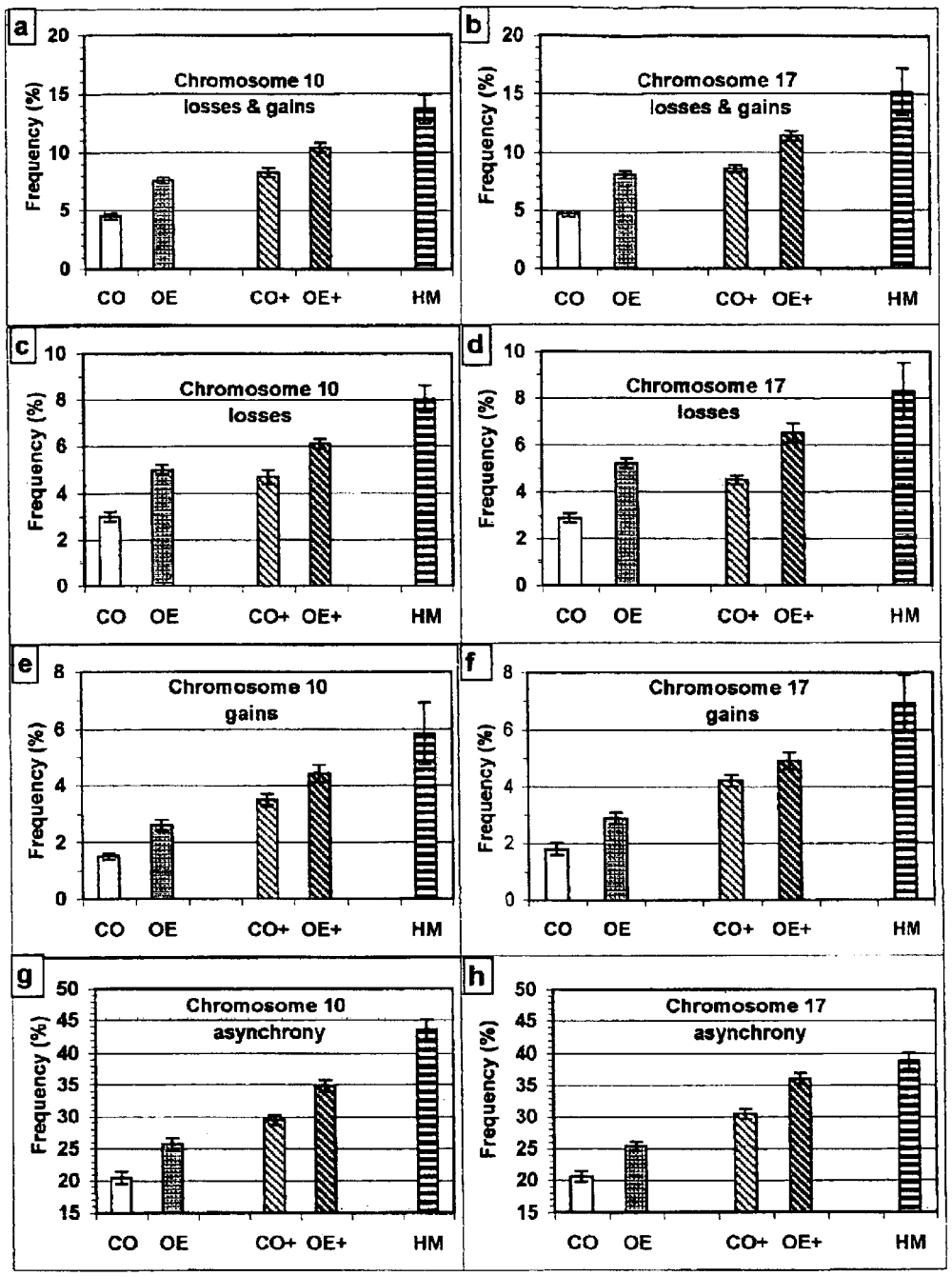
FIG. 15 is the means and standard error of the frequency (%) values of cells showing increased levels of aneuploidy and asynchrony in replication timing of α-satellite DNA arrays in various type of cell samples. Samples of individuals occupationally unexposed to EMFs (control samples) are designated -CO; samples of individuals occupationally exposed to EMFs are designated -OE; samples of patients suffering from hematological malignancies are designated -HM; samples of control individuals and occupational exposed individuals following in-vitro exposure are designated -CO$^+$ and -OE$^+$ respectively.

The analysis of the OE samples showed that the total level of losses and gains of chromosome 10 (mean of 7.6±0.2%) and 17 (mean of 8.1±0.3%) was significantly higher (p<10⁻ for chromosome 10, and $P<10^{-8}$, for chromosome 17) than in the CO samples (4.5±0.2% and 4.7±0.2%, respectively). However, the OE values were still lower ($P<10^{-3}$ for chromosome 10, and $P<10^{-2}$ for chromosome 17) than the corresponding values (means of 13.7±1.2% and 15.2±2.0% for chromosome 10 and 17, respectively) observed for the very same chromosomes in the HM samples Z (FIG. 15 and FIGS. 15a–b). The same holds true for both chromosome losses (monosomy; FIGS. 15c–d) and gains (multisomy; FIGS. 15–f. No differences were observed within each sample between the two chromosomes tested either in the monosomy or in the multisomy levels. The level of multisomy compared to that of monosomy was lower in all samples tested. However, the proportional increase in multisomy values found in the OE and HM samples compared to the CO samples was not lower than the corresponding increase shown in the monosomy levels (FIGS. 15c–f).

Aneuploidy levels, expressed by the total of losses and gains for both chromosomes, following in vitro exposure to EMF, increased significantly in the CO samples ($P<10^{-8}$ for chromosome 10 and $P<10^{-15}$ for chromosome 17) as well as in the OE samples ($P<10^{-7}$ and $P<10^{-8}$, respectively). In in vitro EMF effect is clearly reflected also at the monosomy and the multisomy levels (please compare first and third bar, and second and fourth bar, in frames a–f of FIG. 15). Furthermore, following in vitro exposure the aneuploidy levels of the OE samples and CO ones increased in a similar manner, although they significantly differed in their initial aneuplody levels (FIGS. 14 and 15a–f). In addition, in each of the in vitro exposed samples (CO and OE samples), as in the non-exposed ones (CO, OE and HM samples), no differences were observed between chromosomes 10 and 17 in the total aneuploidy level (FIGS. 15 and 15a–b). This is also true for the monosomy and multisomy levels (FIGS. 15c–f). The in vitro exposed CO samples (CO⁺) reaches aneuploidy levels similar to the corresponding values obtained in the in vivo exposed samples (OE). This is evident in the overlapping between CO⁺ and OE samples in FIG. 14 (compare also the second and third bar in FIGS. 15a–b).

Thus, the in vivo exposure can be mimicked by the in vitro EMF exposure system. In addition, the aneuploidy level of the occupationally exposed samples and the control ones increased in a similar manner following in vitro exposure. These results strongly suggest that aneuploidy, associated with EMFs, represents the rate of chromosome losses and gain rather than a state of deviation from the normal diploid number acquired by sporadic events not associated with a persistent defect in chromosome segregation. This is in agreement with the observations that colon and breast tumors, associated with genomic destabilization of the CIN type, usually show a low level of aneuploidy at initiation (benign tumors) which increases upon tumor progression into malignancy (6).

Furthermore, considering that following in vitro exposure to EMFs each of the exposed samples had gone through only a small number of generations, two or three at most, it appears that the risk for a chromosome to segregate abnormally following EMFs exposure is indeed high (about 1:100). This suggests again that EMFs affect one of the components associated with chromosome segregation. The results concerning the replication behavior of the centromere following EMFs exposure strongly support this suggestion (FIGS. 2g–h). The frequency of cells showing asynchrony in replication timing of homologous α-satellite arrays of chromosomes 10 and 17 in the CO⁺ samples (mean of 29.5±0.8% and 30.5±0.8%, respectively). Similarly, OE⁺ samples displayed significantly higher ($P<10^{-7}$ and $P<10^{-10}$) levels of cells with asynchrony in replication timing of homologous α-satellite arrays of chromosomes 10 and 17 (means of 34.8±0.9% and 36.035 0.9%, respectively) compared to OE samples (means of 25.8±0.9% and 25.4±0.7%, respectively). The OE⁺ replication values almost reached the corresponding values obtained in the HM samples (FIGS. 2g–h). Although the mean asynchrony value for chromosome 10 (43.5±1.5%) in the HM samples was still higher (P<10–3) then that observed in the OE+ samples, the value of chromosome 17 (38.8±1.3%) was similar (P=0.09) to the replication value of chromosome 17 in the OE⁺ samples. The asynchrony values of homologous α-satellite DNA in the OE samples was also significantly larger than that observed in the CO samples ($P<10^{-3}$, for both chromosomes, 10 and 17). However, the extent of the increase caused by in vivo exposure to EMFs was milder compared to the in vivo one (FIGS. 2g–h). These findings suggest that the memory of the segregation apparatus to the EMFs insult is relatively short. Thus, cells in a normal environment overcome the EMFs insult and adjust to the normal replication mode, leaving aneuploidy a long living defect, to increase the risk for carcinogenesis.

The mechanism by which exposure to EMFs affects the temporal order of the α-satellite DNA replication is not yet clear. However, there is evidence that it is not locus-specific as, it leads also to asynchrony in replication timing of homologous sequences of DNA possessing transcription ability, such as TP53 and HER2 (Mashevich et al. work in progress). Asynchronous replication of homologous sequences of cancer inducing genes which normally replicate highly synchronously, such as TP53, HER2, CMYC and AML1, was also observed in PBLs and bone marrow cells of patients diagnosed with various hematological malignancies (28). In those cells the asynchronous pattern of replication was reversed to the normal one in the presence of a demethylating agent (Korenstein et al. work in progress), thus suggesting that exposure to EMFs alters methylation/demethylation capacity, a common epigenetic phenomenon associated with cancer initiation and progression (29, 30). Moreover, the possibility that losses and gains of whole chromosomes observed here following exposure to EMFs are associated with alteration in the methylation process is in agreement with evidence obtained in colon cancer cell lines showing that CIN is accompanied by methylation abnormalities (31). Assuming that replication abnormalities arise from methylation|demethylation disturbances, it supports the results showing that replication asynchrony induced by exposure to EMFs is a short-living phenomenon, since the methylation process is reversible and can be easily adjusted following removal of the impediment. Yet, aneuploidy the consequence of the short-living insult causes a permanent damage to the lineage of an affected cell. However, the environment of normal cells, in contrast to that of malignant cells, usually does not support clonal expansion of an aneuploid cell (6). This explains the relatively low incidence of cancer in individuals environmentally exposed to EMFs, in spite of the increased levels of aneuploidy obtained following exposure to EMFs.

In conclusion, increased levels of aneuploidy, alteration in the behavior of a crucial component of the segregating apparatus and modification of the methylation capacity, are all features known to accompany genomic destabilization of the CIN type (14, 15, 31). It is rational to assume therefore that the genomic destabilization associated with hematological malignancies shown here is of the CIN type, as is the destabilization characterizing most solid tumors. Thus, blood cells at an increased risk to develop blood neoplasms are expected to show increased levels of aneuploidy coupled with abnormalities in one of the chromosome mover components. Such cells were found here to appear following both, in vivo and in vitro exposure to EMFs strongly supporting the view that exposure to EMFs provides an environmental factor, which increases the risk for genomic destabilization leading to cancer.

EXAMPLE 9

Figure 16:
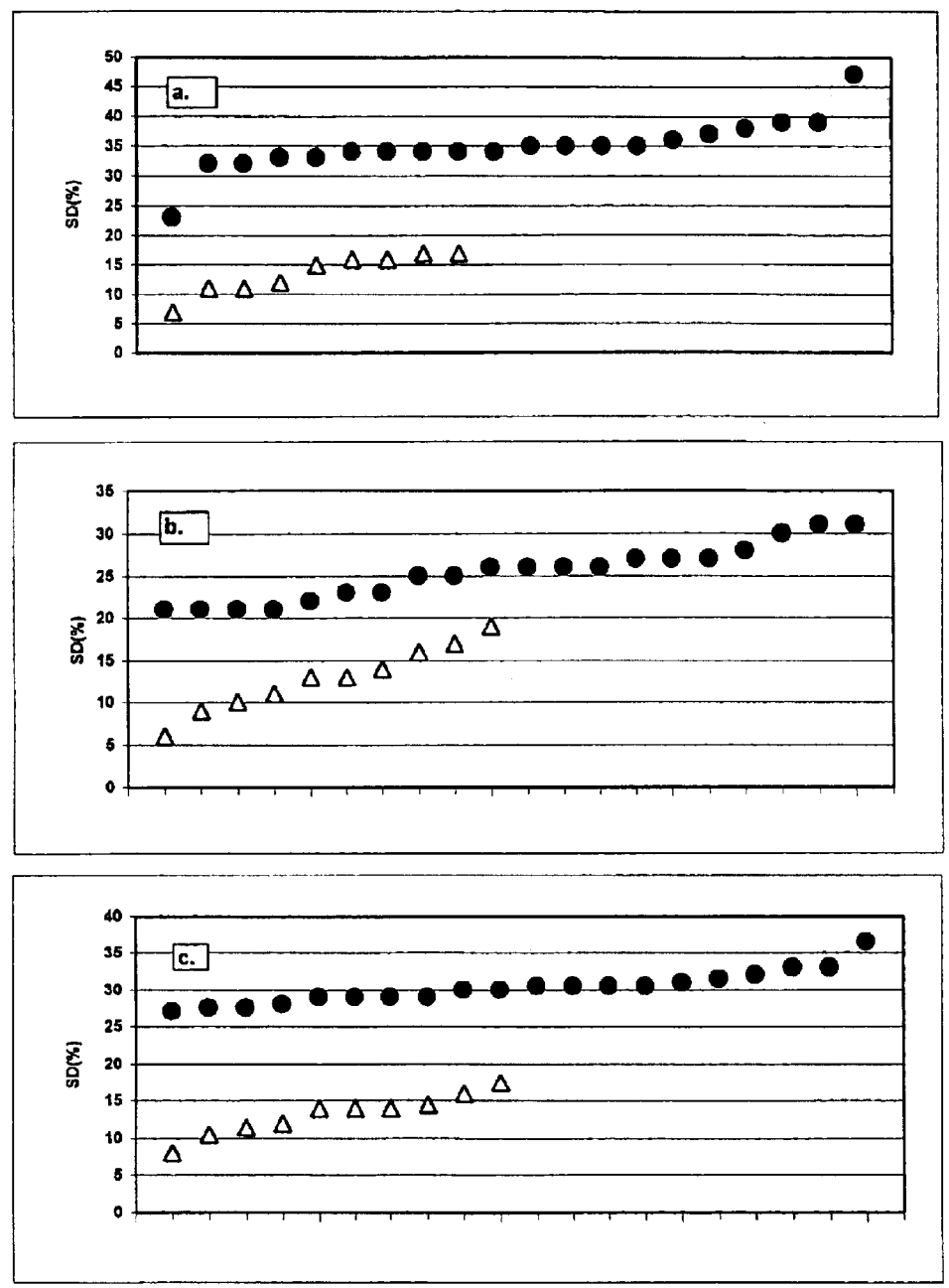
FIG. 16 shows frequency of SD cells arranged in increasing order of the BRC (circles) and CON (triangles) samples. a. HER2, b. D17Z1 and c. average of both loci.
Figure 17:
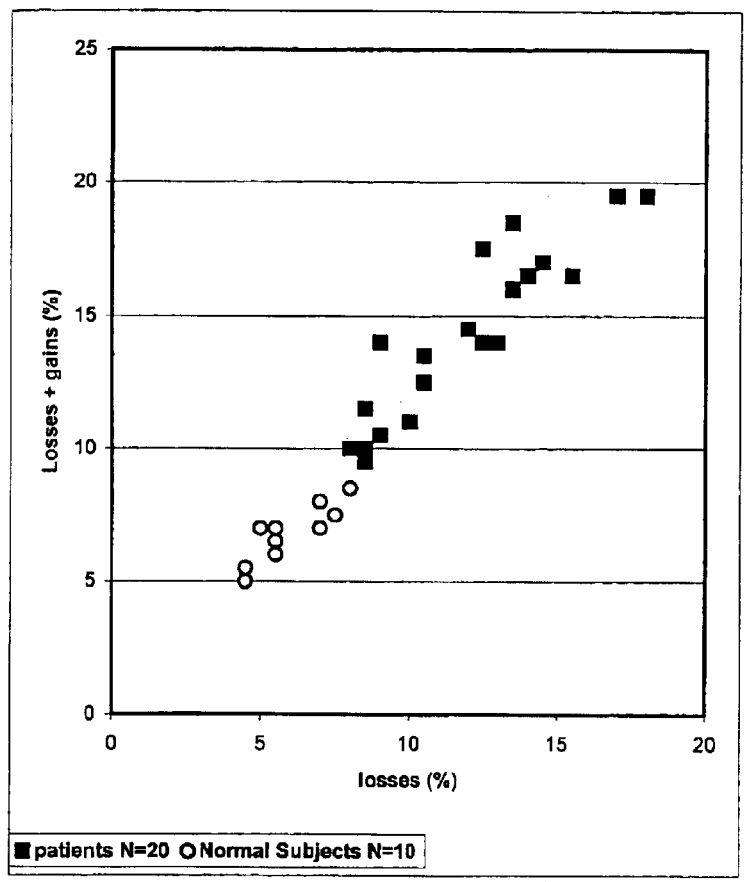
FIG. 17 shows frequency of chromosome 17 losses and total aneuploidy for the same chromosome (losses+gains) in CON and BRC lymphocytes. N=sample size.

The level of asynchrony in replication timing of two loci (HER2 and D17Z1) was studied in PHA stimulated lymphocytes of 20 females diagnosed with breast cancer (hereafter called BRC; samples 1–20) and of 10 healthy age matched females (hereafter called CON; samples 21–30). The HER2 gene is mapped to 17q 11.2–q12 and known to be amplified in breast cancer tumors and the D17Z1 is a non-coding centromeric sequence for the very same chromosome to which the HER2 gene was mapped (chromosome 17, marked as D17Z1). There was a highly significant difference in the level of asynchronous replication between two groups studied in each of the two loci ($p<10^{-13}$ and $p<10^{-9}$ for the HER2 and D17Z1 loci, respectively). The frequency of the SD cells in the BRC group was 35.0±0.98% for the HER2 locus and 35.5±0.7% for the D17Z1 locus. While the corresponding for the CON group were 13.6±1.03% and 13.0±1.25%, respectively (FIG. 16). Evidently, the SD values of coding as well as non-coding DNA sequences, when measured in lymphocytes differentiate between breast cancer patients and healthy females. In addition, asynchrony in the centromeric region of chromosome 17 was coupled with an increased rate of losses and gains of that chromosome. This is evident from the difference between the two groups of females in the total level of losses and gains of chromosome 17. The mean frequency of losses and gains was 14.3±0.72% in the BRC samples and significantly lower (6.8±0.3%; $p<10^{-6}$) in the CON samples (FIG. 17).

Figure 18:
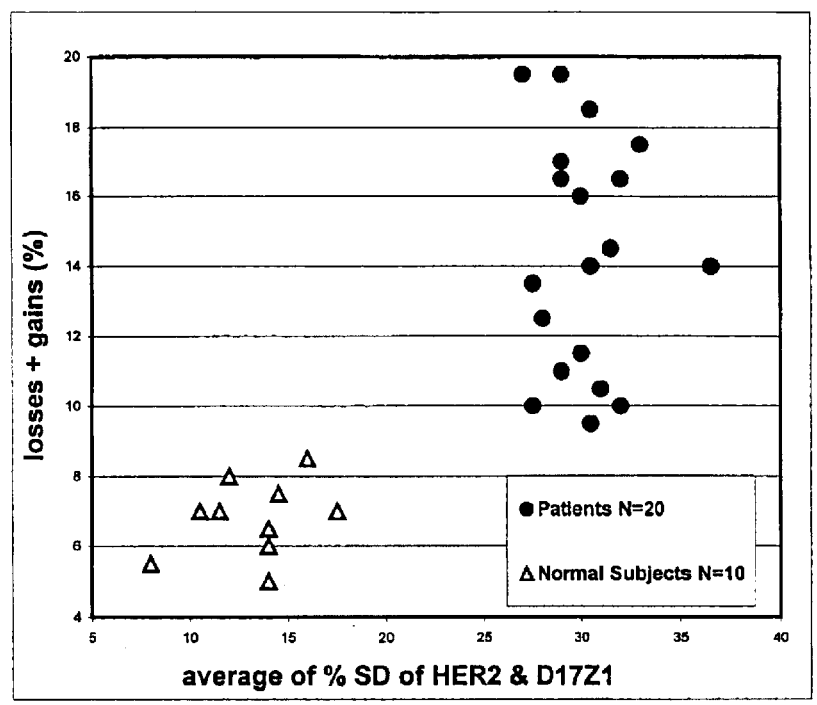
FIG. 18 shows the weighted mean of SD values obtained for both HER2 and D17Z1 loci as a function of losses+gains of chromosome 17.

The differentiation between the BRC and CON group is even more strongly evident when the combined SD frequency of both loci tested is plotted as a function of chromosomal losses plus gains (FIG. 18).

EXAMPLE 10

Cultures were set up from 44 healthy individuals (hereafter called CON) and 20 hematological malignancy patients at diagnosis (hereafter termed CAD). For 20 of the CON samples and all of the CAD samples peripheral in addition to the setting up cultures in the regular growth medium, cultures were set up in medium containing 5-azacytidine ($10^{-7}$M; Sigma, USA; hereafter referred to as AZA) a demethylating agent. In addition, cultures from 6 CON and 10 CAD samples were set up in medium containing a deacetylating agents, either Trichostatin A (33 nM; Sigma, USA; hereafter referred to as TSA) or Sodium Butirate (1 nM; Sigma, USA; hereafter referred to as NB), two well described acetylating agents.

These samples were hybridized with two commercial probes: the AML1 probe (LSI 21, 32-190001) and the α-satellite probe specific for centromere 17 (32-130017, hereafter marked as CEN17). The results are summarized in Table 1 giving the number of samples hybridized with each probe (N), Mean and standard deviation (stdev) as well as the p value obtained using two tailed student's t-test (Microsoft Office 98).

Figure 19:
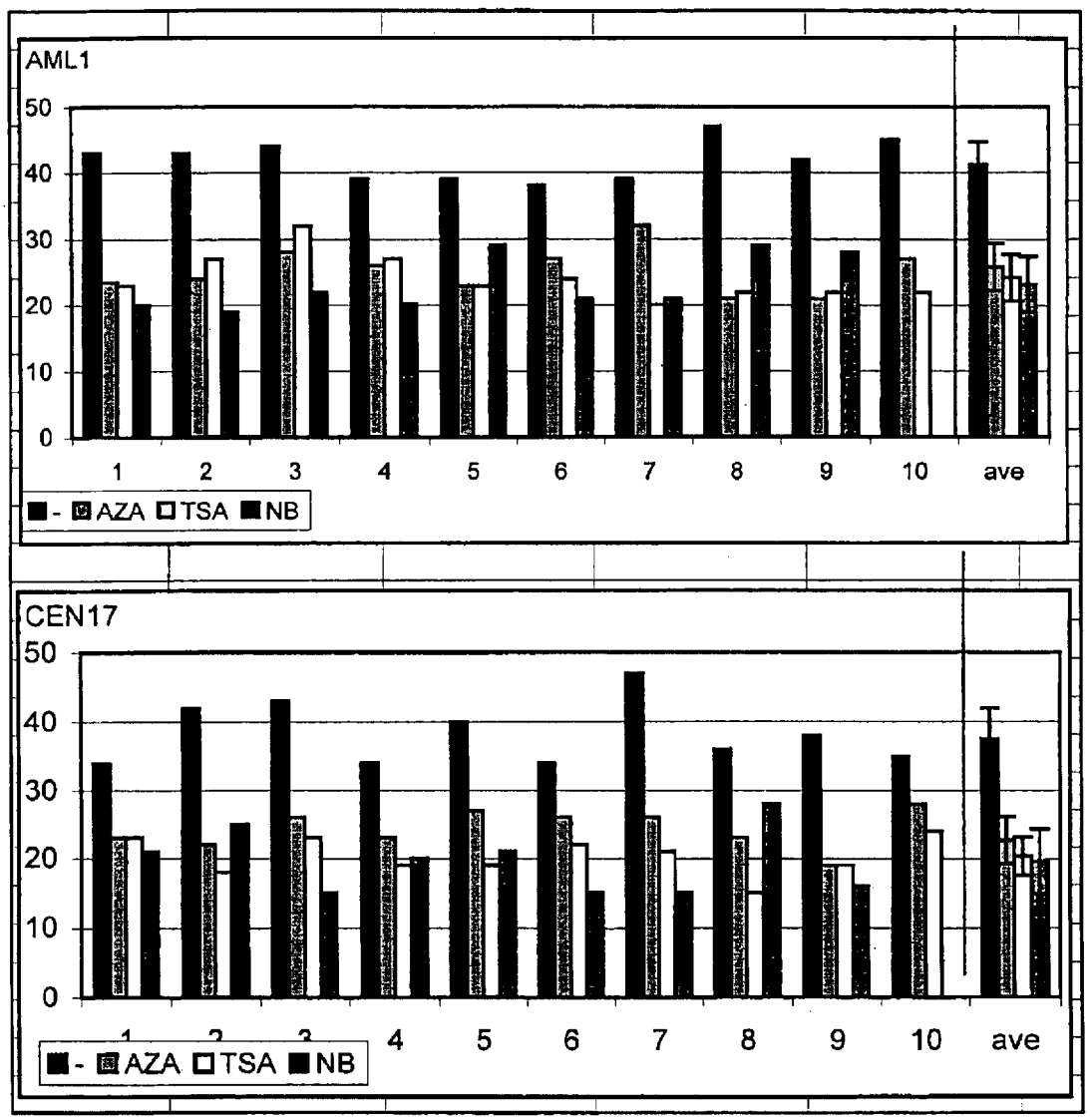
FIG. 19 shows the SD cell frequency (%) for 10 CAD individuals cultured in the absence of chromatin modifiers (solid bars); in the presence of AZA (light grey); in the presence of TSA (empty bars) and in the presence of NB (stripped bars).

The results indicate that while there is a marked difference in the frequency of SD cells between the CON samples and the CAD ones when cultured in the un-supplemented medium these differences were eradicated in the supplemented cultures. The supplements had almost no effect on the SD frequency in the CON samples with both probes (data not shown). FIG. 19 represents each sample's SD frequency (%) when grown with or without each of the supplements.

In addition to scoring the frequency of SD cells, we scored the frequency of losses and gains of chromosomes 21 and 17 in the same cytogenetic preparations (see example 6 for details). The levels of losses, gains and losses plus gains in the CAD samples are much higher than in the CON samples. These did not change with the addition of any of the supplements.

TABLE 1

The significance of the differences in the frequency (%) of SD cells for the AML1 and D17Z1 loci between CAD and CON samples. The corresponding means and standard deviations are also presented.

| | CON | CAD + AZA | CAD + TSA | CAD + NB |
|---|---|---|---|---|
| AML1 | N = 44<br>Mean = 18.8<br>Stdev = 3.4 | N = 20<br>Mean = 25.3<br>Stdev = 3.8 | N = 10<br>Mean = 24.2<br>Stdev = 3.5 | N = 10<br>Mean = 23.2<br>Stdev = 4.2 |
| CAD<br>N = 20<br>M = 41.2<br>Stdev = 3.5 | $P < 10^{-16}$ | $P < 10^{-15}$ | $P < 10^{-10}$ | $P < 10^{-8}$ |
| CON + AZA<br>N = 20<br>Mean = 21.5<br>Stdev = 4.5 | $p > 0.02$ | $p > 0.003$ | $p > 0.09$ | $p > 0.3$ |

| | CON | CAD + AZA | CAD + TSA | CAD + NB |
|---|---|---|---|---|
| CEN17 | N = 33<br>Mean = 19.5<br>Stdev = 4.1 | N = 20<br>Mean = 22.7<br>Stdev = 3.4 | N = 10<br>Mean = 20.3<br>Stdev = 2.8 | N = 10<br>Mean = 19.6<br>Stdev = 4.7 |
| CAD<br>N = 20<br>Mean = 37.5<br>Stdev = 4.5 | $P < 10^{-12}$ | $P < 10^{-9}$ | $P < 10^{-13}$ | $P < 10^{-7}$ |
| CON + AZA<br>N = 20<br>Mean = 20.9<br>Stdev = 5.0 | $p > 0.1$ | $p > 0.9$ | $p > 0.3$ | $p > 0.2$ |

The above examples demonstrate how to use the present invention, as well as the effectiveness of the present invention to detect tumors of various types in humans. Accordingly, the present invention is demonstrated to be generically useful for the detection of cancer and the assessment of cancer risk.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Amiel, A, Litmanovitch T, Lishner M, Mor A, Gaber E, Fejgin M D, Avivi L: Temporal differences in replication timing of homologous loci in malignant cells derived from CML and lymphoma patients. Genes Chrom. Cancer 22:225–231, 1998a.

Amiel A, Kolodizner T, Fishman A, Gaber E, Klein Z, beyth Y, Fejgin M D: Replication pattern of the p53 and 21q22 loci in the premalignant and malignant stages of carcinoma of the cervix. Cancer 83: 1966–1971, 1998b.

Amiel A, Korenstein A, Gaber E, Avivi L: Asynchronous replication of alleles in genomers carrying an extra autosome. Dur J Hum Genet 7:223–230, 1999a.

Amiel A, Kirgner I, Gaber E, Manor Y, Fejgin M, Lishner M: Replication pattern in cancer; asynchronous replication in multiple myeloma and in monoclonal gamopathy, Cancer Genet. Cytogenet. 108:32–37, 1999b.

Amiel A, Kitay-Cohen Y, Fejgin M D, Lishner M: Replication status as a marker for predisposition for lymphoma in patients with chronic hepatitis C with and without cryoglobulinemia. Exp Hematology 28:156–160, 2000.

Boggs B A, Chinault A C: Analysis of DNA replication by fluorescence in situ hybridization. Methods 13:259–270, 1997.

Dotan Z A, Dotan A, Litmanovitch T, Ravia Y, Ioniasvili N, Leibovitch I, Ramon J, Avivi L: Modification in the inherent mode of allelic replication in lymphocytes of patients suffering from renal cell carcinoma; a novel genetic alteration associated with malignancy. Genes Chromosomes & Cancer 27:270–277, 2000.

Friend S H, Bernards S, Rogell S, Weinberg R A, Rapaport J M, Albert D M: A human DNA segment with properties of the gene that predisposes to retinoblastoma and osteosarcoma. Nature 323:643–646, 1986.

Haaf T: The effects of 5-azacytidine and 5-azadeoxycytidine on chromosome structure and function; implications for methylation-associated cellular processes. Pharmac Ther 65:19–46, 1995.

Jacson A L, Loeb L A: The mutation rate and cancer. Genetics 148:1483–1490, 1998.

Lengauer C, Kinzler K W, Vogelstein, B: Genetic instabilities in human cancers. Nature 396:643–649, 1998.

Lengauer C, Kinzler K W, Vogelstein B: Genetic instability in colorectal cancers. Nature 386:623–627, 1998.

Loeb L A: Mutator phenotype may be required for multistage carcinogenesis. Cancer Res 51:3075–3079, 1991.

Loeb L A, Christians F C: Multiple mutations in human cancers. Mut Res 350:279–286, 1996.

Look A T: Oncogenic transcription factors in the human acute leukemias. Science 278: 1059–1064, 1997.

Litmanovitch T. Altaras M M, Dotan A, Avivi L: Asynchronous replication of homologous α-satellite DNA loci in man is associated with non-disjunction. Cytogenet Cell Genet 81:26–35, 1998.

Ozcelik T, Leff S, Robinson W, Donolon T, Lalande M, Sanjines E, Schinzel A, francke U: Small nuclear ribonucleoprotein polypeptide N (SNRPN), an expresses gene in the Prader-Willi syndrome region. Nature Genet 2:265–269, 1992.

Prokooimer M, Unger R, Rennert H S, Rotter V, Rennert G: Pooled analysis of p53 mutations in hematological malignancies. Hum Mut 12:4–18, 1998.

Rooney D E, Czepulkowsli B H: Human Cytogenetics (A Practical Approach). New York, N.Y. IRL Press, 1992.

Yeshaya J, Shalgi R, Shohat M, Avivi L: FISH-detected delay in replication timing of mutated FMR1 alleles on both active and inactive X-chromosomes. Hum Genet 105:86–97, 1999.

ELF-EMF European Feasibility Study Group (1997) *Scand. J. Work Environ. Health* 23, 5–14.

Lacy-Hulbert, A., Metcalfe, J. C. & Hesketh, R. (1998) *FASEB* 12, 395–420.

Miller, R. D., Nueberger, J. S. & Gerald, K. B. (1997) *Epidermol. Rev.* 19, 273–293.

Hardell, L. et al. (1995) *Eur. J. Cancer Prev.* 4 (Suppl 1), 3–107.

McCann, J., Dietrich, F. & Rafferty, C. (1998) *Mutat Res-Rev in Mutat* 411, 45–86.

Lengauer, C., Kinzler, K. W. & Vogelstein, B. (1998) *Nature* 396, 643–649.

Mitelman, F., Johansson, B. & Mertens, F. (1994) *Catalog of chromosome aberrations in cancer* Vol. 2 (Wiley-liss, New York).

Orr-Weaver, O. & Weinberg, R. A. (1998) *Nature* 392, 223–224. Sullivan, B. A., Schwartz, S. & Willard, H. F. (1996) *Environ. Mol. Mutagen.* 28, 182–191.

Fearon, E. R. (1998) in *The Gennetic Basis of Human Cancer*, eds, Vogelstein, B. & Kinzler, K. W. (McGraw-Hill, New York), pp. 229–236.

Zhuang, Z. et al. (1998) *Nature Genet.* 20, 66–69.

Avivi, L. et al. (1989) *Hum. Genet.* 83, 165–170.

Kinzler, K. W. & Vogelstein, B. (1996) *Cell* 87, 159–170.

Lengauer, C., Kinzler, K. W. & Vogelstein B. (1997), *Nature* 386, 623–627.

Cahill, D. P. et al.(1998) *Nature* 392, 300–303.

Litmanovitch, T., Altaras, M. M., Dotan, A. & Avivi, L. (1998) *Cytogenet. Cell Genet.* 81, 26–35.

Hagmar, L. et al. (1994) *Cancer Res.* 54, 2919–2922.

Bonassi, S. et al.(1995) *Cancer Genet. Cytogenet.* 79, 133–135.

International commission for protection against environmental mutagens and carcinogens, (1988) *Mutat. Res.* 204, 379–406.

Wang, S. I. et al.(1997) *Cancer Res.* 57, 4183–4186.

Prokocimer, M., Unger, R. Rennet, H. S., Rotter, V., & Rennet, G. (1998) *Hum. Mut.* 12, 4–18.

Pinkel, D., Straume, T. & Gray, J. W. (1986) *Proc. Natl. Acad. Sci. USA* 83, 2934–2938.

Eastmond, D. A. & Pinkel, D. (1990) *Mutat. Res.* 234, 303–318.

Willard, H. F. & Waye, J. S. (1987) *Trends Genet.* 3, 192–198.

Schwartz, M., Fichler, H. & Korenstein, R. (1984) *Bioelectrochem. & Bioenerg.* 12, 581–592.

Montgomery, B. G. (1969) *Solenoid magnet. Design.* (Wiley-interscience, New York London-Sydney-Tokyo).

Ahlbom, A. et al. (1998) *Health Phys.* 74, 494–522.

Amiel, A., Litmanovich, T., Lishner, M., Mor, A., Gaber, E., Fejgin, M. D. & Avivi, L. (1998) *Genes Chrom. Cancer* 22, 225–231.

Jones, P. A. & Conzalo, M. L. (1997) *Proc. Nati. Acad. Sci. USA* 94, 2103–2105.

Jones, P. A. & Laired P. W. (1999) *Nat. Genet.* 21, 163–167.

Lengauer, C., Kinzler, K. W. & Vogelstein, B. (1997) *Proc. Natl. Acad. Sci. USA* 94, 2545–2550.

Amiel A, Litmanovitch T, Gaber E, Lishner M, Avivi L, Fejgin M (1997) Asynchronous replication of p53 and 21q22 loci in chronic lymphocytic leukemia. Hum Genet 101:219–222.

Amiel A, Litmanovitch T, Lishner M, Mor A, Gaber E, Fejgin M D, Avivi L (1998a) Temporal differences in replication timing of homo logous loci in malignant cells derived from CML and lymphoma patients. Genes Chrom. Cancer 22:225–231.

Amiel A, Avivi L, Gaber E, Fejgin M D (1998b) Asynchronous replication of allelic loci in Down syndrome. Eur J Hum Genet 6:359–364.

Amiel A, Korenstein A, Gaber E, Avivi, L (1999) Asynchronous replication of alleles in genomes carrying an extra autosome. Eur J Hum Genet 7:223–230

Atkins L, Taft P, Kalal K P (1962) Asynchronous DNA synthesis of sex chromatin in human interphase nuclei. J Cell Biol 15:390–393.

Avivi L, Dotan A, Ravia Y, Amiel A, Shacham H, Neumann Y (1989) Increased spindle resistance to antimicrotubule agents in cells prone to chromosomal nondisjuction. Hum Genet 83:165–170.

Boggs B A, Chinault A C (1994) Analysis of the replication timing properties of human X-chromosomal loci by fluorescence in-situ hybridization. Proc Natl Acad Sci. USA 91:6083–6087.

Boggs B A, Chinault A C (1997) Analysis of DNA replication by fluorescence in situ hybridization. Methods 13:259–270.

Chess A (1998) Expansion of the allelic exclusion principle? Science 279:2067–2068

Chess A, Simon I, Cedar H, Axel R (1994) Allelic inactivation regulates olfactory receptor gene expression. Cell 78:823–834.

Cui H, Horon I L, Ohlsson R. Hamilton S R, Feinberg A P (1998) Loss of imprinting in normal tissue of colorectal cancer patients with microsatellite instability. Nat Med 4:1276–1280.

Dhar V, Magar D, Iqbal A, Schildkraut C L (1988) The coordinate replication of the human β-globin gene domain reflects its transcriptional activity and nuclease hypersensitivity. Mol Cell Biol 8:4958–4965.

Dhar V, Scoultchi A I, Schildkraut C L (1989) Activation and repression of a β-globin gene in cell hybrids is accompanied by a shift in its temporal replication. Mol Cell Biol 9:3524–3532.

Epner E, Rifkind R A, Marks P A (1981) Replication of α and β globin DNA sequences occurs during early S-phase in murine erythroleukemia cells. Proc Natl Acad Sci USA 78:3058–3062.

Epner E, Forrester W C, Groudine M (1988) Asynchronous DNA replication within the human β-globin gene. Proc Natl Acad Sci USA 85:8081–8085

Feinberg A P (1998) Genomic imprinting and cancer. In: Vogelstein B, Kinzler K W (eds) The genetic basis of human cancer. McGraw-Hill, New York, pp. 95–107.

Goldman M A, Holmquist G P, Gray M C, Caston L A, Nag A (1984) Replication timing of mammalian genes and middle repetitive sequences. Science 224:686–692.

Grumbach M M., Morishima A, Taylor J H (1963) Human sex chromosome abnormalities in relation to DNA replication and heterochromatinization. Proc Natl Acad Sci USA 49:581–589.

Gunaratne P H, Nakao M, Ledbetter D H, Sutcliffe J S, Chinault A C (1995) Tissue-specific and allele-specific replication timing control in the imprinted human Prader-Willi syndrome region. Genes & Dev 9:808–820.

Hatton K S, Dhar, V H, Brown E H, Iqbal M A, Stuart S, Didamo V T, Schidkraut C L (1988) Replication program of active and inactive multigene families in mammalian cells. Mol Cell Biol 8:2149–2158.

Hollander G A, Zuklys S, Morel C, Mizoguchi E, Mobisson K, Simpson S, Terhorst C, Wishart W, Golan D E, Bhan A K, Burakoff S J (1998) Monoallelic expression of the interleukin-2 locus. Science 279:2118–2121.

Holmquist G P (1987) Role of replication time in the control of tissue specific gene expression. Am J Hum Genet 40:151–173.

Jackson A L, Loeb L A (1998) The mutation rate and cancer. Genetics 148:1483–1490.

Kinzler K W, Vogelstein B (1995) Colorectal tumors. In: Scriver C R, Beaudet A L, Sly W S, Valle D (eds) The metabolic and molecular bases of inherited disease, 7$^{th}$ ed. Vol 1. McGraw-Hill, New York, pp. 643–663.

Kitsberg D, Selig S, Brandeis M, Simon I, Keshet I, Driscoll D J, Nicholls RD, Cedar H (1993) Allele-specific replication timing of imprinted gene regions. Nature 364:459–463.

Knoll J H M, Cheng S D, Lalande M (1994) Allele specificity of DNA replication timing in the Angelman/Prader- Willi syndrome imprinted chromosomal region. Nat Genet 6:41–46.

Knudson A G (1993) Antioncogenes and human cancer. Proc Natl Acad Sci USA 90:10914–10921.

LaSalle J M, Lalande M (1995) Domain organization of allele-specific replication within the GABRB3 gene cluster requires a biparental 15q11–13 contribution. Nat Genet 9:386–394.

Levanone D, Negreanu V, Bernstein Y, Bar-Am I, Avivi L, Groner Y (1994) AML1, AML2, and AML3, the human members of the runt domain gene-family: cDNA structure, expression, and chromosomal localization. Genomics 23:425–432.

Levine A J (1997) p53, the cellular gatekeeper for growth and division. Cell 88:323–331.

Lima de Faria A, Reitaln J, Bergmann S (1961) The pattern of DNA replication in synthesis in the chromosomes of man. Cancer Genet Cytogenet 3:171–181.

Lima de Faria A, Jaworska H (1968) Late DNA synthesis in heterochromatin. Nature 217:138–142.

Linehan W M, Lerman M I, Zbar B (1995) Identification of the VHL gene: its role in renal caecinoma. JAMA 273:564–570.

Litmanovitch T, Altaras M M, Dotan A, Avivi L (1998) Asynchronous replication of homologous α-satellite DNA loci in man is associated with non-disjunction. Cytogenet Cell Genet 81:26–35.

Loeb L A (1991) Mutator phenotype may be required for multistage carcinogenesis. Cancer Res 51:3075–3079.

Look T (1998) Genes altered by chromosomal translocations in leukemia and lymphomas. In: Vogelstein B, Kinzler K W (eds) The genetic basis of human cancer. McGraw-Hill, New York, pp. 109–141.

Miller O J, Schnedl W, Allen J, Erlanger B F (1974) 5-Methylcytosine localized in mammalian constitutive heterochromatin. Nature 251:636–637.

Miller O J (1976) Is the centromeric hetrochromatin of Mus musculus late replicating? Chromosoma 55:165–170.

Mukherjee A B, Murty V V V S, Chaganti R S K (1992) Detection of cell-cycle stage by fluorescence in situ hybridization: its application in human interphase cytogenetics. Cytogenet Cell Genet 61:91–94.

Ohlsson R, Tycko B. Sapienza C (1998) Monoallelic expression: 'there can only be one'. TIG 14:435–438

Priest J, Heady J E, Priest R E (1967) Delayed onset of replication of human X chromosomes. J Cell Biol 35:483–487.

Randlhawa G S, Cui H, Barletta J A, Strichman-Almashanu L Z, Talpaz M, Kantarjian H, Deisseroth A B, Champlin R C, Feinberg A P (1998) Loss of imprinting in disease progression in chronic myelogenous leukemia. Blood 91:3144–3147

Selig S, Ariel M, Goitein R, Marcus M, Cedar H (1988) Regulation of mouse satellite DNA replication time. EMBO J 7:419–426.

Selig S, Okumura K, Ward D C, Cedar H (1992) Delineation of DNA replication time zones by fluorescence in situ hybridization. EMBO J 11:1217–1225.

Smrzka O W, Fae I, Stoger R, Kurzbauer R, Fischer G F, Henn T, Weith A, Barlow D P (1995) Conservation of maternal-specific methylation signal at the human IGF2R locus. Hum Mol Genet 4:1945–1952

Taylor J H (1960) Asynchronous duplication of chromosomes in cultured cells of Chinese hamster. J Biophys Biochem Cytol 7: 455–464.

Ten Hagen K G, Gilbert D M., Wilard H F, Cohen S N (1990) Replication timing of DNA sequences associated with human centromeres and telomeres. Mol Cell Biol 10:6348–6355.

Torchia B S, Call L M, Migeon B R (1994) DNA replication analysis of FMR1, XIST, and factor 8C loci by FISH shows nontranscribed X-linked genes replicate late. Am J Hum Genet 55:96–104

White L M, Rogan P K, Nicholls R D, Wu B L, Korf B, Knoll J H M (1996) Allele specific replication of 15q11–q13 loci: a diagnostic test for uniparental disomy. Am J Hum Genet 59:423–430.

Willard H F, Latt S A (1976) Analysis of deoxyribonucleic acid replication in human X chromosomes by fluorescence microscopy. Am J Hum Genet 28:213–227.

Yeshaya J, Shalgi R, Shohat M, Avivi L (1999) FISH-detected delay in replication timing of mutated FMR1 alleles on both active and inactive X-chromosomes. Hum Genet (in press).

What is claimed is:

1. A method for diagnosing prostate or breast cancer, comprising:
   a) obtaining cells from a body fluid in an individual suspected to have prostate or breast cancer; and
   b) determining the synchrony in replication timing between alleles of one or more DNA loci in said cells, wherein a determination of asynchrony between alleles of one or more DNA loci, which replicate synchronously in normal diploid cells, or a determination of synchrony between alleles of one or more DNA loci, which replicate asynchronously in normal diploid cells and are selected from the group of DNA loci consisting of loci on the X-chromosome in female individuals and loci subjected to allelic exclusion, provides positive predictability of prostate or breast cancer in the individual.

2. The method of claim 1, which is for diagnosing prostate cancer, wherein the cells in step (a) are obtained from a body fluid in an individual suspected to have prostate cancer.

3. The method of claim 2, wherein the cells are subjected to a growth stimulus before step (b).

4. The method of claim 2, wherein the cells are subjected to chromatin and/or DNA modifiers before step (b).

5. The method of claim 4, wherein the cells are subjected to chromatin and/or DNA modifiers selected from the group consisting of 5-azacytidine, Trichostatin A, Sodium Butirate, and N-nitroso-n-methylurea.

6. The method of claim 2, wherein the body fluid is selected from the group consisting of blood, amniotic fluid, urine, and saliva.

7. The method of claim 6, further including the step of isolating cells from bodily fluids.

8. The method of claim 6, wherein the blood is peripheral blood.

9. The method of claim 8, further including the step of isolating peripheral blood cells.

10. The method of claim 2, wherein the cells are lymphocytes.

11. The method of claim 2, wherein the one or more loci are non-coding DNA regions.

12. The method of claim 2, wherein the one or more loci are selected from satellited DNA arrays.

13. The method of claim 2, wherein the one or more loci are centromere-associated.

14. The method of claim 2, wherein the one or more loci are tumor-associated genes.

15. The method of claim 2, wherein the one or more loci are selected from the group consisting of oncogenes, tumor suppressor genes, and transcription factors.

16. The method of claim 2, wherein the one or more loci replicate synchronously in normal diploid cells.

17. The method of claim 16, wherein the one or more loci are expressed biallelically.

18. A method for diagnosing prostate cancer, comprising:
   a) obtaining cells from a body fluid in an individual suspected to have prostate cancer; and
   b) determining the synchrony in replication timing between alleles of one or more DNA loci in said cells, wherein a determination of asynchrony between alleles of one or more DNA loci, which replicate synchronously in normal diploid cells, provides positive predictability of prostate cancer in the individual and wherein said one or more DNA loci are selected from the group consisting of HER2, CMYC, TP53, RB1, D21S55, D22S75 and DSTS WI-941 and alpha, II and III satellites for all chromosomes.

19. The method of claim 2, wherein the one or more loci replicate asynchronously in normal diploid cells, are expressed monoallelically, and are selected from the group consisting of loci on the X-chromosome in female individuals and loci subjected to allelic exclusion.

20. The method of claim 2, wherein the determination of asynchrony is a change in synchrony of replication timing of between about 3% to about 55% relative to replication timing in normal individuals.

21. The method of claim 20, wherein the change in synchrony is an increase in asynchrony of between about 15% to about 35%.

22. The method of claim 20, wherein the change in synchrony is a decrease in asynchrony of between about 10% to about 20%.

23. The method of claim 2, wherein synchrony of replication timing is determined by fluorescence in situ hybridization.

24. The method of claim 1, which is for diagnosing breast cancer, wherein the cells in step (a) are obtained from a body fluid in an individual suspected to have breast cancer.

25. The method of claim 24, wherein the cells are subjected to a growth stimulus before step (b).

26. The method of claim 24, wherein the cells are subjected to chromatin and/or DNA modifiers before step (b).

27. The method of claim 26, wherein the cells are subjected to chromatin and/or DNA modifiers selected from the group consisting of 5-azacytidine, Trichostatin A, Sodium Butirate, and N-nitroso-n-methylurea.

28. The method of claim 24, wherein the body fluid is selected from the group consisting of blood, amniotic fluid, urine, and saliva.

29. The method of claim 28, further including the step of isolating cells from bodily fluids.

30. A method of claim 28, wherein the blood is peripheral blood.

31. The method of claim 30, further including the step of isolating peripheral blood cells.

32. The method of claim 24, wherein the cells are lymphocytes.

33. The method of claim 24, wherein the one or more loci are non-coding DNA regions.

34. The method of claim 24, wherein the one or more loci are selected from satellited DNA arrays.

35. The method of claim 24, wherein the one or more loci are centromere-associated.

36. The method of claim 24, wherein the one or more loci are tumor-associated genes.

37. The method of claim 24, wherein the one or more loci are selected from the group consisting of oncogenes, tumor suppressor genes, and transcription factors.

38. The method of claim 24, wherein the one or more loci replicate synchronously in normal diploid cells.

39. The method of claim 38, wherein the one or more loci are expressed biallelically.

40. A method for diagnosing breast cancer, comprising:
   a) obtaining cells from a body fluid in an individual suspected to have breast cancer; and
   b) determining the synchrony in replication timing between alleles of one or more DNA loci in said cells, wherein a determination of asynchrony between alleles of one or more DNA loci, which replicate synchronously in normal diploid cells, provides positive predictability of breast cancer in the individual and wherein said one or more loci are selected from the group consisting of HER2, CMYC, TP53, RB1, D21S55, D22S75 and DSTS WI-941 and alpha, II and III satellites for all chromosomes.

41. The method of claim 24, wherein the one or more loci replicate asynchronously in normal diploid cells, are expressed monoallelically, and are selected from the group consisting of loci on the X-chromosome in female individuals and loci subjected to allelic exclusion.

42. The method of claim 24, wherein the determination of asynchrony is a change in synchrony of replication timing of between about 3% to about 55% relative to replication timing in normal individuals.

43. The method of claim 42, wherein the change in synchrony is an increase in asynchrony of between about 15% to about 35%.

44. The method of claim 42, wherein the change in synchrony is a decrease in asynchrony of between about 10% to about 20%.

45. The method of claim 24, wherein synchrony of replication timing is determined by fluorescence in situ hydridization.

* * * * *